US005610041A

United States Patent [19]

Somerville et al.

[11] Patent Number: 5,610,041

[45] Date of Patent: *Mar. 11, 1997

[54] PROCESSES FOR PRODUCING POLYHYDROXYBUTYRATE AND RELATED POLYHYDROXYALKANOATES IN THE PLASTIDS OF HIGHER PLANTS

[75] Inventors: Christopher R. Somerville, Portola Valley; Christiane Nawrath; Yves Poirier, both of Palo Alto, all of Calif.

[73] Assignee: Board of Trustees operating Michigan State University, East Lansing, Mich.

[*] Notice: The portion of the term of this patent subsequent to Jun. 7, 2012, has been disclaimed.

[21] Appl. No.: 254,357

[22] Filed: Jun. 6, 1994

Related U.S. Application Data

[63] Continuation-in-part of Ser. No. 108,193, Aug. 17, 1993, abandoned, which is a continuation-in-part of Ser. No. 732,243, Jul. 19, 1991, abandoned.

[51] Int. Cl.$^6$ .............................. C12P 7/62; A01H 5/00; C12N 15/31; C12N 15/87
[52] U.S. Cl. .......................... 435/135; 800/205; 800/250; 800/255; 47/58; 435/320.1; 435/69.7; 435/141; 435/183; 435/189; 435/195; 536/23.4; 536/23.7
[58] Field of Search .............................. 435/172.3, 320.1, 435/69.1, 70.1, 69.7, 69.8, 240.4, 135, 141, 183, 189, 195; 800/205, 250, 255; 47/58; 536/23.4, 23.7

[56] References Cited

U.S. PATENT DOCUMENTS

| | | | |
|---|---|---|---|
| 5,229,279 | 7/1993 | Peoples et al. | 435/135 |
| 5,245,023 | 9/1993 | Peoples et al. | 536/23.2 |
| 5,250,430 | 10/1993 | Peoples et al. | 435/232 |

FOREIGN PATENT DOCUMENTS

| | | | |
|---|---|---|---|
| 9100917 | 1/1991 | WIPO | C12P 7/62 |
| 9219747 | 11/1992 | WIPO | C12N 15/82 |
| 93/02187 | 2/1993 | WIPO | C12N 15/00 |
| 9302194 | 2/1993 | WIPO | C12N 15/52 |
| 94/11519 | 5/1994 | WIPO | C12N 15/82 |
| 94/23027 | 10/1994 | WIPO | C12N 15/11 |

OTHER PUBLICATIONS

Anderson, A.J. and Dawes, E.A., Microbiol. Rev. 54: 450–472, 1990.
Steinbuchel, A. and Schlegel, H.G., Mol. Microbiol. 5: 535–542, 1991.
Peoples, O.P. and Sinskey, A.J., J. Biol. Chem. 264: 15293–15297, 1989.
J. Biol. Chem. 264: 15298–15303, 1989.
Slater, S.C., Voige W.H. and Dennis, D.E., J. Bacteriol. 170: 4431–4436, 1988.
Schubert, P., Steinbuchel, A. and Schlegel, H.G., J. Bacteriol. 170: 5837–5847, 1988.
Huisman, G.W., de Leeuw, O., Eggink, G., and Witholt, B. Appl. Environ. Microbiol 54:2924, 1988.
Doi, Y.(ed), In:Microbial polyesters, Chpt.3,and Chpt. 6 VCH Publisher, New York (1990).
Holmes, P.A. In: Developments in crystalline polymers–2 Basset, D. C. (ed), 1–65, 1988.
Gross, R.A., De Mello, C., Lenz, R.W., Brandl, H. and Fuller R.C., Macromolecules 22: 1106, 1989.
Doi, Y. (ed) In: Microbial Polyesters, Chpt.1., VCH Publishers, New York, 1990.
Dawes, E.A. and Senior, P.J., Adv. Microb. Physiol. 10: 135–266 (1973).
Koosha, R., Muller, R.H. and Davis, S.S. In: Critical reviews in therapeutic drug carrier system,6:117–129 (1989).
Poole, R., Science 245: 1187–1189 (1989).
Poirier, Y., Dennis, D.E., Nawrath, C. and Somerville, C. Adv. Mater. 5: 30–36 (1993).
Martin, J.H., Leonard, W.H. and Stamp, D.L. (eds), Chpt 36, In:Principles of Field Crop Prod. 898–932, Macmillan, New York, 1976.
Downey, R.K. and Robbelen, G., In: Oil crops of the world, Robbelen, G., Downey, R.K. and Ashri, A. (eds) Chpt. 16, McGraw–Hill, New York, 1989.
Hiatt, A., Cafferkey, R. and Bowdish, K., Nature 342: 76–78, 1989.
Moffat, A.S., Science 256: 770–771, 1992.
Poirier, Y., Dennis, E., Klomparens, K. and Somerville, C., Science 256: 520–523, 1992.
Poirier, Y., Dennis, D.E., Klomparens, K., Nawrath, C. and Somerville, C., FEMS Microbiol. Lett., 103: 237–246, 1992.
Cashmore, A.R. In: Genetic Engineering of plants (ed. Kosuge, T., Meredith, C.P. and Hollaender, A.) 29–38, Plenum Press NY, 1983.
Peoples, O.P. and Sinskey, A.J., J. Biol. Chem 264: 15298–15303, 1989.
Harwood, J.L., Ann. Rev. Plant Physiol. Plant Mol. Biol. 39: 101–138, 1988.
Preiss, J., Ann. Rev. Plant Physiol. 33: 431–454, 1982.
Keegstra, K. and Olsen, L. J., Annu. Rev. Plant Physiol. Plant Mol. Biol, 40: 471–501, 1989.
Archer, E.K. and Keegstra, K., J. Bioenerg. Biomem., 22: 789–810, 1990.
Robinson, C. and Ellis, R.J., Eur. J. Biochem, 142: 343–346, 1984.
Wasmann, C.C., Reis, R., Bartlett, S.G., and Bohnert, H.J., Mol. Gen. Genet. 205: 446–453, 1986.
Friedmann, A.L. and Keegstra, K., Plant Physiol. 89: 993–999, 1988.

(List continued on next page.)

Primary Examiner—Charles C. P. Rories
Attorney, Agent, or Firm—Ian C. McLeod

[57] ABSTRACT

The present invention relates to a process for producing poly-D-(-)-3-hydroxybutyric acid (PHB) and related polyhydroxyalkanoates (PHA) in the plastids of plants. The production of PHB is accomplished by genetically transforming plants with modified genes from microorganisms. The genes encode the enzymes required to synthesize PHB from acetyl-CoA or related metabolites and are fused with additional plant sequences for targeting the enzymes to the plastid.

36 Claims, 20 Drawing Sheets

OTHER PUBLICATIONS

Lubben, T.H., Gatenby, A.A., Ahlquist, P., and Keegstra, K., Plant Mol. Biol. 12: 13–18, 1989.

Schnell, D.J., Blobel, G., and Pain, D., J. Biol. Chem. 266: 3335–3342, 1991.

van de Broeck, G., Timko, M.P., Kausch, A.P., Cashmore, A.R., Van Montagu, M. and Herrera–Estrella, L., Nature 313: 358–363, 1985.

Schreier, P.H., Seftor, E.A., Schell, J., and Bohnert, H.J., EMBO J. 4: 25–32, 1985.

Boutry, M., Nagy, F., Poulsen, C., Aoyagi, K., and Chua N.–H., Nature 328: 340–342, 1987.

Lubben, T.H., and Keegstra, K., Proc. Natl. Acad. Sci 83: 5502–5506, 1986.

Lamppa, G.K., J. Biol. Chem, 263: 14996–14999, 1988.

Gatenby, A.A., Lubben, T.H., Ahlquist, P., and Keegstra, K., EMBO J. 7:1307–1314, 1988.

Cheung, A.Y., Bogorad, L., Van Montagu, M., and Schell, J., Proc. Natl. Acad, Sci. 85: 391–395, 1988.

Lubben, T.H., Theg, S. M. and Keegstra, K., Photosyn. Res. 17: 173–194, 1988.

Benfey, P.N. and Chua, N.–H., Science 250: 959–966, 1990.

Pang, P.P., Pruitt, R.E., and Meyerowitz, E.M., Plant Mol. Biol. 11: 805–820, 1988.

Becker, D., Nucleic Acids Res. 18: 203, 1990.

Bolivar, F. et al., Gene 2: 95–113, 1977.

Pridmore, R.D., Gene 56: 309–312, 1987.

Haughn, G.W., Smith, J., Mazur, B. and Somerville, C.R., Mol. Gen. Genet. 211: 266–271, 1988.

Koncz, C. and Schell, J., Mol. Gen. Genet. 204: 383–396, 1986.

Sambrook, J. Fritsch, E.F. and Maniatis, T. Molecular cloning, a laboratory manual, Cold Spring Harbor Laboratory Press, 1989.

Chang, S.S., Perk, S.K. and Nam, H.–G., Abstract in: Fourth International Conference on Arabidopsis Research, Vienna, 1990.

Senior, P.J. and Dawes, E.A., Biochem. J. 134: 225–238, 1973.

Hanahan, D., J. Mol. Biol. 166: 557–580, 1983.

Rogers, S. C. and Bendich, A.J., Plant Molecular Biology Manual A6: 1–10 (1988).

Feinberg, A.P., and Volgelstein, B., Anal. Biochem. 132, 6–13 (1983).

Poirier, Y., and Jolicoeur, P., J. Virol. 63: 2088–2098 (1989).

Laemmli, Nature 227: 680–685, 1970.

Janes, B., et al. E.A. Dawes (ed.) Novel Biodegradable Microbial Polymers, 175–190 (1990).

Ostle, Anthony G., Applied and Environmental Microbiology, pp. 238–241 (1982).

Kreuz and Kleinig, Eur. J. Biochem. 141, 531–535 (1984).

Schultz, G. & Schulze–Siebert, D. in Biological Role of Plant Lipids, eds. Biacs P.A., Gruiz, K., & Kremmer, T. (Plenum Publ.Corp.,N.Y.,N.Y. pp. 313–319 (1989).

Jorgensen, R. Trends in Biotechnology 8,340–344 (1990).

Fukui,T., et al., Arch. Microbiol. 110, 149–156 (1976).

Haywood, G.W., et al., FEMS Microbiol. Lett 57, 1–6 (1989).

Seymour, G.B., et al., Plant Mol. Biol. 23, 1–9 (1993).

Poirier, Yves, et al., Science, vol. 256 pp. 520–523 (24 Apr. 1992).

International Symposium on Bacterial Polyhydroxy–alkanoates ISBP '92; Gottingen, Jun. 1–5, (1992) L17.

UC Davis–Pacific Rim Food and Agricultural Biotechnology Conference Series–Jun. 20–24 (1992) Genetic Engineering of a Unique Biopolymer Polyhydroxybutyrate.

Poirier, Yves, et al., FEMS Microbiology Reviews 103, 237–246 (1992).

Poirier, Yves, et al., Adv. Mater., 5, No. 1 30–37 (1993).

Proceedings of the Canadian Society of Plant Physiologists, Dec. 13–15, (1992) University of Montreal.

Balter, M., "Plastics: A 21st–Century Crop?", International Herald Tribune (Dec. 15, 1989).

Estelle, M.A. and C. Somerville, "Auxin–resistant Mutants of *Arabidopsis thaliana* with an Altered Morphology", Mol. Gen. Genet., vol. 206, No. 2, pp. 200–206 (no month identified 1987).

Gerbling, H. and B. Gerhart, "Peroxisomal Degradation of Branched–chain 2–Oxo Acids[1,2]", Plant Physiol., vol. 91, pp. 1387–1392 (Jul. 1989).

Goodwin, T.W. and E.L. Mercer, "Respiration", In Introduction to Plant Biochemistry, Pergamon Press, Chapter 6, pp. 162–226 (no month identified 1983).

Holmes, P.A., "Applications of PHA – A Microbially Produced Biodegradable Thermoplastic", Phys. Technol., vol. 16, No. 1, pp. 32–36 (no month identified 1985).

Horsch, R., R.T. Fraley, S.G. Rogers, P.R. Sanders, A. Lloyd and N. Hoffmann, "Inheritance of Functional Foreign Genes in Plants", Science, vol. 223, pp. 496–498 (Feb. 1984).

Huisman, G.W., E. Wonink, R. Meima, B. Kazemier, P. Terpstra and B. Witho, "Metabolism of Poly(3–hydroxyalkanoates) (PHAs) by *Pseudomonas oleovorans*", J. Biol. Chem., vol. 266, No. 4, pp. 2191–2198 (Feb. 1991).

Huisman, G.W., O. de Leeuw, G. Eggink and B. Witholt, "Synthesis of Poly–3–hydroxyalkanoates Is a Common Feature of Fluoresent Pseudomonads", Applied and Environmental Microbiology, vol. 55, No. 8, pp. 1949–1954 (Aug. 1989).

Kung, S.D. and R. Wu, (eds), "Production of *Bacillus thuringiensis* Insecticidal Proteins in Plants", in Transgenic Plants, vol. 1, pp. 297–315 (no month identified 1993).

Lloyd, A., A.R. Barnason, S.G. Rogers, M.C. Byrne, R.T. Fraley and R.B. Horsch, "Transformation of *Arabidopsis thaliana* with *Agrobacterium tumefaciens*", Science, vol. 234, pp. 464–466 (Oct. 1986).

Lundgren, D.G., R.M. Pfister and J.M. Merrick, "Structure of Poly–β–hydroxbutyric Acid Granules", J. Gen. Microbiol., vol. 34, No. 3, pp. 441–446 (May 1964).

Mahler, H.R., "Biological Oxidation of Fatty Acids", in Fatty Acids, Their Chemistry, Properties, Production and Uses, (Part 3, Markley, K.S.), R.E. Krieger Publishing, Chapter XV, pp. 1487–1550 (no month identified 1983).

Peoples, O.P. and A.J. Sinskey, "Fine Structural Analysis of the *Zoogloea ramigera* phbA–phbB Locus Encoding β–ketothiolase and Acetoacetyl–CoA Reductase: Nucleotide Sequence of phbB", Mol. Microbiol., vol. 3, No. 3, pp. 349–357 (Mar. 1989).

Peoples, O.P. and A.J. Sinskey, "Polyhydroxybutyrate (PHB): A Model System for Biopolymer Engineering: II", in Dawes, E.A. (ed) Proceedings of the NATO Advanced Research Workshop, pp. 191–202 (May 26–31, 1990).

Potty, V.H., "Occurrence and Properties of Enzymes Associated with Mevalonic Acid Synthesis in the Orange", J. Food Sci., vol. 34, No. 3, pp. 231–234 (May/Jun. 1969).

Puissant, C. and L.M. Houdebine, "An Improvement of the Single–step Method of RNA Isolation by Acid Guanidinium Thiocynate–Phenol–Chloroform Extraction", Bio Techniques, vol. 8, No. 2, pp. 148–149 (Feb. 1990).

Schiefelbein, J.W. and C.R. Somerville, "Genetic Control of Root Hair Development in *Arabidopsis thaliana*", Plant Cell, vol. 2, pp. 235–243 (Mar. 1990).

Southern, E.M., "Detection of Specific Sequences Among DNA Fragments Separated by Gel Electrophoresis", J. Mol. Biol., vol. 98, pp. 503–517 (Nov. 1975).

Steinbüchel, A., E. Hustede, M. Liebergesell, U. Pieper, A. Timm and H. Valentin, "Molecular Basis for Biosynthesis and Accumulation of Polyhydroxyalkanoic Acids in Bacterial", FEMS Microbiol. Rev., vol. 103, No. 2/4, pp. 217–230, (Dec. 9, 1992).

Valvekens, D., M. Van Montagu and M. Van Lijsbettens, "*Agrobacterium tumefaciens*–mediated Transformation of *Arabidopsis thaliana* Root Explants by Using Kanamycin Selection", Proc. Natl. Acad. Sci. USA, vol. 85, pp. 5536–5540 (Aug. 1988).

Wallen, L.L. and W.K. Rohwedder, "Poly–β–hydroxyalkanoate from Activated Sludge", Environ. Sci. Technol., vol. 8, No. 6, pp. 576–579 (Jun. 1974).

Witholt, B., G.W. Huisman and H. Preusting., "Bacterial Poly(3–hydroxyalkanoates)", Proceedings of the NATO Advanced Research Workshop, pp. 161–173 (May 26–31, 1990).

Zambryski, P., H. Joos, C. Genetello, J. Leemans, M. Van Montagu and J. Schell, "Ti Plasmid Vector for the Introduction of DNA into Plant Cells Without Alteration of their Normal Regeneration Capacity", EMBO, vol. 2, No. 12, pp. 2143–2150 (Dec. 1983).

Ser. No. 08/108,193 filed Aug. 17, 1993 by Somerville et al.

Ser. No. 08/472,358 filed Jun. 7, 1995 by Somerville et al.

C. Nawrath et al., "Production of Polyhydroxybutyrate in Higher Plants", Abstr. Pap. Am. Chem. Soc., vol. 206, (1993), AGRO 167. 206th American Chemical Society National Meeting, Chicago, IL (Aug. 22–27, 1993).

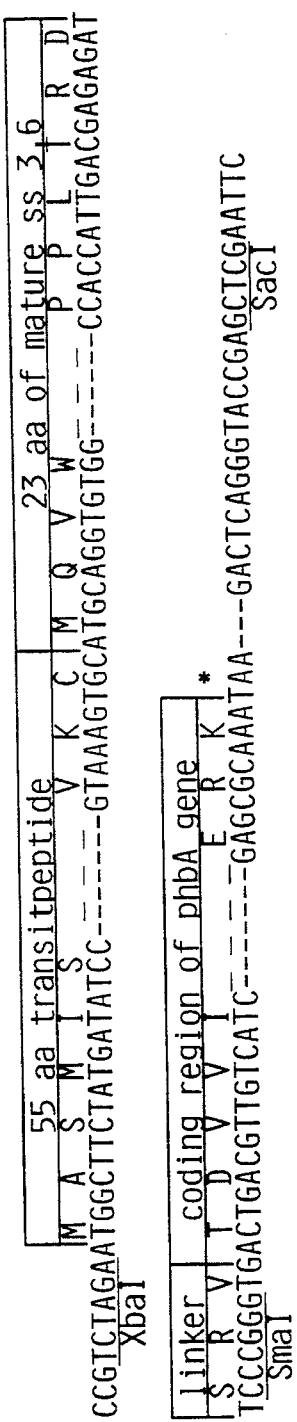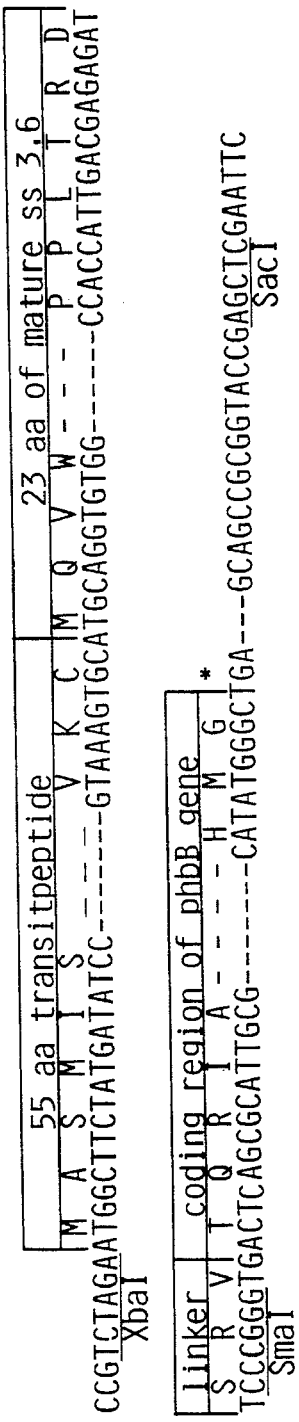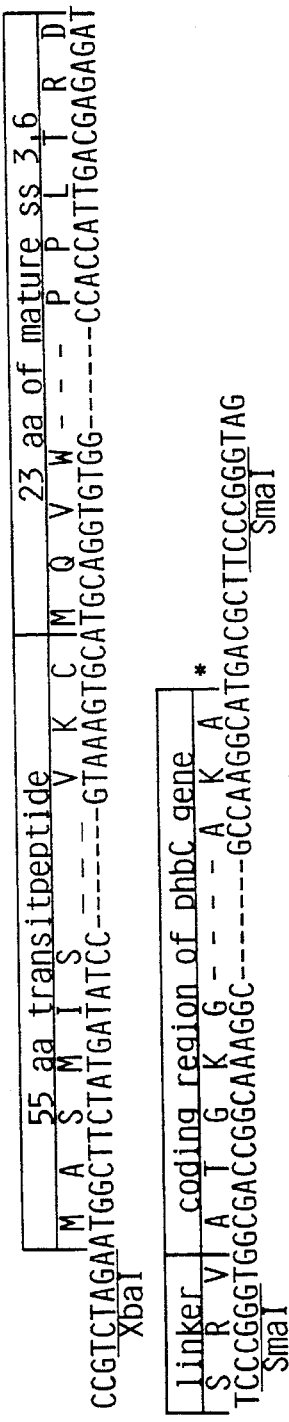

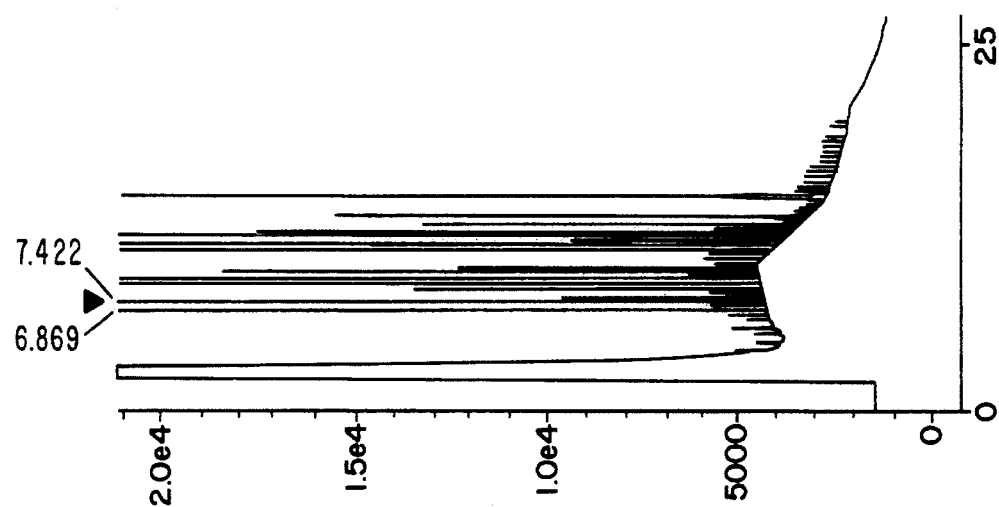
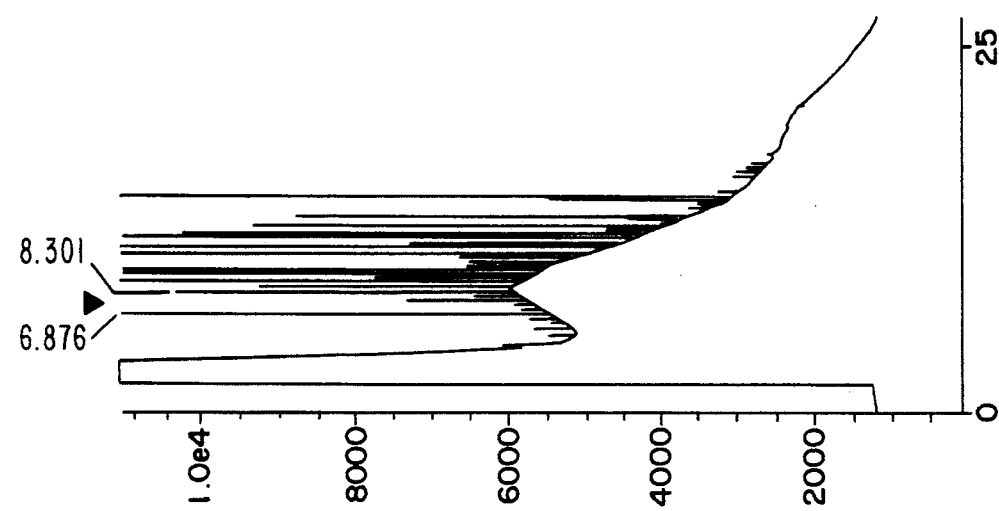
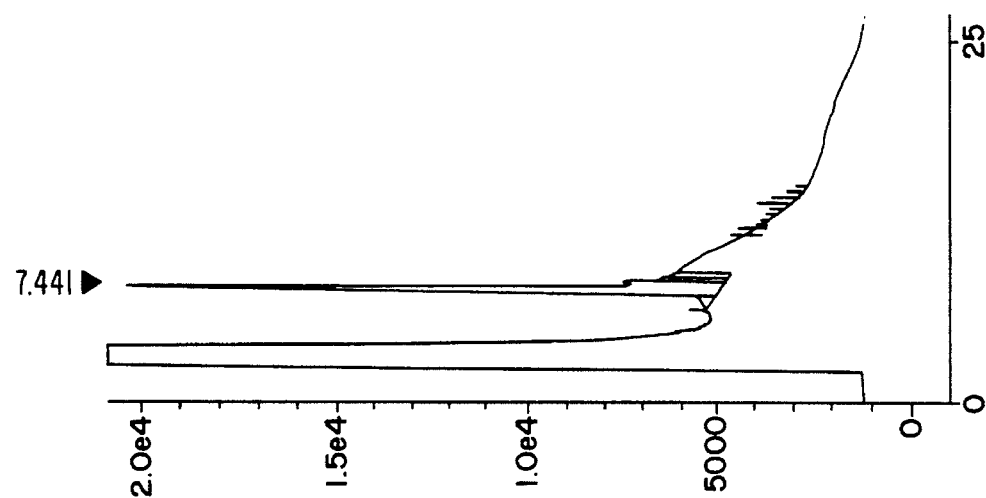

A　　B

PROCESSES FOR PRODUCING POLYHYDROXYBUTYRATE AND RELATED POLYHYDROXYALKANOATES IN THE PLASTIDS OF HIGHER PLANTS

GOVERNMENT RIGHTS

The invention described herein was made in the course of work under grant number DE-AC02-76ERO-1338 from the U.S. Department of Energy and No. DMB 9014037 from the National Science Foundation. The U.S. Government has certain rights under this invention.

CROSS-REFERENCE TO RELATED APPLICATION

This application is a continuation-in-part of U.S. application Ser. No. 08/108,193, filed Aug. 17, 1993, now abandoned, which is a continuation-in-part of Ser. No. 07/732,243, filed Jul. 19, 1991, now abandoned.

BACKGROUND OF THE INVENTION (1) Field of the Invention

This patent concerns inventions which improve the production of a class of material called polyhydroxyalkanoates (PHA) in higher plants. PHA is a group of bacterial polymeric material composed of linear polyesters of hydroxy acids and has thermoplastic properties. A low level production of PHA has previously been demonstrated in *Arabidopsis thaliana* transformed with the bacterial genes involved in PHA synthesis as described in Ser. No. 07/732,243, filed Jul. 19, 1991. In order to produce large amounts of PHAs in higher plants, the enzymes for PHA production have to be located in a subcellular compartment possessing a high level of precursor for PHA synthesis which is the plastid. The three genes of *Alcaligenes eutrophus* involved in synthesis of PHA from acetyl-CoA were modified to target the corresponding enzymes to the plastid of Arabidopsis plant cells as a specific example of the present invention.

(2) Description of Related Art

Polyhydroxyalkanoates (PHA), polyesters of 3-hydroxyacids, are produced as carbon storage reserves by a large variety of bacteria (Anderson, A. J. and Dawes, E. A., Microbiol. Rev. 54: 450–472, 1990). Poly-D-(-)-3-hydroxybutyrate (PHB), the most widespread and thoroughly characterized PHA, is a biodegradable and biocompatible thermoplastic.

Research on PHA production has been mainly concentrated on *Alcaligenes eutrophus* which produces short chain PHAs ($C_3$ to $C_5$ units). In *A. eutrophus*, PHB is synthesized from acetyl-CoA by the sequential action of three enzymes (FIG. 1) (Steinbüchel, A. and Schlegel, H. G., Mol. Microbiol. 5: 535–542, 1991). The first enzyme of the pathway, 3-ketothiolase (E. C. 2.3.1.9), catalyzes the reversible condensation of two acetyl-CoA moieties to form acetoacetyl-CoA. Acetoacetyl-CoA reductase (E.C. 1.1.1.36) subsequently reduces acetoacetyl-CoA to D-(-)-3-hydroxybutyryl-CoA, which is then polymerized by the action of PHB synthase to form PHB. PHB is produced as a polymer of $10^5$–$10^6$ monomer units which is accumulated in granules of 0.2 to 0.5 μm in diameter, each granule containing approximately 1000 polymer chains (Anderson, A. J. and Dawes, E. A., Microbiol. Rev. 54: 450–472, 1990). When grown in medium containing glucose, *A. eutrophus* typically accumulates PHB up to 80% dry weight. The genes encoding the three phb biosynthetic enzymes described above have been cloned from *A. eutrophus* (Peoples, O. P. and Sinskey, A. J., J. Biol. Chem. 264: 15293–15297, 1989 and J. Biol. Chem. 264: 15298–15303, 1989; Slater, S. C., Voige W. H. and Dennis, D. E., J. Bacteriol. 170: 4431–4436, 1988, Schubert, P., Steinbüchel, A. and Schlegel, H. G., J. Bacteriol. 170: 5837–5847, 1988).

In addition to PHB homopolymer, *A. eutrophus* and other bacterial species can produce polymers containing various ratios of a number of different $C_3$ to $C_5$ monomers. The nature and proportion of these monomers is influenced by the carbon source supplied in the growth media. For example, when propionic acid or pentanoic acid is supplied to the fermentation feedstock, a random copolymer containing both 3-hydroxybutyrate (3HB) and 3-hydroxyvalerate (3HV) monomers is produced with a maximum of 43 mol % to 90 mol % of 3HV unit, respectively (Anderson, A. J. and Dawes, E. A., Microbiol. Rev. 54: 450–472, 1990). These PHA copolymers are synthesized by the same PHB synthase using the coenzyme A thioester derivatives of the $C_3$ to $C_5$ organic acids.

In addition to PHB and copolymers containing PHB, there is another general class of PHAs containing monomer units ranging between $C_6$ and $C_{12}$. *Pseudomonas olevorans* is the prototypical bacterium synthesizing PHAs containing medium-chain (D)-3-hydroxyacids when n-alkanes or n-alkanoic acids are provided in the growth media. The best studied of these PHAs is polyhydroxyoctanoate, which is accumulated when *P. olevorans* is grown in a medium containing octanoate (Huisman, G. W., de Leeuw, O., Eggink, G., and Witholt, B. Appl. Environ. Microbiol. 54: 2924, 1988). Furthermore, unique polymers possessing unsaturated or branched chain monomers, as well as possessing chloride or fluoride side groups, can be obtained by manipulation of the fermentation feedstock (Doi, Y. (ed), In: Microbial polyesters, Chpt. 3, VCH Publisher, New York (1990).

PHB is a stiff and relatively brittle thermoplastic (Doi, Y. (ed) In: Microbial Polyesters, Chpt. 6, VCH Publishers, New York, 1990; Holmes, P. A. In: Developments in crystalline polymers-2. Basset, D. C. (ed), 1–65, 1988). Incorporation of 3HV monomers into the polymer leads to a decrease in crystalinity and melting point compared to PHB, resulting in a decrease in stiffness and an increase in toughness of the polymer, making P(3HB-co-3HV) and other related copolymers more suitable for many commercial applications. It is also possible to blend various polymers and plasticizers to PHB in order to improve its physical characteristics (Holmes, P. A. In: Developments in crystalline polymers-2. Basset, D. C. (ed), 1–65, 1988). PHB has good UV resistance but generally poor resistance to acids and bases as well as organic solvents. PHB possesses good oxygen impermeability and is resistant to hydrolytic degradation in moist air. These properties makes PHB attractive as a source of plastic for a wide range of commodity products, such as household containers, bags and wrapping films. In contrast to PHB, long-chain PHAs are elastomers with a melting point ranging from 40°–60° C. (Gross, R. A., De Mello, C., Lenz, R. W., Brandl, H. and Fuller R. C., Macromolecules 22: 1106, 1989). The physical properties of these PHAs have yet to be fully characterized.

PHB and related copolymers are readily degraded in soil, sludge and sea water. For example, in soil at 30° C., films of P(3HB-co-4HB) copolymer and PHB homopolymer are decomposed in two and ten weeks, respectively (Doi, Y. (ed) In: Microbial Polyesters, Chpt.1, VCH Publishers, New York, 1990). A number of bacteria and fungi were shown to be able to actively degrade these polymers (Dawes, E. A. and Senior, P. J., Adv. Microb. Physiol. 10:135–266 (1973).

Extracellular PHB depolymerases and hydrolases have been isolated from several bacteria, including *Alcaligenes feacalis*. PHB can thus be degraded to monomeric 3HB units which can be used as a source of carbon for bacterial and fungal growth. Furthermore, PHB is very biocompatible, making it potentially attractive for medical applications such as suture filaments and drug carriers (Koosha, F., Muller, R. H. and Davis, S. S. In: Critical reviews in therapeutic drug carrier system, 6: 117–129, 1989). Degradation of PHB produces D-3-hydroxybutyric acid, a metabolite normally present in blood. The biodegradation of PHB is an important aspect of its usefulness as a plastic for commodity disposable products, as well as for specialized uses such as in agricultural mulches or medical implants.

P(3HB-co-3HV) copolymer synthesized by *A. eutrophus* is produced industrially by Imperial Chemical Industries and marketed under the trademark BIOPOL. Estimated cost based on a production of 500000 kg of polymer a year is approximately $15 per kg, in contrast to approximately $1 per kg for petroleum-derived commodity plastics such as polypropylene (Poole, R, Science 245: 1187–1189, 1989). Two major contributors to the cost of production are the carbon source added to the feedstock (eg sucrose, glucose, propionate) and harvesting of the polymer from the bacteria. A number of strategies are being explored to reduce the production cost (Poirier, Y., Dennis, D. E., Nawrath, C. and Somerville, C. Adv. Mater. 5: 30–36, 1993). For example, some bacteria are able to produce PHB when grown on cheap unrefined sugar sources such as molasses and corn syrup. Some strains of Pseudomonas and Rhodococcus are able to produce a number of PHA copolymers when grown on glucose, thus avoiding the addition of expensive substrates, like propionate, normally required for copolymer production. Genetic engineering of bacteria, including the use of *E. coli* synthesizing PHB, is also expected to have an impact on production cost of PHB. However, despite these potential improvements, it is generally agreed that due to the inherent costs associated with bacterial fermentation and downstream processing, the cost of PHA produced by bacteria will probably not be lower than approximately $3–5 per kg. It is unlikely that it will ever be possible to produce bacterial biomass at a cost comparable to that of producing biomass from higher plants. For example, potato can yield approximately 20000 kg of starch per hectare, with the potato tuber accumulating starch up to 80% of its dry weight (Martin, J. H., Leonard, W. H. and Stamp, D. L. (eds), Chapter 36, In: Principles of Field Crop Production, 898–932, Macmillan, New York, 1976). Starch is one of the lowest priced (approximately $0.2 /kg) and most abundant worldwide commodities. Similarly, oil producing crops, such as rapeseed, produce 1000 kg of oil per hectare with seed oil content up to 44% dry weight (Downey, R. K. and Röbbelen, G., In: Oil crops of the world, Röbbelen, G., Downey, R. K. and Ashri, A. (eds), Chpt. 16, McGraw-Hill, New York, 1989). In addition to be highly productive, plants have been shown to be very effective in producing a number of biologically active foreign proteins, such as antibodies (Hiatt, A., Cafferkey, R. and Bowdish, K., Nature 342: 76–78, 1989). There is growing interest in making use of the high productivity and flexibility of plants to produce a variety of organic materials, including proteins and various other polymers (Moffat, A. S., Science 256: 770–771, 1992).

Production of poly D-(-)-3-hydroxybutyrate, one member in the family of PHAs, has previously been demonstrated in the higher plant *Arabidopsis thaliana* (Poirier, Y., Dennis, E., Klomparens, K. and Somerville, C., Science 256: 520–523, 1992 and patent application Ser. No. 07/732,243).

Of the three enzymes required to make PHB from acetyl-CoA, the 3-ketothiolase is endogenously present in plants. In the initial experiments, the genes from the bacterium Alcaligenes eutrophus encoding 3-ketothiolase (phbA), the acetoacetyl-CoA reductase (phbB) and the PHB synthase (phbC) were transferred and expressed in Arabidopsis under the transcriptional control of the constitutive CaMV 35S promoter (FIG. 1). In these experiments, the enzymes were targeted to the cytoplasm, because of the absence of organelle targeting signals on the gene products. Through appropriate genetic crosses, a hybrid plant was obtained which contained all of the enzymes required for PHB synthesis. Analysis of the chloroform-soluble compounds present in the hybrid plant by gas chromatography and mass spectrometry (GC-MS) revealed the presence of PHB. Between 20 to 100 µg of PHB per gram fresh weight of plant material could be detected. Examination by electron microscopy of thin sections of plant tissues producing PHB revealed the presence of agglomerations of electron-lucent granules. These granules were very similar in size and appearance to the granules found in *A. eutrophus* and other bacteria accumulating PHB. Surprisingly, PHB granules were found in various compartments, namely the nucleus, vacuole and cytoplasm. No PHB granules could be detected in the mitochondria or chloroplast. The basis for this distribution of granules is unknown.

The demonstration of PHB production in genetically engineered Arabidopsis plants revealed several problems. One of the problems is the low yield of PHB. A second problem is the adverse effect of the expression of the phb genes on plant growth. Expression of high amounts of acetoacetyl-CoA reductase activity in transgenic plants caused a significant reduction in growth and seed production relative to wild type plants. For example, in a transgenic line expressing approximately 9 units of acetoacetyl-CoA reductase activity per mg of protein (one unit being defined as one µmole of acetoacetyl-CoA reduced per min), the fresh weight of 22 day-old shoots was reduced to 19% of wild type (Poirier, Y., Dennis, D. E., Klomparens, K., Nawrath, C. and Somerville C., FEMS Microbiol. Lett., 103: 237–246, 1992). Seed production was reduced in approximately the same proportion. This phenotype could be the result of the diversion of a significant amount of acetyl-CoA and/or acetoacetyl-CoA away from essential biochemical pathways leading to a decrease in the production of compounds such as phytohormones, carotenoids, sterols, quinones, flavonoids, and lipids (FIG. 2). Alternatively, accumulation of a β-hydroxybutyryl-CoA, or of a product derived from it, may be deleterious to plant cells. The fate of D-β-hydroxybutyryl-CoA produced in transgenic plants is unknown. Expression of the PHB synthase, by itself, had no apparent effect on the growth or vigor of transgenic plants. However, hybrid plants containing both genes were more severely stunted in growth than plants containing only the acetoacetyl-CoA reductase activity. This could be due either to a more severe depletion of substrate from the mevalonate pathway or to a noxious effect of the PHB granules, particularly the granules being accumulated in the nucleus.

DESCRIPTION OF PREFERRED EMBODIMENTS

The present invention relates to a transgenic plant material having plastids, the plant material containing foreign DNA encoding a bacterial polypeptide which is selected from the group consisting of 3-ketothiolase, acetoacetyl-CoA reductase and polyhydroxyalkanoate (PHA) synthase and mixtures thereof leading to the production of a polyhydroxyalkanoate in the plastid in the plant.

The present invention also relates to a transgenic plant material having plastids, the plant material containing foreign DNA encoding a peptide which exhibits 3-ketothiolase activity in the plastid in the plant.

The present invention also relates to a transgenic plant material having plastids, the plant material containing foreign DNA encoding acetoacetyl-CoA reductase activity in the plastid of the plant.

The present invention also relates to a transgenic plant material having plastids, the plant material containing foreign DNA encoding a polypeptide which exhibits PHA synthase activity in the plastid of the plant.

The present invention also relates to a transgenic plant material having plastids, the plant material containing foreign DNA encoding one or more enzymes leading to the synthesis of polyhydroxyalkanoate (PHA) from hydroxyacyl-CoA in the plastid of the plant.

The present invention further relates to a transgenic plant material having plastids, the plant material containing foreign DNA encoding one or more enzymes which catalyze synthesis of hydroxyacyl-CoA in the plastid of the plant.

The present invention also relates to a transgenic plant having plastids, the plant material containing foreign DNA encoding one or more enzymes leading to production of acetoacetyl-CoA, from products encoded by the foreign DNA, in the plastid of the plant.

The present invention also relates to a transgenic plant material having plastids, the plant material containing foreign DNA encoding one or more enzymes leading to production of 3-hydroxybutyryl-CoA, from products encoded by the foreign DNA, in the plastid in the plant.

The present invention also relates to a method for introducing foreign DNA encoding polypeptides leading to the synthesis of a polyhydroxyalkanoate (PHA) in the plastid in a plant which comprises mating by sexual fertilization two plants which do not produce PHA, each containing foreign DNA from a bacterium encoding one or more different enzymes in a pathway leading to polymerization of hydroxyacyl-CoA by PHA synthase to produce the plant which synthesizes the PHA in a plastid of the plant.

OBJECTS

It is therefore an object of the present invention to provide one or more of the enzymes which lead to the accumulation of PHA, particularly PHB, in the plastid. It is further an object of the present invention to provide plants which exhibit good growth and seed formation. These and other objects will become increasingly apparent by reference to the following description and the drawings.

BRIEF DESCRIPTION OF DRAWINGS

FIGS. 3a, 3b, and 3c are schematic diagrams of the TPSS-phb gene fusions. FIG. 3a shows the TPSS-3-ketothiolase gene fusion, FIG. 3b shows the TPSS-acetoacetyl-CoA reductase gene fusion and FIG. 3c shows the TPSS-PHB synthase gene fusion. All of these constructs are composed of four distinct regions indicated in boxes, namely the 55 amino acid transit peptide and the first 23 amino acids of the mature protein encoded by the gene 3.6 of the small subunit of Rubisco of pea, a short linker sequence and the full coding region of the phbA (A), phbB (B) and phbC (C) genes of *A. eutrophus* with exception of the initial methionines. The amino acid sequences (single letter code) in bold and DNA sequences present at the junctions of each region are indicated. Stretches of amino acids between the junctions, indicated by hyphens, have previously been published (Cashmore, A. R. In: Genetic engineering of plants (ed. Kosuge, T., Meredith, C. P. and Hollaender, A.) 29–38, Plenum Press New York, 1983; Janes, B., Hollar, J and Dennis, D., E. A. Dawes (ed.), Novel Biodegradable Microbial Polymers 175–190 (1990)). The stars indicate termination codons. Endonuclease restriction sites which were introduced by PCR during subcloning procedures are indicated.

FIGS. 4A, 4B, and 4C show a more detailed description.

FIGS. 14A, 14B, and 14C show gas chromatography (GC) analysis of purified PHB and plant extracts. FIG. 14A is a gas chromatogram of transesterified PHB purchased from Sigma Chemical Company; FIG. 14B is a gas chromatogram of chloroform extracts of leaves from untransformed wild type A. thaliana race Rschew. The arrow shows the position where ethyl-hydroxybutyrate would elute from the chromatogram; FIG. 14C is a gas chromatogram of chloroform extracts of leaves from hybrid TPSS-Thio L/TPSS-Red DEF/TPSS-Syn GHI1. The arrow indicates the location of the ethyl-hydroxybutyrate peak.

FIG. 15A shows the mass spectrum of transesterified commercial PHB; FIG. 15B shows the mass spectrum of the GC peak from leaf chloroform extract of a TPSS-Thio L/TPSS-Red DEF/TPSS-Syn GHI1 hybrid having a retention time identical to ethyl-hydroxybutyrate (as shown in FIG. 14C).

FIG. 16A shows measurements made on expanding leaves (20–30 day-old); FIG. 16B shows measurements made on mature leaves (50–60 day-old).

FIG. 19A shows agglomeration of electron-translucent granules in the chloroplast of a mesophyll cell is indicated by the arrows. The plant was put in the dark for 48 h before sampling for EM analysis in order to remove the starch. Bar represent 1 µm. FIG. 19B shows a transmission electron micrograph of thin sections of wild type leaves collected after 4 hours of illumination in a 12 h photoperiod. Starch accumulation in the plastids in form of ovular singular granules are indicated by large arrows in wild type; FIG. 19C shows a transmission electron micrograph of thin sections of PHB-positive TPSS-Thio L/TPSS-Red DEF/TPSS-Syn GHI1 hybrid leaves collected after 4 hours of illumination in a 12 h photoperiod. Starch accumulation in the plastids in form of ovular singular granules are indicated by large arrows. Agglomerations of electron-lucent PHB granules in the plastid of the tri-hybrid are indicated by small arrows. Bars represent 1 µm.

Figure 1:
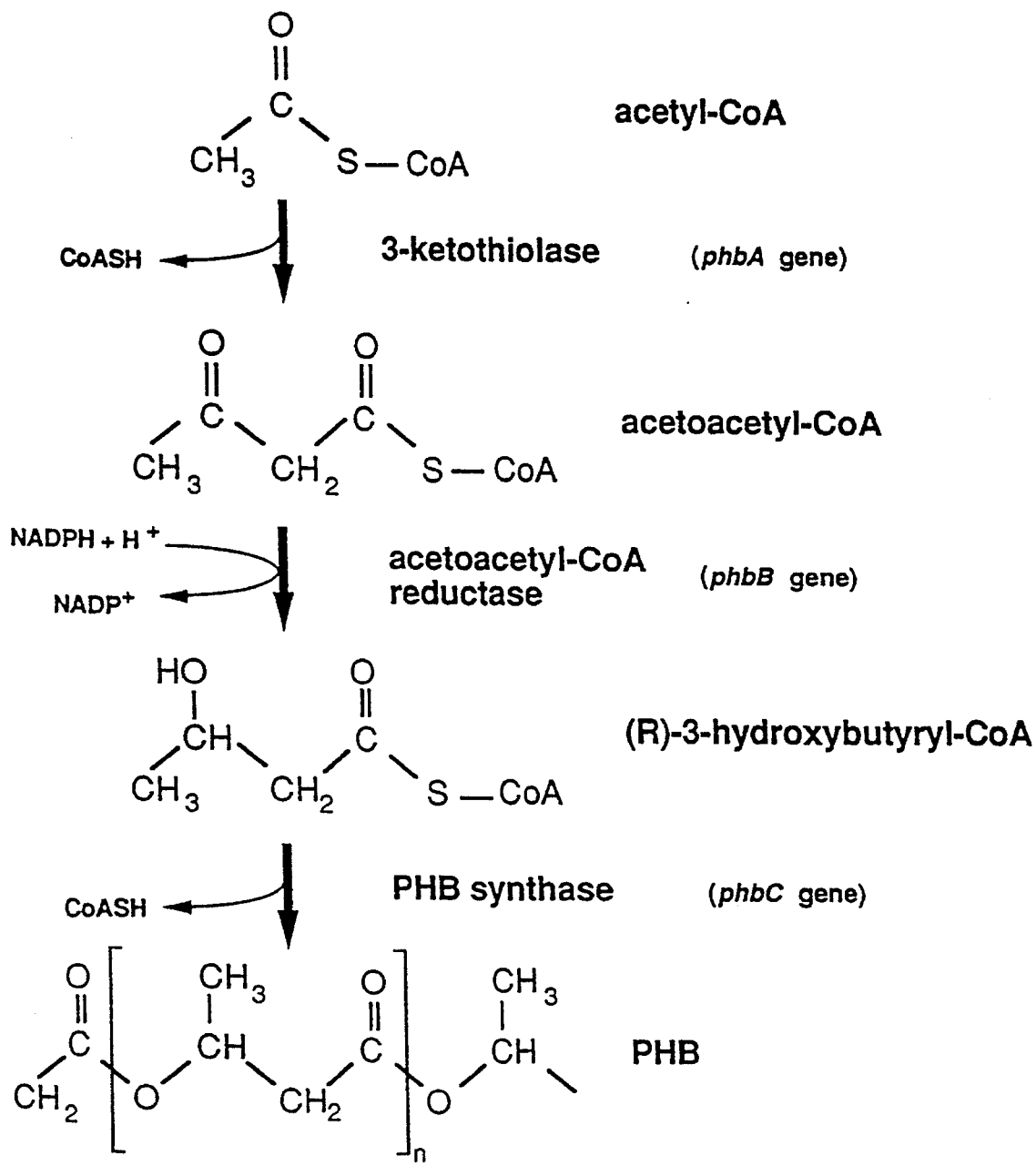
FIG. 1 is a flow diagram showing the pathway of PHB synthesis in *A. eutrophus*. The genes encoding the three enzymes are shown in parenthesis.
Figure 2:
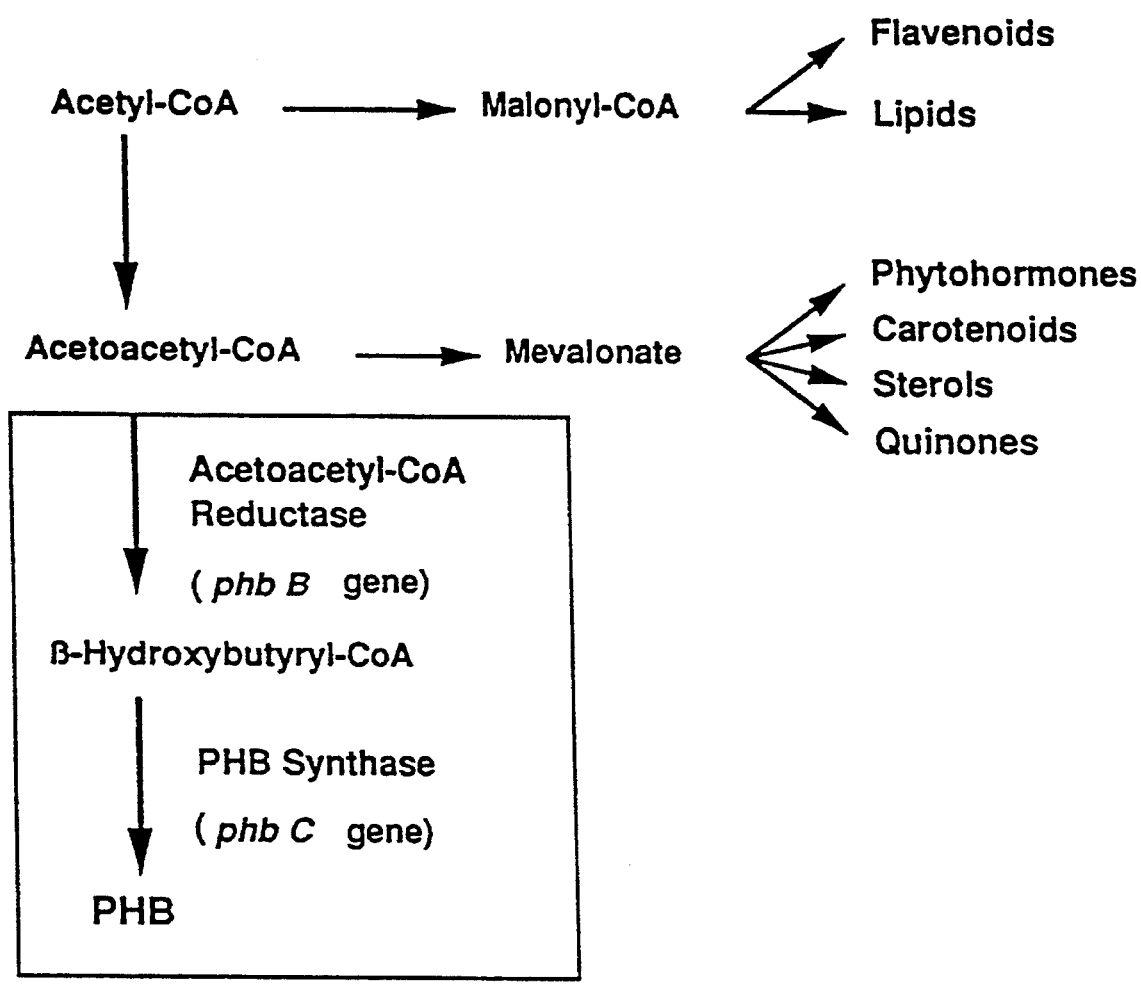
FIG. 2 is a flow diagram showing metabolic pathways utilizing acetyl-CoA and acetoacetyl-CoA in transgenic plants producing PHB. The major end products of endogenous plant metabolic pathways utilizing acetyl-CoA and acetoacetyl-CoA as precursors are shown in the upper part of the diagram. The additional pathway created in transgenic plants by the expression of the phbB and phbC genes from *A. eutrophus* is indicated in the box.

It is helpful to set forth definitions of certain terms to be used hereinafter.

Transformation means the process for changing the genotype of a recipient organism by the stable introduction of DNA by whatever means.

A transgenic plant is a plant which contains DNA sequences which are not normally present in the species, but were introduced by transformation.

Transcription means the formation of an RNA chain in accordance with the genetic information contained in the DNA.

Translation means the process whereby the genetic information in an mRNA molecule directs the order of specific amino acids during protein synthesis.

A promoter is a DNA fragment which causes transcription of genetic material. For the purposes described herein, promoter is used to denote DNA fragments that permit transcription in plant cells.

A poly-A addition site is a nucleotide sequence which causes certain enzymes to cleave mRNA at a specific site and to add a sequence of adenylic acid residues to the 3'-end of the mRNA.

phbC, phbA, phbB are the gene symbols given to the *A. eutrophus* genes for PHB polymerase, 3-ketothiolase and acetoacetyl-CoA reductase, respectively (Peoples, O. P. and Sinskey, A. J., J. Biol. Chem 264: 15298–15303, 1989).

A plastid is a self-replicating organelle which is located in multiple copies in the cytoplasm of different kinds of plant cells. This organelle is surrounded by a double layered membrane and contains its own DNA. Proteins located in the plastid are either encoded by its own DNA and synthesized in the plastid or are encoded by the nucleus of the plant cell, synthesized in the cytoplasm and transported into the plastid.

In describing the progeny of transgenic plants, it is useful to adopt a convention which designates how many generations of self-pollination have elapsed since the introduction of DNA. Herein, we designate the original transformant the T0 generation. The progeny resulting from self-pollination of this generation is designated the T1 generation and so on.

In the case of cross-pollination between two distinct parental plants, the resulting progeny from the initial cross-pollination event is designated the F1 generation.

The invention described in this disclosure concerns the alleviation of the growth disruption and low PHB production associated with the first generation of PHB producing plants by changing the cellular localization of the PHB biosynthetic enzymes and by regulating the tissue specificity and the timing of expression.

In order to both increase PHB production and avoid the potential depletion of essential products derived from acetyl-CoA and/or acetoacetyl-CoA, the bacterial PHB biosynthetic enzymes were targeted to a subcellular compartment having a high metabolic flux through acetyl-CoA and/or acetoacetyl-CoA, namely the plastid. Being the site of fatty acid synthesis in plants, the plastid has a high level of acetyl-CoA production (Harwood, J. L., Ann. Rev. Plant Physiol. Plant Mol. Biol. 39: 101–138, 1988). In storage tissues, diversion of some of this plastid acetyl-CoA away from fatty acid biosynthesis toward PHB production should not be deleterious to the growth of the plant. Starch, a high molecular weight biopolymer naturally synthesized in plants, accumulates to a high amount in the plastids of many storage tissues (amyloplasts) (Preiss, J., Ann. Rev. Plant Physiol. 33: 431–454, 1982). In photosynthetic chloroplasts, starch also accumulated transiently during the daily period of $CO_2$-fixation. The plastid is therefore a compartment which can vary its dimensions and has a large storage capacity. Thus, the accumulation of PHB in the plastid is not expected to interfere with the plastid function or cause some mechanical disruption. Furthermore, expression of the PHB biosynthetic pathway in the cytoplasm resulted in PHB granule accumulation in the cytoplasm, nucleus and vacuole, but not in the plastid (Poirier, Y., Dennis, E., Klomparens, K. and Somerville, C. Science 256: 520–523, 1992). This raises the possibility that the plastid envelope is impervious to penetration by PHB granules. Therefore, an added advantage of plastid PHB production is that PHB granules may accumulate and remain exclusively in the plastid, avoiding potential mechanical disruption of other organelles by the granules.

In the invention described here, the genes phbA, phbB and phbC from *Alcaligenes eutrophus* modified for plastid targeting of the encoded enzymes were introduced into plant cells. They were expressed under the transcriptional control of the CaMV 35S promoter, the same promoter which had been used previously to construct PHB producing plants. This approach allows a direct comparison of the plastid and cytoplasmic expression of the enzymes and of the PHB production levels.

In a second part of the invention described here, PHB production was restricted to a specific tissue and a specific stage of the plant life cycle to reduce the possibility of deleterious effects on the overall growth of the plants. Since the flux of acetyl-CoA in the plastids is particularly high in tissues which normally accumulate a large amount of oil, such as the seeds of an oil plant, the developing seed is a suitable tissue for the PHB production. The diversion of some of this acetyl-CoA away from fatty acid synthesis used for storage lipids towards PHB synthesis should not be deleterious for the growth of the plant. Therefore, the plastid targeted phb enzymes were expressed specifically in the developing seeds using the promoter of a seed storage protein gene of *Arabidopsis thaliana*.

PHA production on an agricultural scale requires that the PHA producing plants have normal vigor and that the level of PHA produced be above a certain minimum level which has not yet been reached in previous generations of transgenic plants. This invention is therefore of high importance for the successful development of PHA producing plants. Because of the close relationship of Arabidopsis and *Brassica napus*, the constructs described in the following sections could be directly used for PHB production in Brassica. In addition, because of the similarity in mechanisms of gene expression and primary carbon metabolism in different species of higher plants, it is also apparent that the essence of this invention, the production of PHA in plastids, is applicable to other plant species. The production of PHB in other oil-producing plants, such as the seeds of rape and sunflower or in the mesocarp of avocado or oilpalm, are particularly attractive since these plant organs are specialized on providing the precursor acetyl-CoA for fatty acid biosynthesis.

Although the experiments discussed hereinafter concern the plant species *Arabidopsis thaliana* (L.). The process described is generally applicable to any higher plant for which a method of transformation is available. Similarly, although the process described herein concerns the use of genes from *A. eutrophus*, the process described is generally applicable to the use of genes from any organism which is capable of synthesis of PHB. It is also clear that, although the process described concerns the production of PHB, the procedure is generally applicable to the production of any polyhydroxyalkanoate which is normally produced in microorganisms by the activity of PHA synthase (which includes PHB synthase), and for which the appropriate hydroxyacyl-CoA substrate is produced in the particular plant.

The production of PHB in the plastids in transgenic plants requires the completion of a sequence of steps as follows: 1.) the construction of one or more plasmids containing fusions of the bacterial genes for PHB synthesis to plastid targeting sequences expressed under the control of a plant promoter in *E. coli*, 2.) the introduction of these plasmids into *Agrobacterium tumefaciens* 3.) the infection of plants with the transformed *Agrobacterium tumefaciens* in order to transform plant cells with the modified genes (i.e., *A. thaliana* in this example) 4.) the selection of plants transformed with the modified genes, 5.) the selection of plants which are homozygous for the ectopic genes, 6.) analysis of the transformed plants concerning integration of the plasmid and the expression of the ectopic genes to ensure that they are active and that the gene products are targeted to the plastid, processed and functional, 7.) the production of hybrid plants containing two or more different ectopic genes by sexual crosses, 8.) the analysis of the hybrid material for the presence of PHB.

1. Construction of the plasmids containing the plastid targeting sequence—phb gene fusions under the control of a plant promoter in *E. coli*.
1. 1. Fusion of a Signal Sequence to the Coding Regions of the phb Genes.

In order to target a protein to the stroma of the plastid in plant cells, the protein must contain a transit peptide at its N-terminal end (Keegstra, K. and Olsen, L. J., Annu. Rev. Plant Physiol. Plant Mol. Biol, 40: 471–501, 1989; Archer, E. K. and Keegstra, K., J. Bioenerg. Biomem., 22: 789–810, 1990). Therefore, a signal sequence encoding the transit peptide has to be fused in the correct reading frame to the 5' end of the coding sequence of the protein. The transit peptide of the small subunit of the ribulose 1–5 bisphosphate carboxylase (rubisco) (TPSS) has been well characterized (Robinson, C. and Ellis, R. J., Eur. J. Biochem, 142: 343–346, 1984, Wasmann, C. C., Reiss, B., Barlett, S. G., and Bohnert, H. J., Mol. Gen. Genet. 205: 446–453, 1986; Friedmann, A. L. and Keegstra, K., Plant Physiol. 89: 993–999, 1988; Lubben, T. H., Gatenby, A. A., Ahlquist, P., and Keegstra, K., Plant Mol. Biol. 12: 13–18, 1989; Schnell, D. J., Blobel, G., and Pain, D., J. Biol. Chem. 266: 3335–3342, 1991) and has been previously used successfully in a number of targeting experiments (van de Broeck, G., Timko, M. P., Kausch, A. P., Cashmore, A. R., Van Montagu, M. and Herrera-Estrella, L., Nature 313: 358–363, 1985; Schreier, P. H., Seftor, E. A., Schell, J., and Bohnert, H. J., EMBO J. 4: 25–32, 1985; Boutry, M., Nagy, F., Poulsen, C., Aoyagi, K., and Chua N.-H., Nature 328: 340–342, 1987; Lubben, T. H., and Keegstra, K., Proc. Natl. Acad. Sci 83: 5502–5506, 1986; Lamppa, G. K., J. Biol. Chem, 263: 14996–14999, 1988; Gatenby, A. A., Lubben, T. H., Ahlquist, P., and Keegstra, K., EMBO J. 7: 1307–1314, 1988; Cheung, A. Y., Bogorad, L., Van Montagu, M., and Schell, J., Proc. Natl. Acad. Sci. 85: 391–395, 1988; Lubben, T. H., Theg, S. M. and Keegstra, K., Photosyn. Res. 17: 173–194, 1988). The TPSS of pea was therefore used in the following experiments. However, a number of different transit peptides involved in plastid targeting could also be used in an analogous way.

Since the transit peptide is normally cleaved off during the import into the plastid, the 3-dimensional structure at the junction between the transit peptide and the protein may be important for the efficiency of the transport (Wasmann, C. C., Reiss, B., Barlett, S. G., and Bohnert, H. J., Mol. Gen. Genet. 205: 446–453, 1986; Lubben, T. H., Gatenby, A. A., Ahlquist, P., and Keegstra, K., Plant Mol. Biol. 12: 13–18, 1989). Therefore, the sequence of the gene encoding the first 23 amino acids of the mature small subunit of rubisco was included in the transit peptide, which was fused to the bacterial genes of *A. eutrophus* involved in PHB production, namely the phbA, phbB and phbC genes.

To obtain the exact fusion between the signal sequences and the bacterial genes, the sequences coding for the TPSS as well as phb genes were amplified by polymerase chain reaction (PCR) using oligonucleotide primers which created new synthetic restriction sites at either end of the sequence. The primers designed for amplification are presented in Table 1.

TABLE 1

| | PCR-amplifications | | | |
|---|---|---|---|---|
| | Oligonucleotide | introduced site[a] | DNA source | fragment size[b] |
| phbA gene | | | | |
| 5' side | 5' CATCCCGGGTGATGACGTTGTCATC 3' | SmaI | pUC-Thio[c] | 1.3 kb |
| 3' side | 5' GAATTCGAGCTCGGTACCCTGAGTC 3' | SacI | | |
| phbB gene | | | | |
| 5' side | 5' AATCCCGGGTGACTCAGCGCATTGCG 3' | SmaI | pUC-Red[c] | 0.8 kb |
| 3' side | 5' GAATTCGAGCTCGGTACCGCGGCTGC 3' | SacI | | |

TABLE 1-continued

| | PCR-amplifications | | | |
|---|---|---|---|---|
| Oligonucleotide | | introduced site[a] | DNA source | fragment size[b] |
| phbC gene | | | | |
| 5' side | 5' AATCCCGGGTGGCGACCGGCAAAGGC 3' | SmaI | pUC-Syn[c] | 1.9 kb |
| 3' side | 5' CTACCCGGGAAGCGTCATGCCTTGGC 3' | SmaI | | |
| TPSS cod. region | | | | |
| 5' side | 5' CCGTCTAGAATGGCTTCTATGATATCCT 3' | XbaI | TPSSNPTII[d] | 0.27 kb |
| 3' side | 3' GCACCCGGGAATCTCTGGTCAATGGTGG 5' | SmaI | | |
| CRB promoter | | | | |
| 5' side | 5' CTCTCTAGAAGTGGAAGCACTCGAG 3' | XbaI | nAt4011[e] | 1.1 kb |
| 3' side | 5' CGGTCTAGATCCTCTTTATTGATTTACT 3' | XbaI | | |

[a])Restriction site introduced using the oligonucleotide for PCR reaction.
[b])Size of the amplified DNA fragment using the oligonucleotides and DNA source.
[c])Somerville, C. R., Poirier, Y. and Dennis, D. E., patent application ser. no. 07/732,243.
[d])Wasmann, C. C., Reiss, B., Barlett, S. G., and Bohnert, H. J., Mol. Gen. Genet. 205: 446–453, 1986.
[e])Pang, P. P., Pruitt, R. E. and Meyerowitz, E. M., Plant Mol. Biol. 11: 805–820, 1988.

Table 1 also includes the source of the DNA from which the fragments were amplified and the size of the amplified fragment. The PCR fragments were purified, cleaved with enzymes recognizing the introduced restriction sites and separated by agarose gel electrophoresis.

The purified 0.27 kbp XbaI-SmaI fragment containing the DNA fragment of the signal sequence was ligated to the vector pUC18 cleaved with the same restriction enzymes to produce the plasmid pUC-TPSS.

The purified 1.3 kbp SmaI-SacI fragment of the phbA gene and the 0.8 kbp fragment of the phbB genes were ligated into the SmaI and SacI cut pUC-TPSS plasmid to create the plasmids pUC-TPSS-Thio and pUC-TPSS-Red. The 1.9 kbp SmaI fragment of the phbC gene was ligated to pUC-TPSS cut with SmaI. A clone in which the synthase was cloned in the correct orientation behind the signal sequence was selected and designated pUC-TPSS-Syn.

In summary, each of the created plasmids, namely pUC-TPSS-Thio, pUC-TPSS-Red and pUC-TPSS-Syn, contains a part of a coding region of a plant gene and of a bacterial gene fused together in a way that they code for one synthetic polypeptide. At the junction between the plant and the bacterial sequence a synthetic sequence was formed coding for the three amino acids serine-arginine-valine (S-R-V). The amino acid and DNA sequences present at the junctions between the signal sequences and the bacterial genes are shown in FIG. 3. When expressed in a plant cell, these polypeptides are expected to be recognized by the protein import machinery of the plastids and transported to the stroma of the plastids.

1. 2. Addition of a Plant Promoter Upstream of the Modified phb Genes.

In order to obtain transcription of synthetic coding regions in higher plants, coding regions have to be under the control of a plant promoter located near the 5' end of the coding region. In addition, it is common practice to add a polyadenylation site to the 3' end of the coding region in order to ensure proper expression of the gene in higher plants. Furthermore, for the selection of transformed plants, a gene has to be present which enables only transformed plants to survive under selecting conditions. Such a gene is called a selectable marker. Two different promoters were used to express the modified phb genes: the CaMV 35S promoter and the CRB promoter.

The CaMV35S promoter (from cauliflower mosaic virus) is regarded as a constitutive promoter which results in relatively high levels of transcription in a wide variety of tissues in many species of higher plants (Benfey, P. N. and Chua, N.-H., Science 250: 959–966, 1990). In contrast, the CRB promoter isolated from the CRB gene of the 12S seed storage protein of *Arabidopsis thaliana* promotes high levels of transcription almost exclusively in the embryo of developing seeds (Pang, P. P., Pruitt, R. E., and Meyerowitz, E. M., Plant Mol. Biol. 11: 805–820, 1988).

1.2.1. Addition of the CaMV 35S Promoter Upstream of the Modified phb Genes.

In order to place the CaMV 35S promoter upstream of the modified phbA, phbB and phbC genes and to fulfill the other requirements for the expression of a coding region in higher plants, the plasmid vector pBI121 (Clonetech, Calif.) was used. This vector contains the neomycin II phosphotransferase gene as a selectable marker.

Figure 4A:
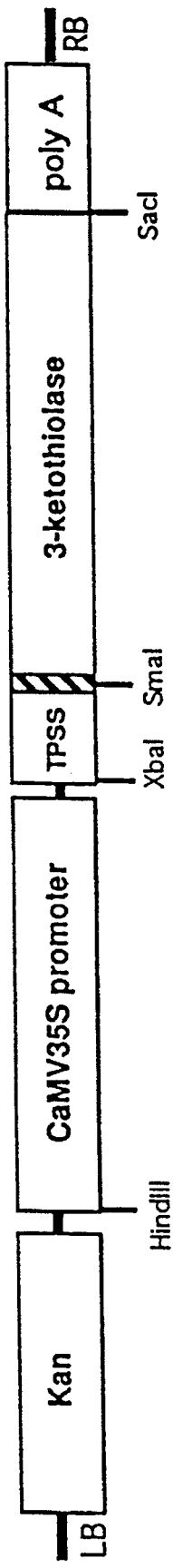
FIGS. 4A, 4B, and 4C are schematic diagrams of the Ti-plasmids harboring the CaMV 35S promoter and TPSS-phb gene fusion. Maps of pBI-TPSS-Thio, pBI-TPSS-Red and pBI-TPSS-Syn are shown in FIGS. 4A, 4B, and 4C. The physical components of each constructs are, from left to right: LB, left border sequence; Kan, neomycin phosphotransferase II gene; CaMV-35S, cauliflower mosaic virus 35S promoter; TPSS, transit peptide of the small subunit (3.6 gene) of Rubisco of pea; hatch box, synthetic linker; 3-ketothiolase gene (in FIG. 4A), acetoacetyl-CoA reductase gene (in FIG. 4B), or PHB synthase gene (in FIG. 4C); poly A, polyadenylation site; RB, right border sequence. The locations of important endonuclease restriction sites are indicated.
Figure 4B:
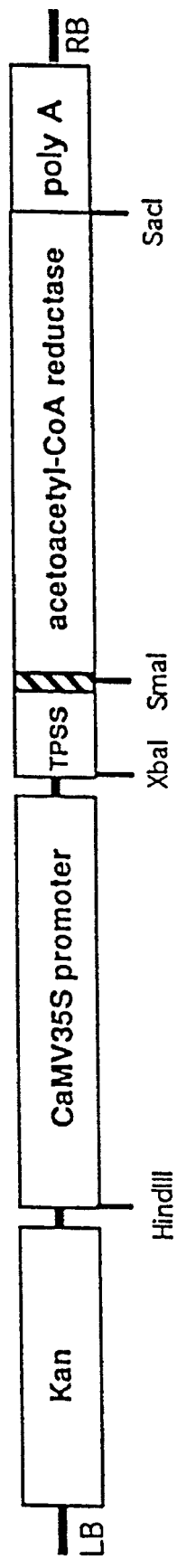

To construct the CaMV 35S-TPSS-phbA and the CaMV 35S-TPSS-phbB gene fusions, the plasmids pUC-TPSS-Thio and pUC-TPSS-Red were digested with the restriction enzymes XbaI and SacI. The 1.6 kbp restriction fragment from pUC-TPSS-Thio and the 1.1 kbp fragment from pUC-TPSS-Red were separated from the other fragments by agarose gel electrophoresis. The purified DNA fragments were ligated to pBI121 cleaved with the same enzymes and cloned into *E. coli*. The newly created plasmids pBI-TPSS-Thio and pBI-TPSS-Red contain the phbA gene and the phbB gene, respectively, modified for plastid targeting and located downstream of a plant promoter (FIGS. 4A and 4B).

Figure 4C:
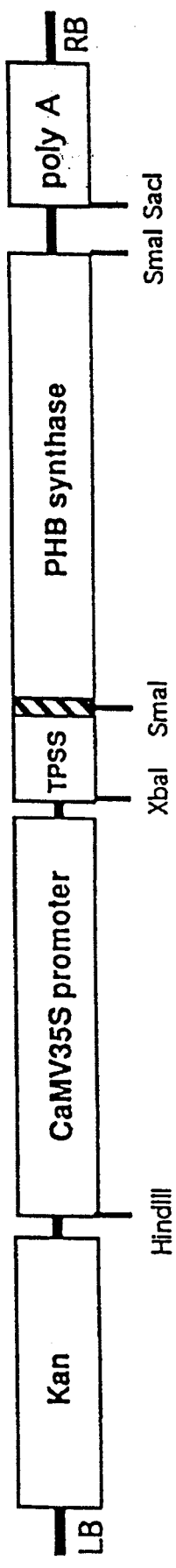

To construct the CaMV 35S-TPSS-phbC gene fusion, the plasmid pUC-TPSS-Syn was digested with EcoRI and the staggered ends were filled by T4 DNA polymerase. The plasmid was subsequently digested with XbaI. A 2.2 kbp DNA fragment was separated from other fragments by agarose gel electrophoresis. The purified DNA fragment was cloned into pBI121 cleaved by the restriction enzyme SmaI/XbaI. The resulting plasmid, designated pBI-TPSS-Syn (FIG. 4C), has the phbC gene from *A. eutrophus* modified for plastid targeting cloned in the right orientation, relative to the CaMV promoter and the polyadenylation site of pBI121, so that it is expected to be expressed in higher plants.

These constructs are expected to satisfy all requirements for high expression of the genes and targeting of the corresponding proteins, namely the modified 3-ketothiolase, the modified acetoacetyl-CoA reductase and the modified phb synthase, to the stroma of the plastid.

1.2.2. Addition of the Seed Specific Promoter Upstream of the Modified phb Genes.

For cloning of the modified phb coding regions downstream of the CRB promoter, the pBIB vectors (Becker, D., Nucleic Acids Res. 18: 203, 1990) were used. These vectors contain all functions that are needed for plant transformation. There are two versions of the vector: pBIB-Kan carries the neomycin II phosphotransferase gene as selectable marker, pBIB-Hyg the hygromycin phosphotransferase gene.

In order to simplify the subsequent cloning procedure, the CRB promoter had to be slightly modified by the removal of the XbaI restriction site at position −993. Therefore the plasmid nat4011 (Pang P. P., Pruitt, R. E. and Meyerowitz, E. M., Plant Mol. Biol. 11: 805–820, 1988) was digested with BamHI and EcoRI and after purification the 3.5 kbp fragment was cloned into pBR322 (Bolivar, F., Rodriguez, R. L., Greene, P. J., Betlach, M. C., Heyneker, H. L. and Boyer, H. W., Gene 2: 95–113, 1977) to produce pBR322-CRB. After cutting the single XbaI site of pBR322-CRB, the staggered ends were filled in with deoxyribonucleotides by incubation with T4 DNA polymerase, and the plasmid was religated. The resulting plasmid contained no XbaI site in the CRB promoter region.

In order to obtain the CRB promoter with suitable restriction sites at either end of the sequence, a polymerase chain reaction was performed by using oligonucleotide primers indicated in Table 1. The 1.1 kbp XbaI fragment was cloned into pK19 (Pridmore, R. D., Gene 56: 309–312, 1987) to create pK-CRB.

Figure 5A:
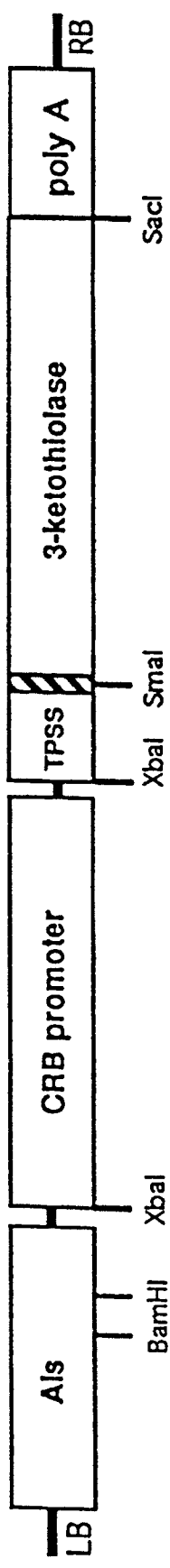
FIGS. 5A, 5B, and 5C are schematic diagrams of the Ti plasmids harboring the seed specific promoter and TPSS-phb gene fusion. Maps of pBIB-CCN-Thio, pBIB-KCN-Red, and pBIB-HCN-Syn are shown in FIGS. 5A, 5B and 5C. For all the constructs, the seed specific promoter of the CRB gene of the 12S seed storage protein of *A. thaliana* was placed upstream of the TPSS-phb gene fusion. The following selectable marker were used: ALS encoding for acetolactate synthase (FIG. 5A), Kan, encoding for Neomycin phosphostransferase II; Hyg, Hygromycin phosphotransferase.

In order to clone the TPSS-phbA coding region behind the CRB promoter, the plasmid pUC-TPSS-Thio was digested with the restriction enzymes XbaI and SacI and the 1.6 kbp DNA fragment was purified by agarose gel electrophoresis. This fragment was ligated to the vector pBIB-Hyg cleaved by XbaI and SacI. Since it would be very useful to have a different selectable marker combined with each of the three phb genes, the hygromycin II phosphotransferase gene of the pBIB-Hyg vector was subsequently replaced by the acetolactate synthase gene, which confers chlorsulforon resistance to transformed plants (Haughn, G. W., Smith, J., Mazur, B. and Somerville C. R., Mol. Gen. Genet. 211: 266–271, 1988). To do this, the resulting plasmid was cleaved by HindIII and BamHI to remove the hygromycin II phosphotransferase gene. The staggered ends of the plasmid were filled with deoxyribonucleotides by T4 DNA polymerase. The purified 5.8 kbp XbaI fragment from the plasmid pGH1 (Haughn, G. W., Smith, J., Mazur, B. and Somerville C. R., Mol. Gen. Genet. 211: 266–271, 1988) was subsequently inserted in the prepared plasmid. The resulting construct was designated as pBIB-C-TPSS-Thio. The CRB promoter was then added to the construct by cloning the 1.1 kbp long XbaI fragment of pK-CRB into the unique XbaI site of pBIB-C-TPSS-Thio. A clone containing the promoter in the right orientation for proper expression of the modified phbA was designated as pBIB-CCN-Thio (FIG. 5A).

Figure 5B:
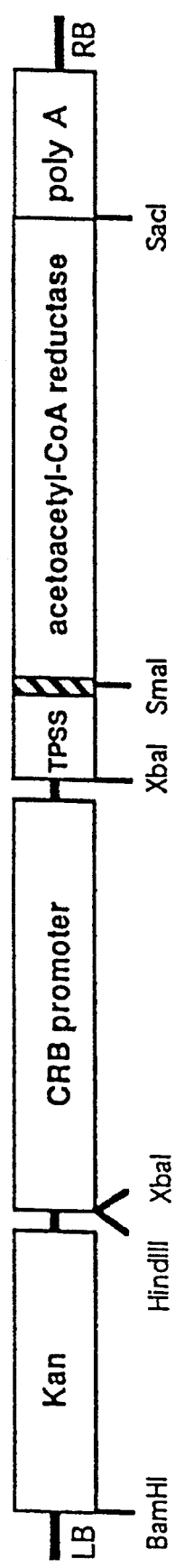

In order to clone the TPSS-phbB coding region behind the CRB promoter, the plasmid pUC-TPSS-Red was digested with XbaI and the 1.1 kbp XbaI fragment of the plasmid pK-CRB was inserted. A clone with the promoter in the right orientation was selected and designated as pK-CN-Red. The plasmid pK-CN-Red was digested with EcoRI and PstI to obtain the promoter/gene fragment and the ends were filled in with deoxyribonucleotides by T4 DNA polymerase. The 2.2 kbp fragment was purified by agarose gel electrophoresis and ligated in the vector pBIB-Kan digested with SmaI. A clone having the fragment in the right orientation for a proper gene expression in plants was named pBIB-KCN-Red (FIG. 5B).

Figure 5C:
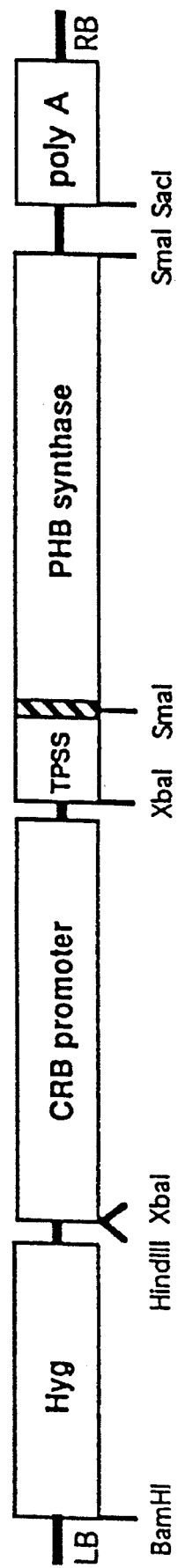

In order to clone the TPSS-phbC coding region behind the CRB promoter in the pBIB-Hyg vector, the plasmid pUC-TPSS-Syn was digested with EcoRI, the staggered ends were filled by T4 DNA polymerase and the linearized plasmid was subsequently cut with XbaI. A 2.2 kbp DNA fragment was separated from other fragments by agarose gel electrophoresis. The purified DNA fragment was cloned into pBIB-Hyg digested with the restriction enzymes XbaI and SmaI. In this resulting plasmid digested with XbaI, the 1.1 kbp XbaI fragment containing the CRB promoter obtained by cleaving the plasmid pk-CRB was cloned. A clone which had the promoter in the right orientation for a proper expression of the modified phbC gene was designated as pBIB-HCN-Syn (FIG. 5C).

In summary, the plasmids pBIB-CCN-Thio, pBIB-KCN-Red, pBIB-HCN-Syn are constructed such that when transformed into plants, the modified genes will be specifically expressed in the developing seeds with the proteins being targeted to the stroma of a plastid in the seed.

2. Introduction of the Constructs into *Agrobacterium tumefaciens*.

To enable the use of a plant transformation method which is mediated by *Agrobacterium tumefaciens*, the plasmids of both series of constructs were transferred into *Agrobacterium tumefaciens* strain pGV3101 by electroporation (Koncz, C. and Schell, J., Mol. Gen. Genet. 204: 383–396, 1986; Sambrook, J. Fritsch, E. F. and Maniatis, T. Molecular cloning, a laboratory manual, Cold Spring Harbor Laboratory Press, 1989). Bacterial colonies transformed with the various plasmids were recovered by selection for bacterial expression of the kanamycin resistance gene present on the plasmid pBI121 and pBIB.

3. Transformation of Plant Cells with *Agrobacterium tumefaciens*.

In the disclosed experiments, *Arabidopsis thaliana* was used as a model plant to show PHB production in the plastid. *A. thaliana* can be transformed by a *Agrobacterium tumefaciens* mediated meristem transformation method (Chang, S. S., Perk, S. K. and Nam, H.-G., Abstract in: Fourth International Conference on Arabidopsis Research, Vienna, 1990).

*Arabidopsis thaliana* race Rschew plants were grown under continuous light until the plants started bolting (approximately 3 weeks). The bolts (approx. 2 cm) were removed at their base together with the auxiliary buds. The wounded site was infected by Agrobacterium carrying the desired plasmid. Plants were grown until new bolts raised (approx. 1 week). Again the bolts were removed and the wounded site was infected with Agrobacterium. The plants were grown to full maturity and the seeds were harvested.

4. Selection of Transformed Plants.

Transformed T0 plants were selected by distributing the seeds obtained from the plants infected with the various Agrobacterium strains on agar-solidified plant medium containing the appropriate selection compound. For the selection of transformed plants carrying the T-DNA of pBI-TPSS-Thio, -Red and -Syn and of pBIB-KCN-Red, 50 µg/ml Kanamycin was added to the medium. For the selection of transformed plants carrying the T-DNA of pBIB-CCN-Thio, 30 ng/ml Chlorsulforon was added to the medium and 30 µg/ml Hygromycin for the selection of plants carrying pBIB-HCN-Syn. The above concentrations of the selection compounds prevent the growth of untransformed *A. thaliana* but permit normal growth of transformed plants. On average, from the seeds of approx. 40 plants infected with Agrobacterium one putative transformant could be isolated. Kanamycin resistant plants were designated with a letter/number combination.

A total of 14 kanamycin-resistant plants were recovered from seeds of plants which were infected with *A. tumefaciens* carrying the plasmid pBI-TPSS-Thio. These were designated TPSS-Thio GHI1, -GHI2, -GHI3, -GHI4, -L, -STU1, -STU2, -STU3, -STU4, -STU5, -STU6, -YZAA1, -YZAA2 and -YZAA3.

A total of 10 kanamycin-resistant plant lines were recovered from seeds of plants which were infected with *A. tumefaciens* carrying pBI-TPSS-Red. These were designated TPSS-Red DEF, -GHI1, -GHI2, -MNO 1, -MNO 2, -P1, -P2, -QR, -STU, -VWX.

A total of 6 kanamycin-resistant plant lines were recovered from seeds of plants which were infected with *A. tumefaciens* carrying the plasmid pBI-TPSS-Syn. These were designated TPSS-Syn-ABC, -GHI1, -GHI2, -JKL, -PQR, -VWX.

A total of two chlorsulforon resistant plants were recovered from seeds of plants which were infected with *A. tumefaciens* carrying the plasmid pBIB-CCN-Thio. These were designated CN-Thio 13-3 and -14-1.

A total of 6 kanamycin-resistant plants were recovered from seeds of plants which were infected with *A. tumefaciens* carrying the plasmid pBIB-KCN-Red. These were designated CN-Red 17-1, -17-3, -17-1dA, -17-1dB, -17-2K, -17-3K.

A total of 17 hygromycin-resistant plants were recovered from seeds of plants which were infected with *A. tumefaciens* carrying the plasmid pBIB-HCN-Syn. These were designated CN-Syn 34-1bA, -34-1bB, -34-2 A, -34-2B, -34-1 Ha, -34-1 Hb, -34-1 Hc, -34-1G1, -34-1G2, -35-1, -351aA, -35-1aB, -35-2A, -35-2B, -35-2C, -35-3, -35-1G1.

5. Isolation of Putative Homozygous Transgenic Lines.

A minimum criterion used to produce homozygous transgenic lines was that all the progeny from an homozygous plant are expected to be resistant to the selection marker. Because the presence of multiple ectopic copies of the inserted T-DNA at different locations in the genome may cause a similar phenotype, this criterion is most useful when the primary transformation event involves insertion of T-DNA into only one chromosomal location.

In order to identify putative homozygous lines, the resistant T0 plants were grown to maturity in reproductive isolation. Subsequently several T1 plants shown to be resistant to the selection medium were again grown to maturity. The frequency of resistance to the selectable marker was then determined in samples of approximately 100 T2 seeds from each line. If all of the T2 seeds from a particular plant were resistant to the selectable marker, the line was provisionally considered to be homozygous.

6. Analysis of the Transgenic Plants Obtained.
6.1. Analysis of the Expression and the Plastid Targeting of the phb Enzymes and their Targeting to the Plastid. 6.1.1. Analysis of Putative Transgenic Plants Obtained After Transformation with pBI-TPSS-Thio, pBI-TPSS-Red and pBI-TPSS-Syn.

In order to determine whether the transgenic plants transformed with pBI-TPSS-Thio, pBI-TPSS-Red and pBI-TPSS-Syn produced functional enzymes located in the chloroplasts, proteins of the kanamycin resistant transgenic plants were analyzed by Western blot analysis. Western blots of proteins of transgenic plants transformed with pBI-TPSS-Thio were incubated with antibodies raised against the 3-ketothiolase of *A. eutrophus*. Western blots of proteins of transgenic plants transformed with pBI-TPSS-Red were incubated with antibodies raised against the acetoacetyl-CoA reductase and the proteins of transgenic plants transformed with pBI-TPSS-Syn were incubated with polyclonal antibodies from rabbits raised against the PHB synthase. As a negative control, an analysis of a protein extract of a transgenic plant not containing the putatively produced enzyme was included in the analysis. As a positive control, an extract of a transgenic plant producing the enzyme in the cytoplasm was included.

Figure 6:
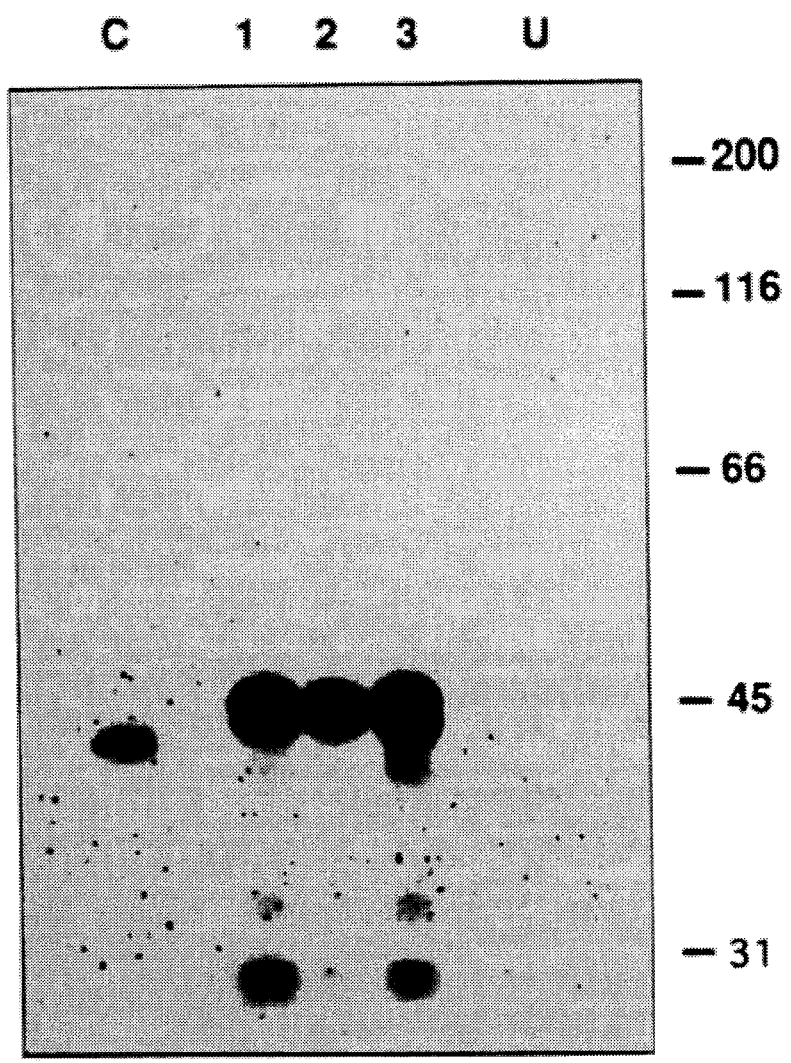
FIG. 6 is an autoradiograph of a Western blot analysis of transgenic *A. thaliana* plants expressing the plasmid pBI-TPSS-Thio and control plants. Aliquots of crude leaf protein extracts containing 1.2 μg protein were separated on a 10% SDS-PAGE. Proteins electroblotted on nitrocellulose were incubated with anti-3-ketothiolase antibody. Protein extracts analyzed were T4-3A (lane C; Somerville, C. R., Poirier, Y., and Dennis, D. E., patent application Ser. No. 07/732,243), TPSS-Thio GHI 1 (lane 1), TPSS-Thio L (lane 2), TPSS-Thio STU4 (lane 3), and TPSS-Red STU (lane U).

Of the 14 putative transgenic plants transformed with the pBI-TPSS-Thio, the protein extracts of the 3 plants, namely TPSS-Thio GHI1, -L and -STU4 showed a strong signal for the production of the 3-ketothiolase (FIG. 6). The enzyme appeared on the Western blot as a triplet of 45, 46.5 and 48 kDa bands. These bands represent the correctly processed protein and imprecisely processed products. The unmodified 3-ketothiolase located in the cytoplasm appears at 44 kDa. Therefore, the chloroplast targeted, correctly processed TPSS-3-ketothiolase is expected to have a molecular weight of ca. 47 kDa, because of the 23 amino acids added from the rubisco small subunit. The unprocessed protein, still harboring the entire transit peptide would have a molecular weight of ca. 53 kDa.

Figure 7:
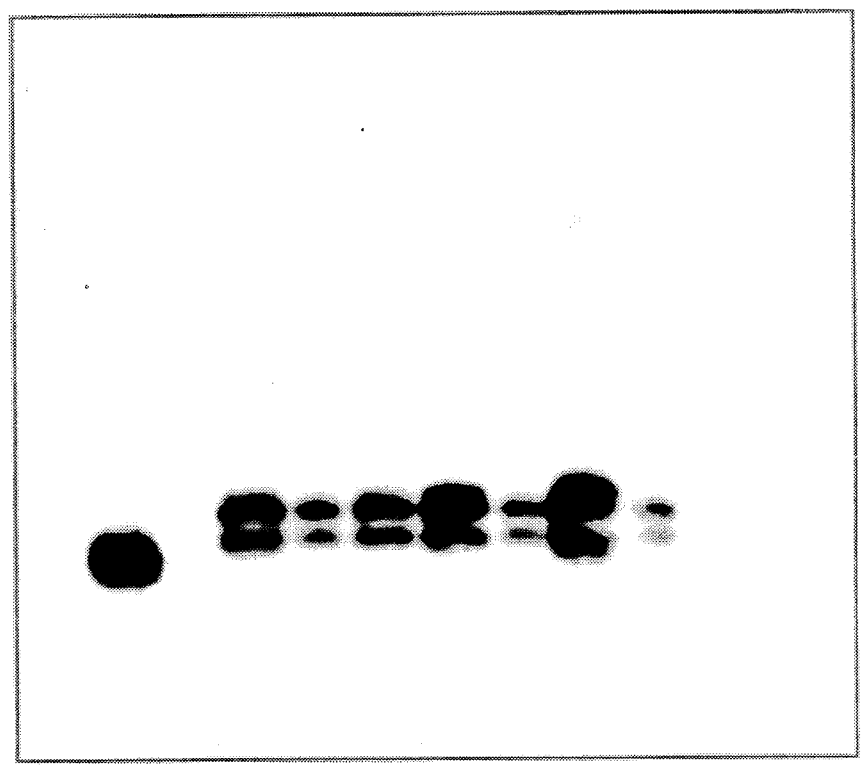
FIG. 7 is an autoradiograph of a Western blot analysis of transgenic *A. thaliana* plants expressing the plasmid pBI-TPSS-Red and control plants. Aliquots of crude leaf protein extracts containing 1.2 μg protein were separated on a 12% SDS-PAGE. Proteins electroblotted on nitrocellulose were incubated with anti-acetoacetyl-CoA reductase antibody. Protein extracts analyzed were RedB-2B (lane C; Somerville, C. R., Poirier, Y., and Dennis, D. E., patent application Ser. No. 07/732,243), TPSS-Red DEF (lane 1), TPSS-Red GHI1 (lane 2), TPSS-Red GHI2 (lane 3), TPSS-Red MNO1 (lane 4), TPSS-Red MNO2 (lane 5), TPSS-Red STU (lane 6), TPSS-Red VXY (lane 7), and TPSS-Syn VXY (lane U).

Of the 10 putative transgenic plants transformed with pBI-TPSS-Red, all plants except P1 and P2 showed a signal for the production of the acetoacetyl-CoA reductase. The intensity of these signals varied and was the strongest in TPSS-Red-DEF and -STU (FIG. 7). The signal appeared always as a triplet of 28.5, 29.0 and 30.5 kDa bands representing the correctly processed and imprecisely processed forms of the protein. The unmodified protein migrates at 26.5 kDa. Therefore, an unprocessed TPSS-acetoacetyl-CoA reductase would be expected to have a molecular weight of 35 kDa and a correctly processed form of the protein would have a molecular weight of about 29 kDa.

Figure 8:
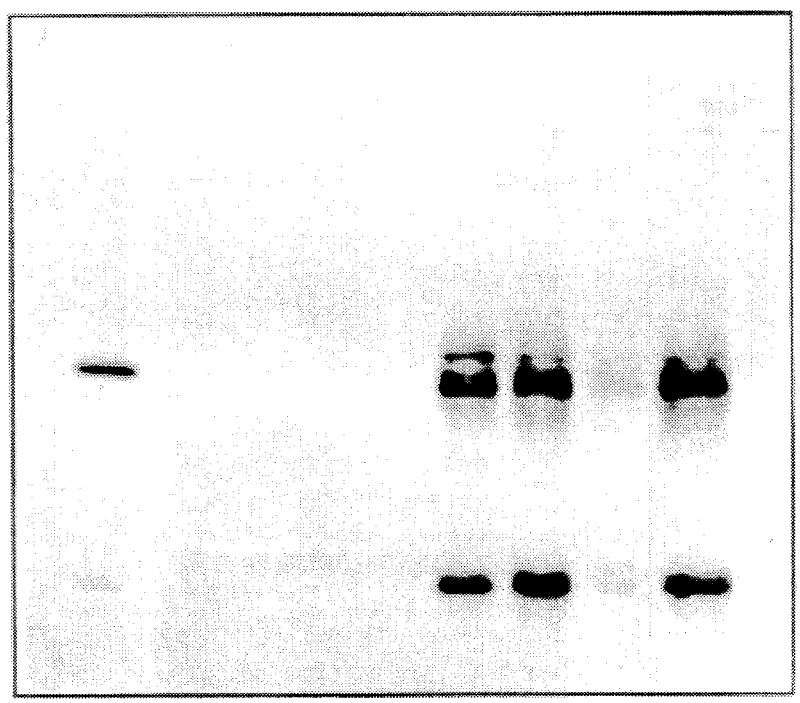
FIG. 8 is an autoradiograph of a Western blot analysis of transgenic A. thaliana plants expressing the plasmid pBI-TPSS-Syn and control plants. Aliquots of crude leaf protein extracts containing 50 µg protein were separated on a 8% SDS-PAGE. Proteins electroblotted on nitrocellulose were incubated with anti-PHB synthase antibody. Protein extracts analyzed were S8-1-2C (lane C, Somerville, C. R., Poirier, Y., and Dennis, D. E., patent application Ser. No. 07/732, 243), TPSS-Red STU (lane U), TPSS-Syn GHI1 (lane 1), TPSS-Syn GHI2 (lane 2), TPSS-Syn JKL (lane 3), and TPSS-Syn VXY (lane 4).

All of the 6 putative transgenic plants transformed with pBI-TPSS-Syn except TPSS-Syn-ABC and -PQR showed a signal. The intensity of these signals varied and was the strongest in plant TPSS-Syn-VWX (FIG. 8). The signal showed up as a triplet band at the size of the correctly processed TPSS-Syn protein (63 kDa), and a processed version slightly shorter than expected (60 and 61 kDa). The unmodified PHB Synthase migrates at 60 kDa.

In all Western blot analyses performed, proteins of untransformed plants showed no signal. Plants expressing the phb enzymes in the cytoplasm showed a strong signal at the expected size. The PHB enzymes modified with a transit peptide for targeting to the plastid were processed to the expected size and therefore mostly inserted into the plastid. In addition, bands at slightly higher or lower mobility also occurred. Proteins with a slightly higher mobility than expected might be generated by protease activity on the 23 amino acids of the mature protein of the small subunit of rubisco which were added to the bacterial enzymes. The artificially created extension might be especially susceptible to proteases.

These results indicate that for each construct containing the CaMV promoter, transformed plants could be obtained producing high levels of the expected enzymes. The appearance of each of these enzymes in the Western blot analyses as doublet or triplet of the expected sizes indicates that the enzymes are transported to the plastid and processed in the expected manner.

Transgenic plants obtained by transformation with the pBI-TPSS-Thio were assayed for 3-ketothiolase activity by minor modification of the assay described by Senior, P. J. and Dawes, E. A., Biochem. J. 134: 225–238, 1973. Frozen leaf tissues from kanamycin resistant heterozygote T1 plants were homogenized in Tris-buffer and the clarified crude extracts were tested for 3-ketothiolase activity. The results of these experiments are presented in Table 2.

TABLE 2

Levels of 3-ketothiolase activity in transgenic *A. thaliana* plants.

| sample | 3-ketothiolase activity[a] |
|---|---|
| TPSS-Red | 0.005 |
| TPSS-Thio GHI1 | 0.32 |
| TPSS-Thio L | 0.30 |
| TPSS-Thio STU4 | 0.27 |

[a]Micromoles of acetoacetyl-CoA degraded per minute per milligram of protein. Values are an average of two to four measurements.

Extracts of untransformed plants, transgenic plants transformed with pBI-TPSS-Red and transgenic plants transformed with pBI-TPSS-Thio which did not express the gene as detected by Western blot analysis had very low levels of 3-ketothiolase activity under the assay conditions. By contrast, each of the transgenic plants found to have a high 3-ketothiolase production in the Western blot analysis had also an increased level of 3-ketothiolase activity. This indicates that the modified bacterial 3-ketothiolase is functional in plants. The specific activity of the modified 3-ketothiolase was as active as the unmodified bacterial 3-ketothiolase expressed in the cytoplasm of Arabidopsis plants.

Transgenic plants obtained by transformation with the pBI-TPSS-Red were assayed for acetoacetyl-CoA reductase activity by minor modifications of the assay described by Senior, P. J. and Dawes, E. A., Biochem. J. 134: 225–238, 1973. Leaves from kanamycin resistant heterozygote T1 plants were homogenized in potassium phosphate buffer and the clarified extracts were assayed for acetoacetyl-CoA reductase activity. The results of these experiments are presented in Table 3.

TABLE 3

Levels of acetoacetyl-CoA reductase activity in transgenic *A. thaliana* plants.

| sample | acetoacetyl-CoA reductase activity[a] |
|---|---|
| TPSS-Syn | 0.047 |
| TPSS-Red DEF | 1.13 |
| TPSS-Red GHI1 | 0.49 |
| TPSS-Red GHI2 | 0.75 |
| TPSS-Red MNO1 | 1.07 |
| TPSS-Red MNO2 | 0.31 |
| TPSS-Red STU | 3.39 |
| TPSS-Red VWX | 0.28 |

[a]Micromoles of NADPH oxidizied per minute and milligram of protein. Values are an average of two to four measurements.

Extracts from plants which were untransformed, transformed with pBI-TPSS-Thio or transformed plants which did not express the gene as detected by Western blot analysis had undetectable levels of acetoacetyl-CoA reductase. By contrast, each of the transgenic plants which were found to produce the acetoacetyl-CoA reductase in the Western blot analysis showed acetoacetyl-CoA reductase activity. The level of activity correlated with the level of production seen in the Western blot. This indicates that the modified bacterial acetoacetyl-CoA reductase is functional in plants.

Transgenic plants obtained by transformation with the construct pBI-TPSS-Syn were not assayed for the presence of PHB synthase activity because of technical difficulties in measuring the activity of this enzyme in the absence of thiolase and reductase activities (Peoples, O. P. and Sinskey, A. J., J. Biol. Chem. 264: 15298–15303, 1989).

In summary, the results of these experiments indicate that all three enzymes involved in PHB synthesis modified for plastid targeting were produced to significant levels in plants, were processed in the manner expected for transport to the plastid and were enzymatically active.

6.1.2. Analysis of Putative Transgenic Plants Obtained After Transformation with pBIB-CCN-Thio, pBIB-KCN-Red and pBIB-HCN-Syn.

In order to determine whether the putative transgenic plants transformed with pBIB-CCN-Thio, pBIB-KCN-Red and pBIB-HCN-Syn produce the appropriate enzyme, the proteins in the immature seeds were analyzed. Since Pang et al. showed that the seed specific promoter used in these experiments directs a high gene expression between day 6 and day 14 after fertilization of the flowers, the seeds were collected in this period (Pang, P. P., Pruitt, R. E. and Meyerowitz, E. M., Plant Mol. Biol. 11: 805–820, 1988). Frozen immature seeds were homogenized in buffer and the proteins present in the aqueous phase were separated by SDS polyacrylamide gel electrophoresis. The proteins were transferred to nitrocellulose and incubated with antibodies as described above.

Figure 9:
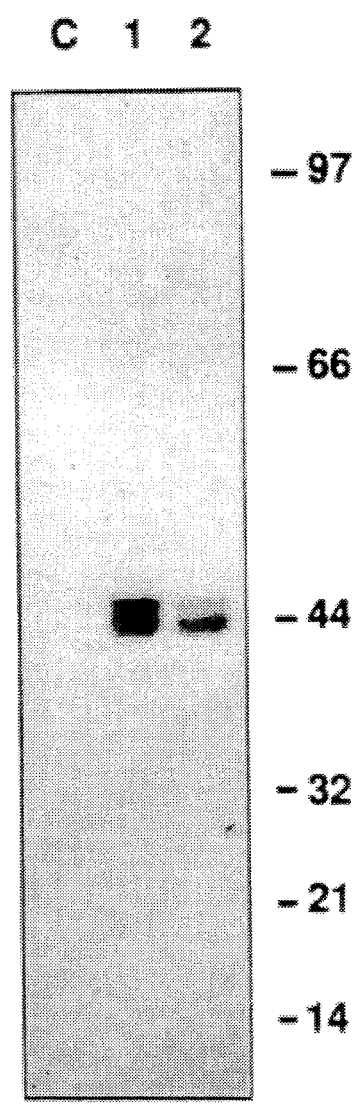
FIG. 9 is an autoradiograph of a Western blot analysis of transgenic A. thaliana plants expressing the plasmid pBIB-CCN-Thio and control plants. Aliquots of crude seed protein extracts containing 50 µg protein were separated on a 12% SDS-PAGE. Proteins electroblotted on nitrocellulose were incubated with anti-3-ketothiolase antibody. Protein extracts analyzed were CN-Red 17-1 (lane C), CN-Thio 13-3 (lane 1) and CN-Thio 14-1 (lane 2).

Both plants obtained after transformation with pBIB-CCN-Thio showed a high level of expression of the enzyme in the Western blot. The enzyme appeared as a quadruplet at sizes between 43 and 47 KDa. The band at 47 KDa represents the size expected for the correctly processed form of the modified enzyme (FIG. 9).

Figure 10:
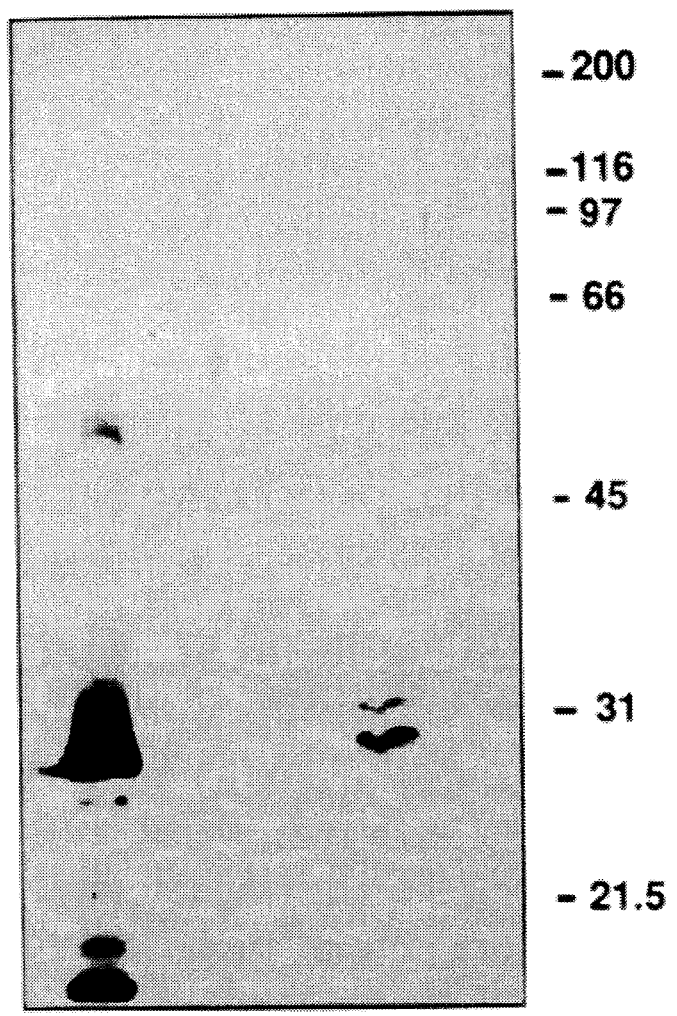
FIG. 10 is an autoradiograph of a Western blot analysis of transgenic A. thaliana plants expressing the pBIB-KCN-Red and control plants. Aliquots of crude protein extracts containing 50 µg protein were separated on a 12% SDS-PAGE. Proteins electroblotted on nitrocellulose were incubated with anti-acetoacetyl-CoA reductase antibody. Protein extracts analyzed were RedB-2B (lane LR; Somerville, C. R., Poirier, Y., and Dennis, D. E., patent application Ser. No. 07/732,243), seed protein extracts were CN-Syn 34-1H1 (lane U), CN-Red 17-3K (lane 1) and CN-Red 17-1 (lane 2).

In the Western blot analysis of the 6 kanamycin resistant plants only the protein extract of plant 17-3K reacted with the antibody raised against the acetoacetyl-CoA reductase. The signal appeared as a double band at the size of the correctly processed form of the protein (29 KDa) and a slightly larger protein (31 KDa) (FIG. 10).

Figure 11:
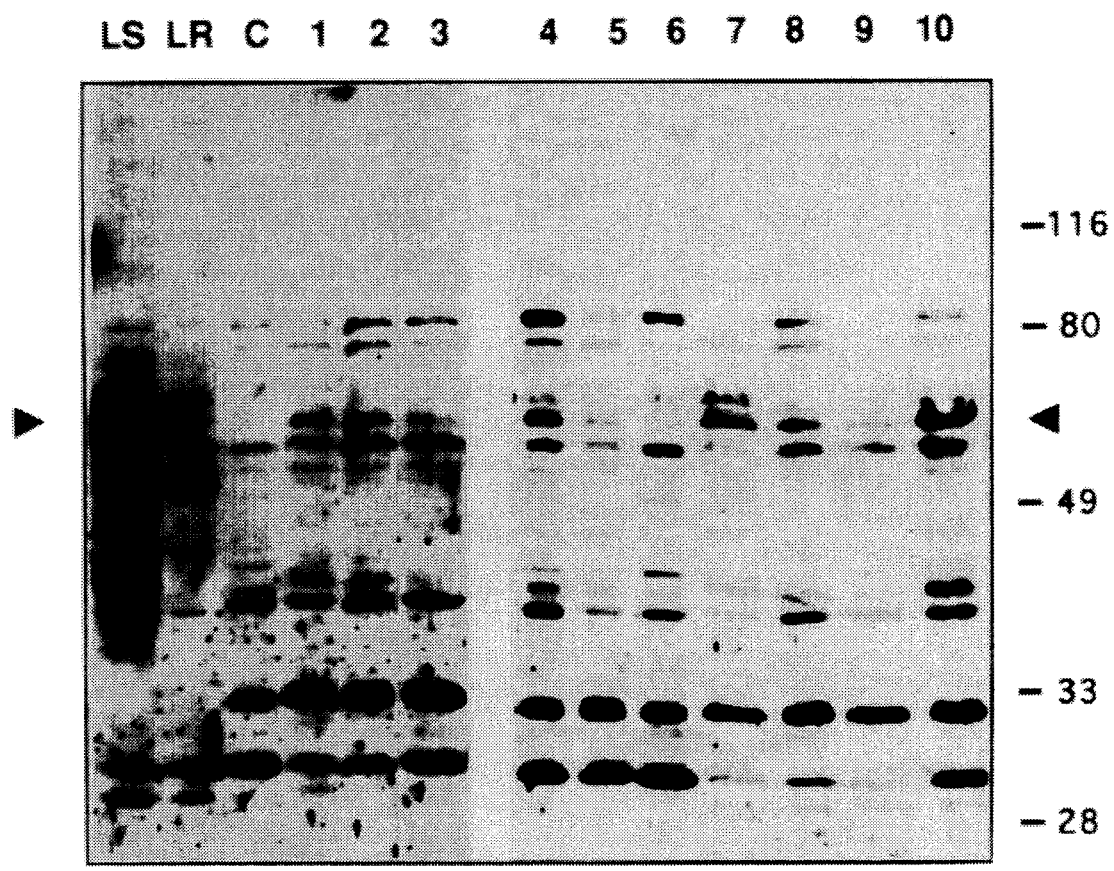
FIG. 11 is an autoradiograph of a Western blot analysis of transgenic A. thaliana plants expressing the plasmid pBIB-HCN-Syn and control plants. Aliquots of crude protein extracts containing 50 µg protein were separated on a 12% SDS-PAGE. Proteins electroblotted on nitrocellulose were incubated with anti-PHB synthase antibody. Protein extracts analyzed were S8-1-2C (lane LS; Somerville, C. R., Poirier, Y., and Dennis, D. E., patent application Ser. No. 07/732, 243), RedB-2B (lane LR; Somerville, C. R., Poirier, Y., and Dennis, D. E., patent application Ser. No. 07/732,243), CN-Red 17-1 (lane C), CN-Syn 35-1 (lane 1), CN-Syn 35-1aA (lane 2), CN-Syn 35-G1 (lane 3), CN-Syn 34-1 Hb (lane 4), CN-Syn 34-1 Hc (lane 5), CN-Syn 34-1bA (lane 6), CN-Syn 34-1bA2 (lane 7), CN-Syn 34-1bB (lane 8), CN-Syn 34-1B (lane 9), and CN-Syn 34-1G (lane 10).

Thirteen of the 17 plants obtained after transformation with pBIB-HCN-Syn were analyzed. Among these, 11 plants showed low level expression of the modified bacterial synthase. The transgenic plant TPSS-Syn 34-1G1 has an approximately five times higher level of expression than the other transgenic plants. The signal appears as a single band of the size of the processed enzyme (63 KDa) (FIG. 11).

The preliminary results of the modified PHB enzymes expressed under control of the seed-specific promoter indicate that they are being synthesized in the seeds and are processed in the manner expected for targeting to the plastid.

After obtaining the homozygote lines of the transformed plants expressing to a high level the appropriate phb enzymes, immuno localization studies will be undertaken to further show that the enzymes are located in the plastids.

6. 2. Analysis of the Integration of the phb Genes in Transgenic Plants

Figure 12A:
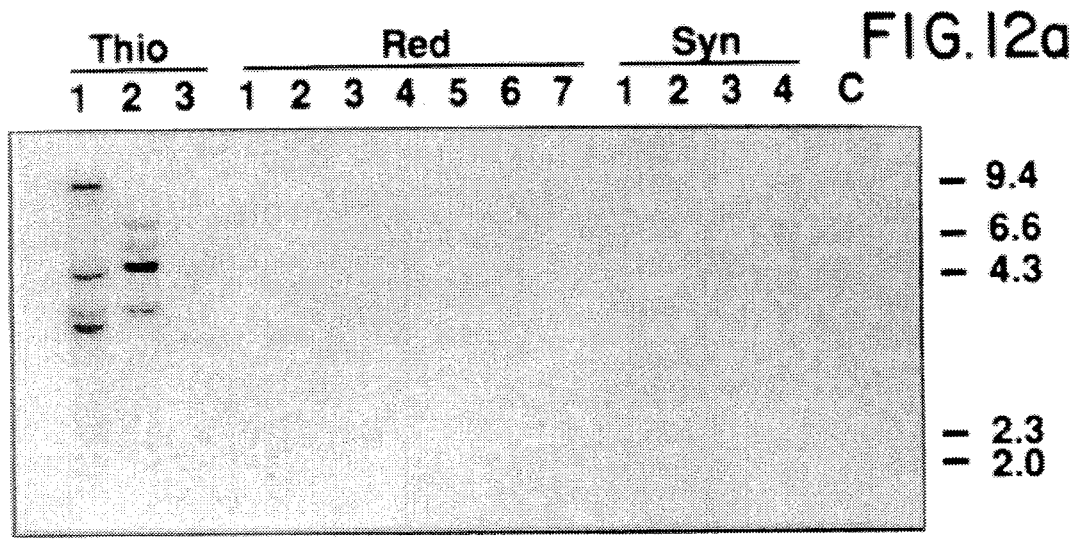
FIGS. 12a, 12b, and 12c are autoradiographs of Southern blot analyses of untransformed control and transgenic A. thaliana plants transformed with the plasmid pBI-TPSS-phb constructs. One µg of genomic DNA from untransformed A. thaliana race Rschew and from transgenic plants were digested with the restriction enzyme HindIII, the fragments were separated by agarose gel electrophoresis and transferred to nylon membranes. Filters were hybridized to $^{32}$P-labeled DNA fragments from genes (FIG. 12a) phbA, (FIG. 12b) phbB and (FIG. 12c) phbC. The genomic DNAs analyzed were TPSS-Thio GHI1 (lane Thio 1), TPSS-Thio L (lane Thio 2), TPSS-Thio STU4 (lane Thio 3), TPSS-Red DEF (lane Red 1), TPSS-Red GHI1 (lane Red 2), TPSS-Red GHI2 (lane Red 3), TPSS-Red MNO1 (lane Red 4), TPSS-Red MNO2 (lane Red 5), TPSS-Red STU (lane Red 6), TPSS-Red VWX (lane Red 7), TPSS-Syn GHI1 (lane Syn 1), TPSS-Syn GHI2 (lane Syn 2), TPSS-Syn JKL (lane Syn 3), TPSS-Syn VWX (lane Syn 4) and untransformed wild type (lane C).
Figure 12B:
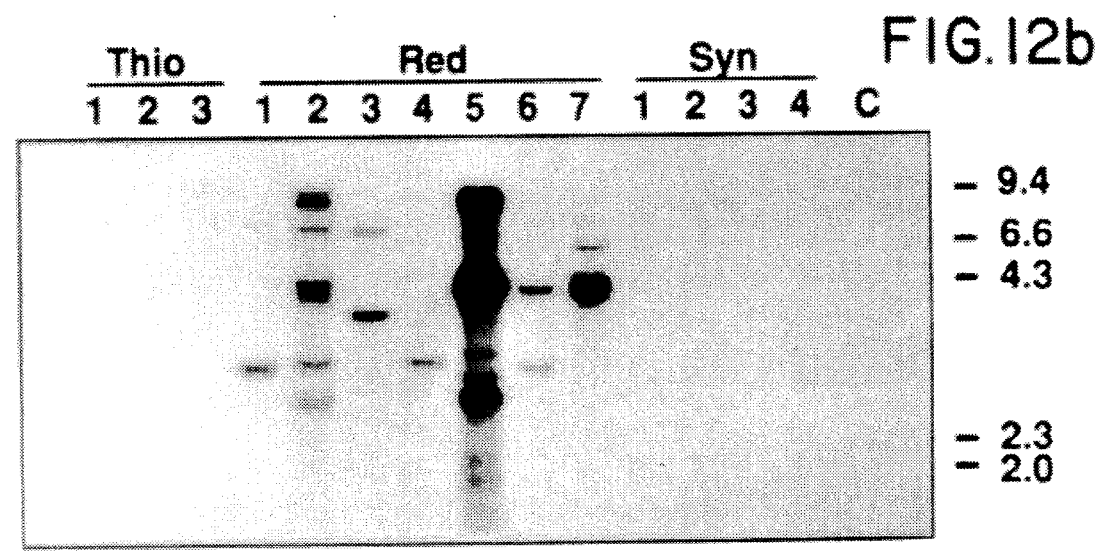
Figure 12C:

In order to verify the proper integration of the phb genes in the various transgenic plant lines produced, the genomic DNA of the transgenic plants was analyzed. High molecular weight DNA from control untransformed plants and from T2 transgenic plants transformed with the plasmids pBI-TPSS-Thio, pBI-TPSS-Red and pBI-TPSS-Syn or pBIB-CCN-Thio, pBIB-KCN-Red and pBIB-HCN-Syn was isolated. The DNAs were digested with the restriction enzymes HindIII, the fragments separated by agarose gel electrophoresis and transferred onto a nylon filter. In the constructs pBI-TPSS-Thio, pBI-TPSS-Red and pBI-TPSS-Syn, the restriction enzyme HindIII cuts only once at the 5' end of the CaMV 35S promoter (FIG. 4). In the construct pBIB-CCN-Thio, pBIB-KCN-Red and pBIB-HCN-Syn, the restriction enzyme HindIII cuts several times, but only 5' of the coding region of the phb genes. Fragments detected using phb gene specific probes should therefore represent junction fragments of the Ti vectors with the plant genomic DNA, or internal fragments of concatemerized Ti vectors. The inserts in plasmids pUC-THIO, pUC-RED and pUC-SYN were excised by treatment with EcoRI and HindIII, purified by electrophoresis and labeled with $^{32}$P-deoxyribonucleotides by random priming. The labeled phb gene fragments were then used to probe the nylon filters. The filters were hybridized and subsequently washed under high stringency conditions. The result of these filter hybridizations is shown in FIG. 12 for the pBI-TPSS-phb constructs and in FIG. 13 for the pBIB-CN-phb constructs. None of the three phb genes can be detected in untransformed control plants (FIGS. 12 $a$, $b$, $c$ and 13 $a$, $b$, $c$, lane C).

Figure 13A:
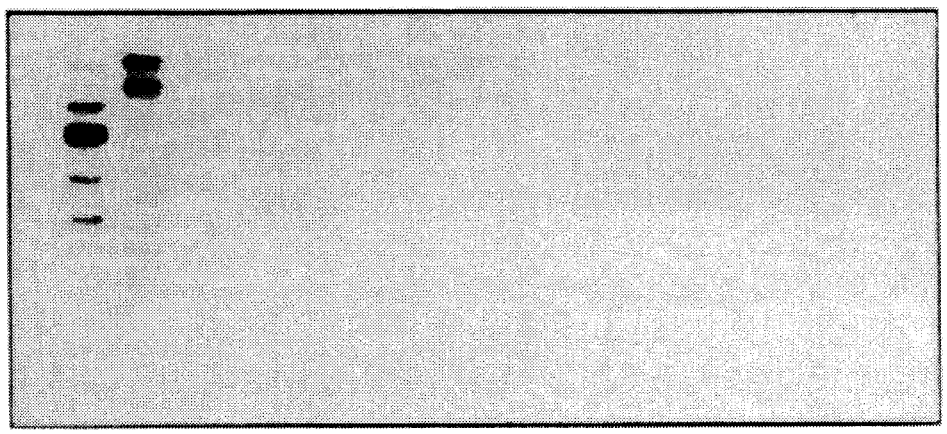
FIGS. 13a, 13b, and 13c are autoradiographies of a Southern blot analyses of untransformed control and transgenic A. thaliana plants transformed with the plasmid pBIB-CN-phb constructs. The genomic DNAs analyzed were CN-Thio 13-3 (lane Thio 1), CN-Thio 14-1 (lane Thio 2), CN-Red 17-2 (lane Red 1), CN-Red 17-3 (lane Red 2), CN-Red 17-1dA (lane Red 3), CN-Red 17-1dB (lane Red 4), CN-Red 17-3K (lane Red 5), CN-Red 17-2K (lane Red 6), CN-Syn 34-1bA (lane Syn 1), CN-Syn 34-1bB (lane Syn 2), CN-Syn 34-1Hb (lane Syn 3), CN-Syn 34-1G1 (lane Syn 4), CN-Syn 35-1 (lane Syn 5), CN-Syn 35-1A (lane Syn 6), and untransformed wild type (lane C). Refer to figure legend 12a, 12b, and 12c for a more detailed description.
Figure 13B:
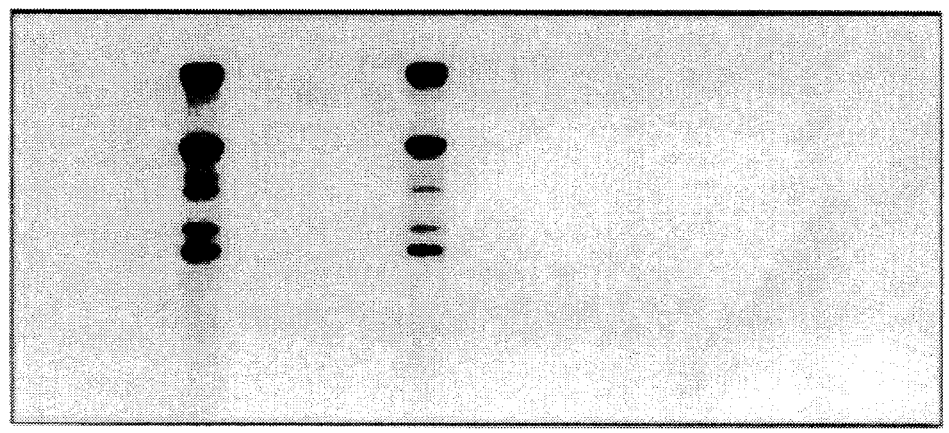
Figure 13C:
Figure 15A:
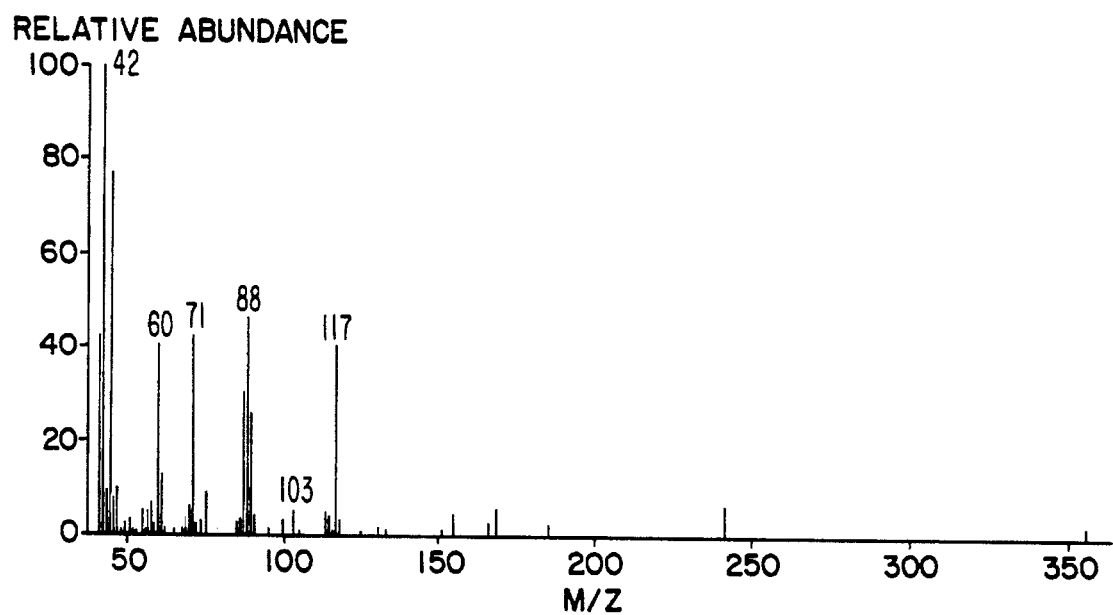
FIGS. 15A and 15B show gas chromatography-mass spectrometry analyses of ethyl-hydroxybutyrate prepared from a PHB standard and PHB from plant extracts.
Figure 15B:
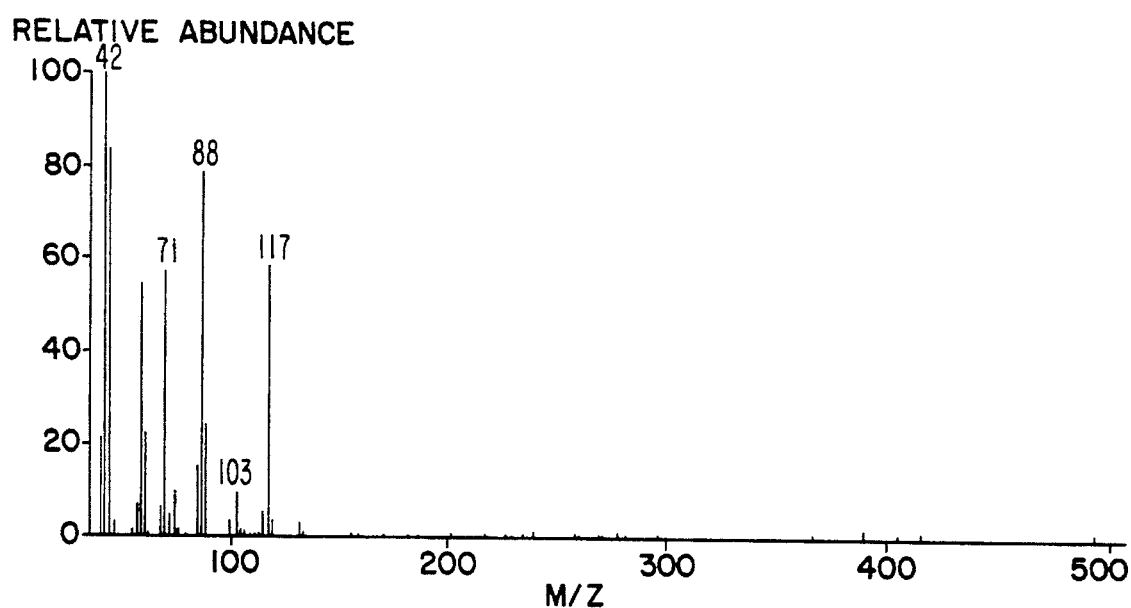

The phbA gene was detected in the three transgenic lines produced by transformation with the plasmid pBI-TPSS-Thio (FIG. 12$a$, lane Thio 1-3) and in the two transgenic lines produced by transformation with the plasmid pBIB-CCN-Thio (FIG. 13$a$, lane Thio 1-2).

The phbB gene was detected in the transgenic plants produced by transformation with the plasmid pBI-TPSS-Red (FIG. 12$b$, lanes Red 1-7) and in 2 of the six transgenic lines produced by transformation with the plasmid pBIB-KCN-Red (FIG. 13$b$, lane Red 1 and 5). Although the plant lines CN-Red 17-3,-17-1dA, 17-1dB and -17-2K were resistant to 50 µg/ml of kanamycin, suggesting the integration of the NPTII gene, no phbB gene could be detected. It is likely that only the fragment of the Ti vector harboring the NPTII gene, and not the phbB gene, was integrated in the genomic DNA of these lines (FIG. 13$b$, lane Red 2, 3, 4, 6).

The phbC gene was detected in the four transgenic plant lines produced by transformation with pBI-TPSS-Syn (FIG. 12$c$, lane Syn 1-4) and in the six transgenic plants lines produced by transformation with the plasmid pBIB-HCN-TPSS-Syn, which were analysed (FIG. 13$c$, lane Syn 1-6). The transgenic plant lines CN-Syn 34-1bA and CN-Syn 34-1bB are identical since they have the same pattern of bands on the Southern blot (FIG. 13$c$, lane Syn 1 and 2). The same phenomenon can be seen for the plants CN-Syn 34-1Hb and CN-Syn 34-1G1 (FIG. 13$c$, lane Syn 3 and 4) and the plants CN-Syn 35-1 and CN-Syn 35-1a (FIG. 13$c$, lane Syn 5 and 6) and is related to the transformation method.

A series of sexual crosses was used to construct plant lines containing all three phb enzymes in the plastid of all tissues. Three transgenic lines expressing high amounts of acetoacetyl-CoA reductase in the plastid (lines TPSS-Red DEF, MNO1 and STU) were cross-pollinated with transgenic plants producing high amount of PHB synthase in the plastid (lines TPSS-Syn GHI1, GHI2 and VWX). The resulting hybrid TPSS-Red/TPSS-Syn plants expressing acetoacetyl-CoA reductase and PHB synthase in the plastid did not produce measurable amounts of PHB in expanding leaves, as analyzed by gas chromatography (<20 µg/g fresh weight PHB). By comparison, transgenic plants producing the acetoacetyl-CoA reductase and the PHB synthase to similar level in the cytoplasm produced PHB (Poirier, Y., Dennis, D. E., Klomparens, K., and Somerville, C. R. Science 256, 520–523, 1992 and patent application Ser. No. 07/732,243). A possible reason for this difference is that plastids may not have sufficient 3-ketothiolase to support PHB production. This is consistent with evidence that the early steps of the mevalonate pathway leading from acetyl-CoA to isopentenyl-pyrophosphate are absent in differentiated plastids (Kreuz, K. & Kleinig, H. Eur. J. Biochem. 141, 531–535, 1984, Schultz, G. & Schulze-Siebert, D. in Biological Role of Plant Lipids, eds. Biacs P. A., Gruiz, K., & Kremmer, T. (Plenum Publishing Corporation, New York, N.Y.) pp. 313–319, 1989).

Figure 16A:
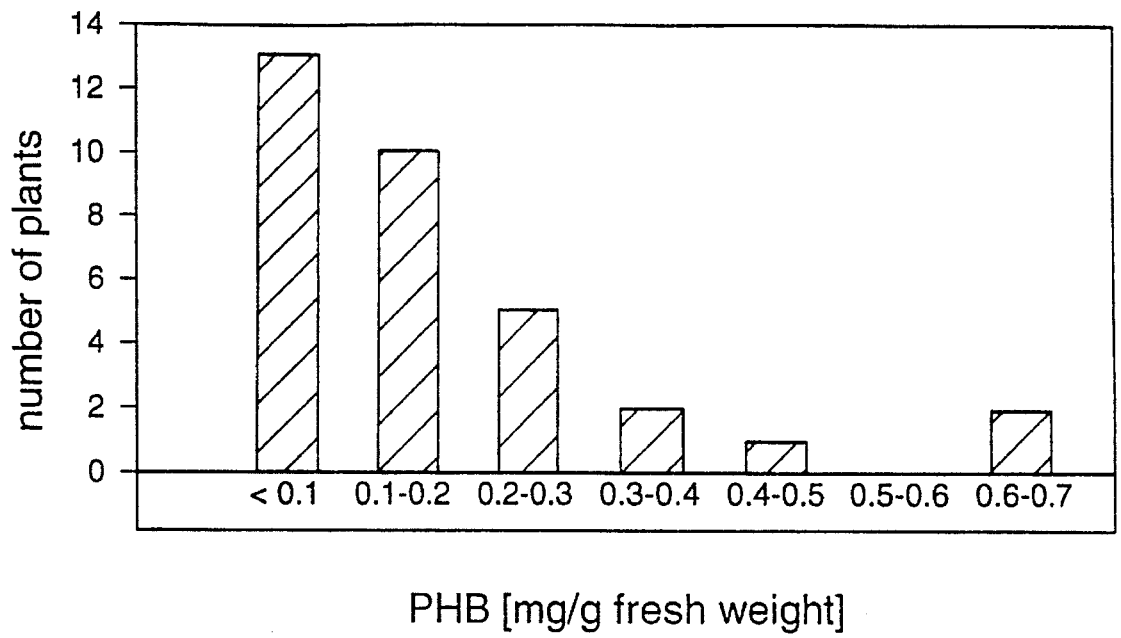
FIGS. 16A and 16B show bar graphs illustrating the PHB accumulation in leaves of different hybrid TPSS-Thio/TPSS-Red/TPSS-Syn plants.
Figure 16B:
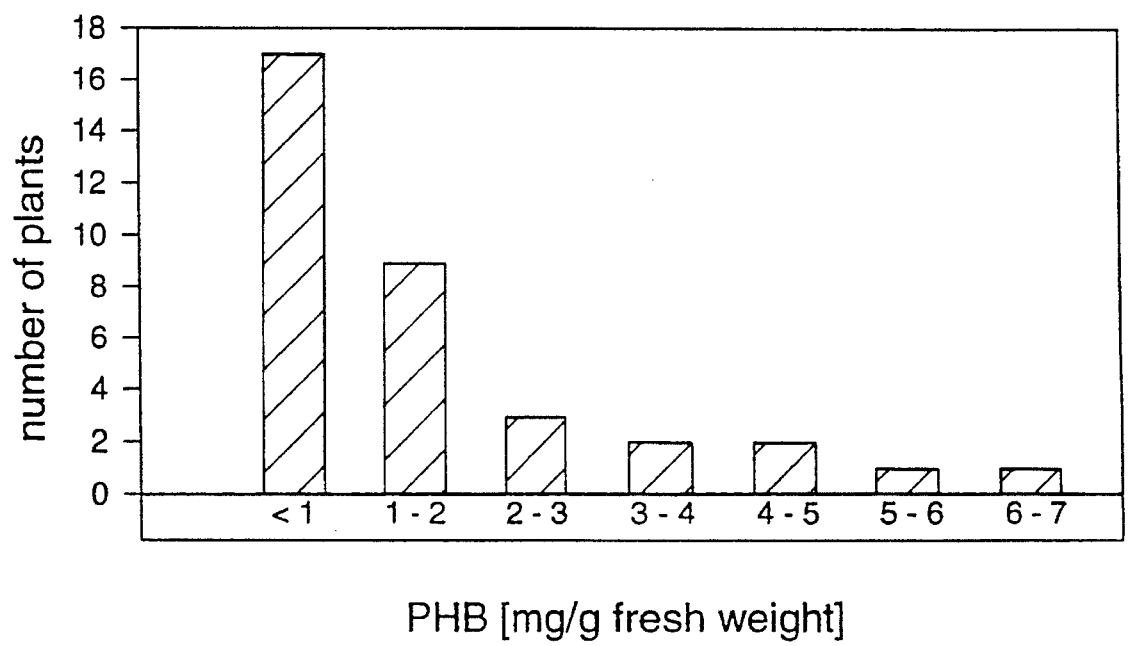

In order to establish a complete PHB biosynthetic pathway in plastids of all tissues, transgenic A. thaliana having a high amount of thiolase (line TPSS-Thio L) were cross-pollinated with the TPSS-Red/TPSS-Syn hybrids. From five combinations of crosses, a number of hybrids were obtained producing PHB and having therefore all three enzymes necessary for PHB production (TPSS-Thio L/TPSS-Red DEF/TPSS-Syn GHI1, TPSS-Thio L/TPSS-Red STU/TPSS-Syn GHI1, TPSS-Thio L/TPSS-Red STU/TPSS-Syn-GHI2, TPSS-Thio L/TPSS-Red STU/TPSS-Syn VWX, TPSS-Thio L/TPSS-Red MNO1/TPSS-Syn VWX). Hybrids producing PHB were first identified by epifluorescence microscopy of tissues stained with Nile Blue A. Plants with high levels of fluorescence had higher levels of PHB than plants with comparatively lower levels of fluorescence. PHB produced in these hybrids was then quantified by gas chromatography and identified by GC-MS analysis (FIGS 14A, 14B, 14C, 15A, and 15B). The amount of PHB in expanding leaves of 20 to 30 day old plants ranged from 20 µg of PHB/g fresh weight to 700 µg of PHB/g fresh weight (FIG. 16A). The triple hybrids continued to accumulate PHB throughout the life of the plants so that in the leaves of senescing plants levels of PHB were 8 to 13 times higher than the amount in expanding leaves (i.e., up to 7 mg PHB/g fresh weight) (FIG. 16B). This increase in PHB accumulation with time was observed in plants with a low initial PHB content (100 µg/g fresh weight in expanding leaves reaching 1.1 mg/g in pre-senescing leaves) as well as in plants with a high initial PHB content (700 µg/g fresh weight in expanding leaves reaching 7 mg/g fresh weight in pre-senescing leaves). In a TPSS-Thio L/TPSS-Red DEF/TPSS-Syn GHI1 hybrid, the maximal amount of PHB measured in the senescing leaves was approximately 14% of their dry weight (10 mg/g fresh weight).

Figure 17A:
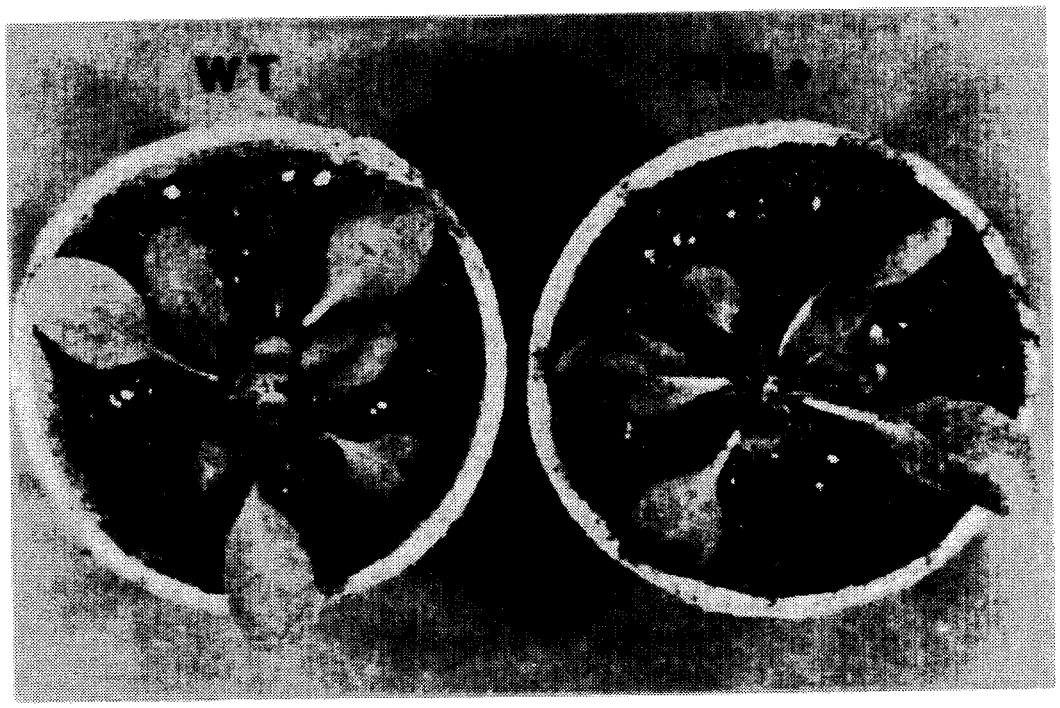
FIGS. 17A and 17B show pictures of fully developed rosettes of wild type (WT) and transgenic Arabidopsis plants expressing the PHB biosynthetic enzymes in the plastid (FIG. 17A) and in the cytoplasm (FIG. 17B). The leaves of the hybrid TPSS-Thio L/TPSS-Red DEF/TPSS-Syn-GHI1 producing PHB in the plastid contained approximately 1.2 mg PHB/g fresh weight (A, PHB+). The Red/Syn hybrid expressing the PHB enzymes in the cytoplasm contained approx. 100 µg PHB/g fresh weight (B/PHB+). Wild type and transgenic plants were grown under identical conditions.
Figure 17B:
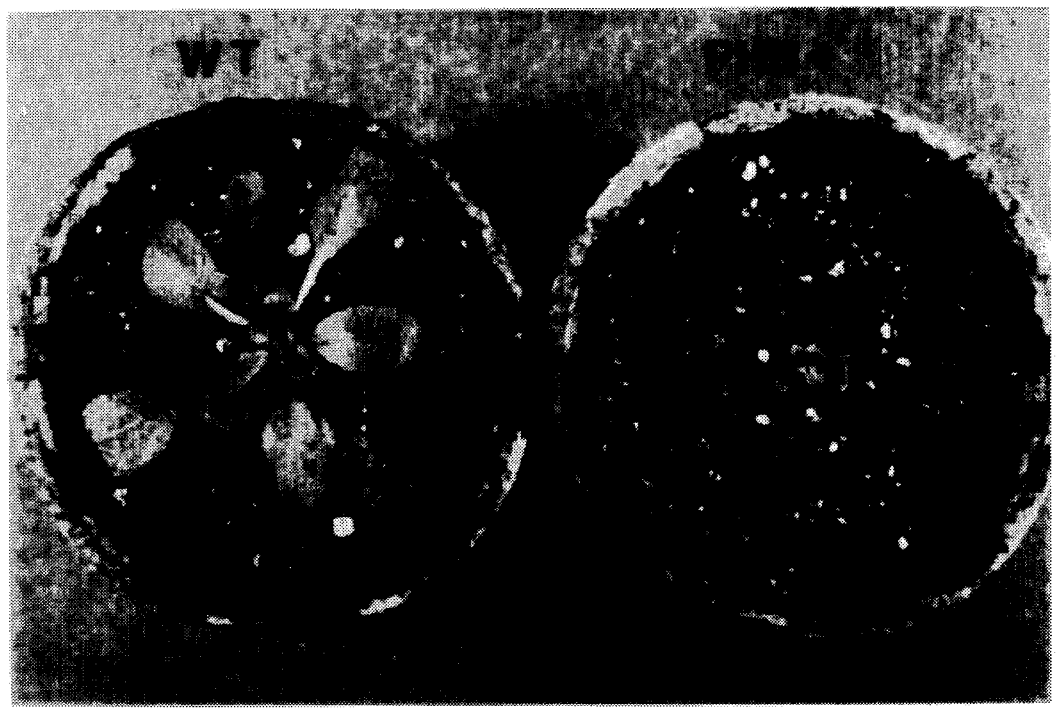
Figure 18:
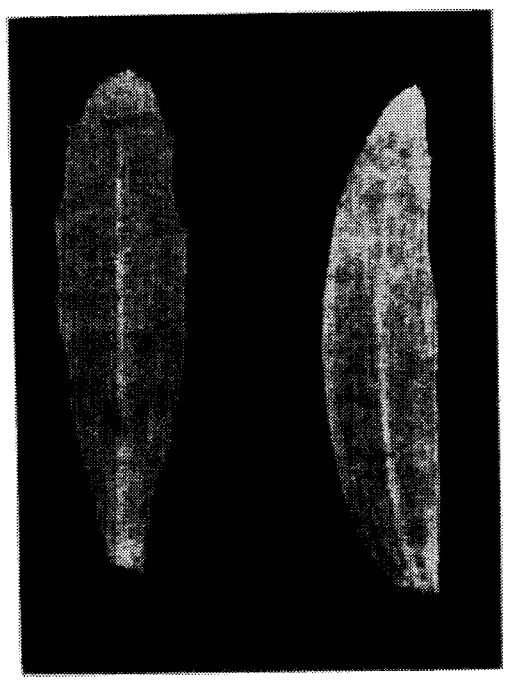
FIG. 18 shows a picture illustrating the effect of high level accumulation of PHB in the plastid on leaf pigmentation. (A) Leaf of a 50 day old wild type plant; (B) Leaf of a 50 day old transgenic Arabidopsis hybrid producing 700 µg PHB/g fresh weight in the plastid of expanding leaves.

Plants producing PHB in the plastid showed wild type growth and fertility even at the highest level of PHB accumulation (FIG. 17). No differences were observed with wild type in the rate of germination of seeds of hybrids producing high level of PHB. However, plants producing more than 300–400 µg PHB/g fresh weight in expanding leaves could be distinguished from the wild type by visual inspection during the later stages of growth. In these plants, the leaves showed slight chlorosis after approximately 50–60 days of growth, indicating that at very high levels of PHB accumulation (>3 mg PHB/g fresh weight) some aspect of chloroplast metabolism may be affected (FIG. 18).

Figure 19A:
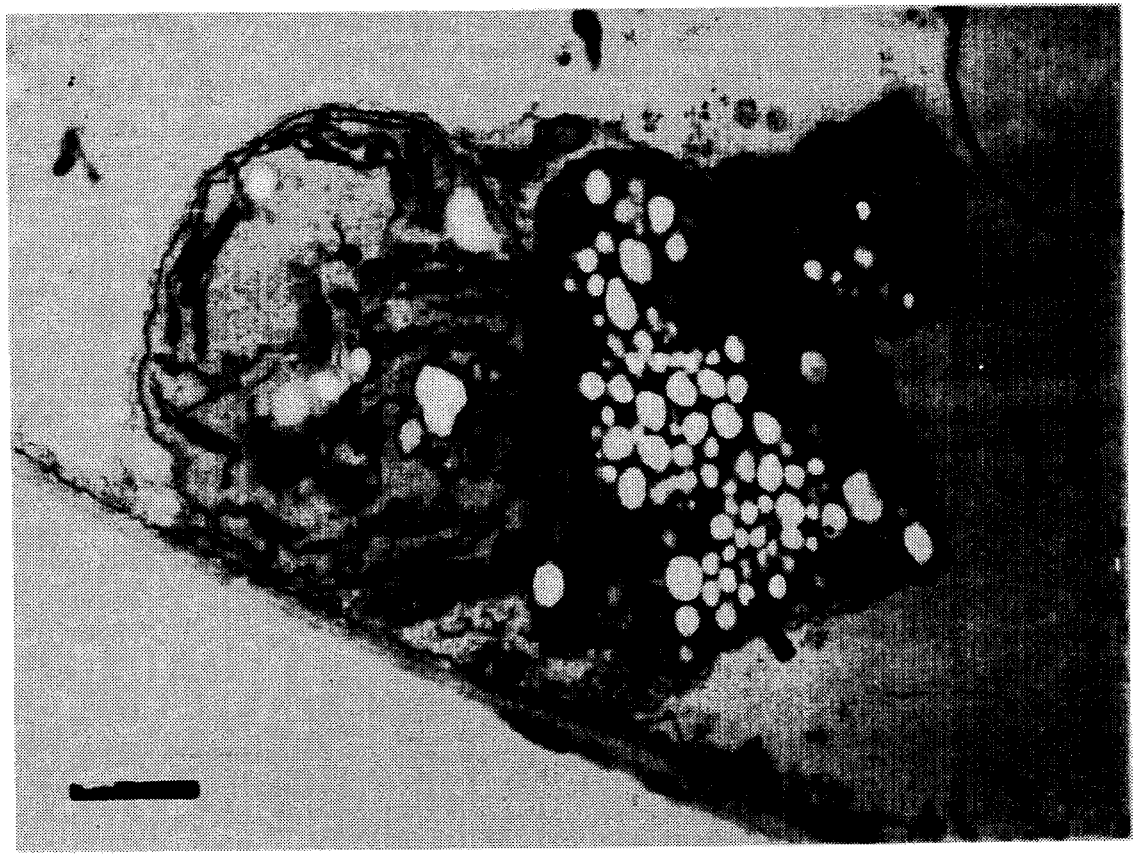
FIGS. 19A, 19B, and 19C show transmission electron micrographs (TEM) of thin sections from a PHB-producing tri-hybrid expressing the PHB enzymes in the plastid (TPSS-Thio L/TPSS-Red DEF/TPSS-Syn GHI1).
Figure 19B:
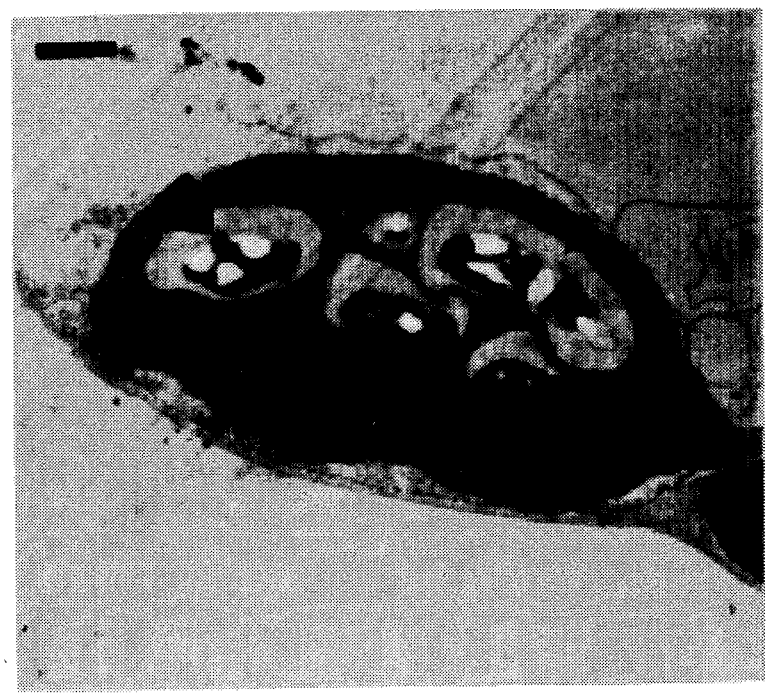
Figure 19C:
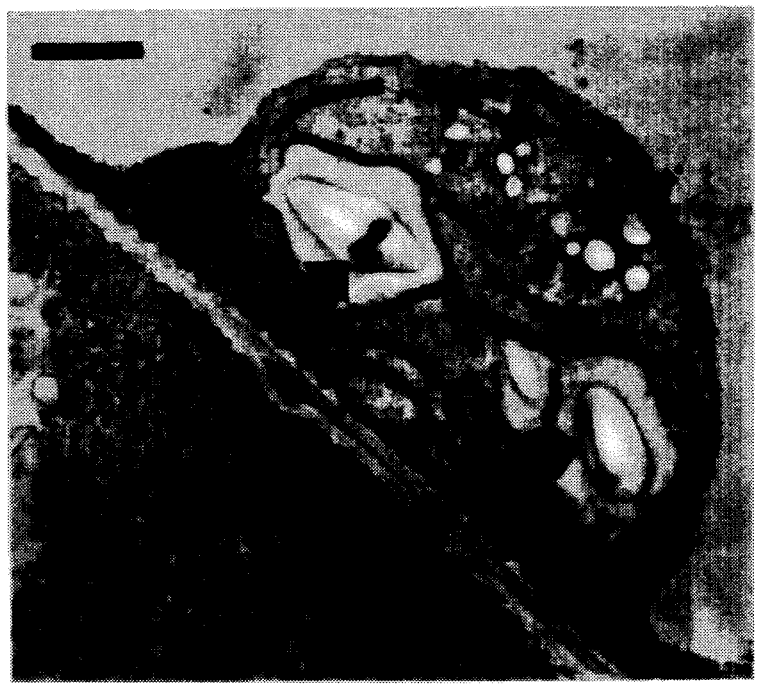

Transmission electron microscopy of leaf samples of PHB- producing hybrids revealed that PHB accumulated as agglomerations of electron-lucent granules of approximately 0.2 to 0.7 µm, surrounded by a thin layer of electron-dense material (FIG. 19A). Granules of similar appearance have been described for bacterial PHB (Lundgren, D. G., Pfister, R. M., & Merrick, J. M. J. Gen. Microbiol. 34, 441–446, 1964) or for PHB in the cytoplasm, nucleus and vacuole of plant cells (Poirier, Y., Dennis, D. E., Klomparens, K., and Somerville, C. R. Science 256, 520–523, 1992 and patent application Ser. No. 07/732,243). In plants expressing the plastid targeted phb enzymes, these granule agglomerations were exclusively located in the plastids. This is in contrast with transgenic plants expressing the PHB biosynthetic pathway in the cytoplasm which accumulated PHB in the nucleus, vacuole and cytoplasm, but not in the plastid (Poirier, Y., Dennis, D. E., Klomparens, K., and Somerville, C. R. Science 256, 520–523, 1992 and patent application Ser. No. 07/732,243). PHB granules were clearly distinguished from starch granules in form, appearance and organization of the granules as visualized by conventional electron-microscopy fixation protocol. PHB granules are small, round electron-translucent granules forming dense agglomerations (FIG. 17A). In comparison, starch appears as singular, electron-denser granules of ovular form, surrounded by a diffuse area (FIG. 19B). In tri-hybrids producing only a low amount of PHB in expanding leaves, it appeared by electron microscopy analysis that not all chloroplasts accumulated PHB. The reason for this is not known. There were no indications for differential expression of the transgenes in different tissues. Conceivably, it could simply reflect the fact that electron microscopy analysis only allows inspection of a small area of the total plastid volume. It could also reflect the action of co-suppression which may lead to a mosaic of differential expression, as observed in Petunia (Jorgensen, R. Trends in Biotechnology 8, 340–344, 1990). In old leaves of tri-hybrids accumulating high levels of PHB, almost all chloroplasts contained PHB.

In order to gain insights into the mechanisms responsible for the different amounts of PHB produced in the various hybrids, the level of the 3-ketothiolase and acetoacetyl-CoA reductase activity present in PHB producing plants was measured in clarified crude leaf protein extracts. The PHB synthase was analyzed by Western blot analysis. The 3-ketothiolase activity in TPSS-Thio L/TPSS-Red/TPSS-Syn hybrid plants ranged from 0.001 to 0.8 u/mg protein. In contrast, the -ketothiolase activity in the parental TPSS-Thio L plants was 0.84±0.15 u/mg protein. Southern blot analysis of the TPSS-Thio L line revealed 4 bands which hybridized to the phbA gene, probably corresponding to several independent integrations of the construct (FIG. 12a, TPSS-Thio lane 2). Therefore, segregation of the different pBI-TPSS-Thio constructs may have caused the range of 3-ketothiolase activities in the F1 generation. Such variation can be readily eliminated by using standard plant breeding methods to develop true breeding lines that are homozygous for the various transgenes of interest. The acetoacetyl-CoA reductase activity in TPSS-Thio L/TPSS-Red DEF/TPSS-Syn GHI1 hybrid plants ranged from 0.007 to 0.78 u/mg protein. The acetoacetyl-CoA reductase activity in the TPSS-Red DEF/TPSS-Syn GHI1 hybrid which served as a the parent in the cross with TPSS-Thio L was 2.09±0.23 u/mg protein. Southern blot analysis and analysis of the segregation ratio of the selectable marker in the F1 generation indicated that TPSS-Red DEF plants harbor the construct pBI-TPSS-Red at a single integration site (FIG. 12b, TPSS-Red lane 1). Western blot analysis indicated that the reduced activity was correlated with an approximately 10-fold reduction in protein amount in the clarified extracts of PHB-producing plants. Similarly, PHB-producing hybrid plants TPSS-Thio L/TPSS-Red STU/TPSS-Syn GHI1, TPSS-Thio L/TPSS-Red STU/TPSS-Syn GHI2, TPSS-ThioL/TPSS-Red STU/TPSS-Syn VWX, and TPSS-Thio L/TPSS-Red MNO1/TPSS-Syn VWX also had widely varying and unexpectedly low reductase activities in comparison to their parent plants which was correlated with low amounts of protein in Western blot analysis. The reason for the variable and unusually low amount of reductase activity in tri-hybrids cannot be explained by changes in the copy number of the pBI-TPSS-Red construct. This variability is thought to be due to the fact that all transcripts of the modified phb genes contain a common sequence of 243 bp, namely the coding region of the transit peptide (TPSS) (FIGS. 3a, 3b, and 3c). Gaining one or more thiolase genes modified with the coding region of the TPSS might down regulate other TPSS containing genes, such as TPSS-Red, by the mechanism of co-suppression (Jorgensen, R. Trends in Biotechnology 8, 340–344, 1990, Seymour, G. B., Fray, G. R., Hill, P, & Tucker G. A. Plant Mol. Biol. 23, 1–9, 1993). Co-suppression may also provide an explanation of why, upon examination by transmission electron microscopy, some cells appeared to be full of PHB whereas adjoining cells showed no PHB. Therefore, in order to avoid co-suppression and alleviate the variable and low expression of the phb genes in plants producing PHB, all phb genes should be modified for plastid targeting by the addition of a different transit peptide for each of the introduced phb genes. Sequences are now available for dozens of different chloroplast-localized proteins including the sequences of their transit peptides. Therefore, methods for improvements of the current invention by the replacement of part or all of the amino terminal transit peptides used in this example with that of a normally chloroplast-localized protein will be evident to one skilled in the art.

Figure 20:
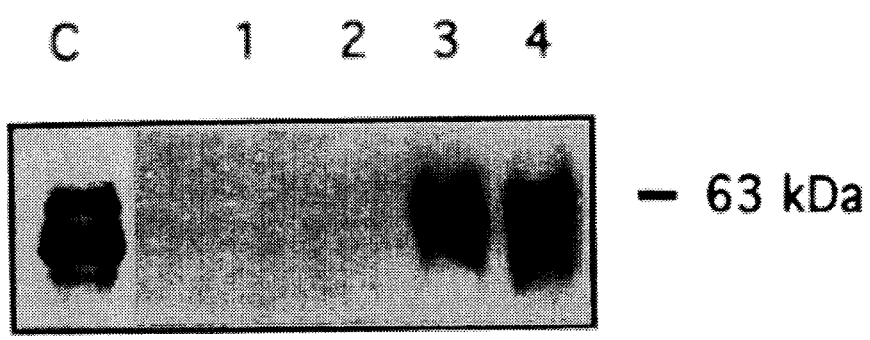
FIG. 20 shows a Western blot analysis of protein extracts of transgenic TPSS-Thio L/TPSS-Red DEF/TPSS-Syn GHI1 plants incubated with the anti-PHB synthase antibody. Extracts of soluble proteins (Lanes 1, 2) and of solubilized proteins of the membrane and particulate fraction (Lanes 3, 4) of two different TPSS-Thio L/TPSS-Red DEF/TPSS-Syn GHI1 plants. Lane-C shows extract of soluble proteins of a TPSS-Syn GHI1 plant.

The presence of PHB synthase was investigated by Western blot analysis of leaf protein extracts of PHB-producing plants. In TPSS-Thio/TPSS-Red/TPSS-Syn hybrid plants, PHB synthase could never be detected in the soluble protein fraction. However, PHB synthase was readily detectable on Western blot of solubilized membrane and particulate fractions of plant extracts. In contrast, in plants transformed only with the pBI-TPSS-Syn, PHB synthase could be detected in the soluble fraction (FIG. 20). This finding suggests that the PHB synthase is closely associated with the PHB granules formed in plants as shown for the PHB synthase in bacteria (Fukui, T., Yoshimoto, A., Matsumoto, M., Hosokawa, S. Saito, T., Nishikawa, H., & Tomita, K. Arch. Microbiol. 110, 149–156, 1976, Haywood, G. W., Anderson, A. J. and Dawes E. A. FEMS Microbiol. Lett. 57, 1–6, 1989).

In general, transgenic plants with the highest levels of both 3-ketothiolase and acetoacetyl-CoA reductase activities had the highest levels of PHB and plants with low levels of both activities had the lowest levels of PHB. There was no obvious plateau in PHB production at the highest levels of measurable enzyme activity. Therefore, it appeared that PHB accumulation was limited by the amount of enzyme activity rather than by the availability of acetyl-CoA. Therefore, it should be possible to increase the amount of PHB produced in transgenic plants beyond the amount described in this patent application by increasing the amount of the various phb enzymes produced in plants. One way to achieve this is to avoid the phenomenon of co-suppression of modified phb genes possessing the same transit peptide (for targeting to the plastid) by using a different plastid targeting sequence for each of the phb genes introduced in plants. It may also be possible to increase the amount of phb enzymes produced in transgenic plants by using strong promoters leading to higher expression level than possible with the CaMV or CRB promoters used in these experiments. Because the codon usage of the bacterial coding sequences of the phb genes is not typical for higher plants, it should also be possible to increase expression of the enzymes by altering the coding sequence of the bacterial genes so that the amino acid sequence is encoded by codons which are most commonly utilized by the higher plant in which the genes are to be expressed.

In summary, plants engineered to express the PHB biosynthetic pathway in their plastids accumulate PHB to high amounts. By changing the location of PHB production from a cellular compartment with a low flux through acetyl-CoA (cytoplasm) to a compartment with a high flux through acetyl-CoA (plastid), the maximal level of PHB production was increased by up to 100-fold (from approximately 100 µg per gram fresh weight for cytoplasmic expression, as described in Poirier, Y., Dennis, D. E., Klomparens, K., and Somerville, C. R. Science 256, 520–523, 1992 and patent application Ser. No. 07/732,243, to up to approximately 10 mg per gram fresh weight for plastid expression, as described in the present application). Plants producing high levels of PHB in the plastids showed normal growth and vigor. This indicates that PHB is not toxic for plants and that there appears to be no biological barrier to PHB production in plastids. Depletion of metabolites from essential metabolic pathways of the cytoplasm appears to have been the reason for the deleterious effect of PHB production in plants expressing the PHB enzymes in the cytoplasm (Poirier, Y., Dennis, D. E., Klomparens, K., and Somerville, C. R. Science 256, 520–523, 1992 and patent application Ser. No. 07/732,243). However, since PHB granules were also located in the nucleus, it might be possible that the interaction of the PHB granules with nuclear constituents was also a cause of the deleterious effect of PHB production in these plants.

A similar analysis will be performed with transgenic plants expressing the modified phb genes under the control of the seed-specific promoter CRB. Plants transformed with pBIB-KCN-Red, producing a substantial amount of acetoacetyl-CoA reductase in the plastid of developing seeds, will be cross-pollinated with plants transformed with pBIB-HCN-Syn, producing a substantial amount of PHB synthase in the plastid of developing seeds. The resulting hybrids will be analyzed for PHB production in the seeds by GC-MS analysis and electron microscopy. Since it is not obvious that the amount of endogenous acetoacetyl-CoA in the plastid of the developing seed is sufficient to allow PHB production, the 3-ketothiolase modified for plastid targeting in the plastid of developing seed will be introduced to create a tri-hybrid. In order to create a tri-hybrid producing all three enzymes, reductase/synthase double hybrids will be cross-pollinated with transgenic plants expressing the 3-ketothiolase in the plastid of developing seeds. The high amount of PHB produced in the seeds of the resulting thiolase/reductase/synthase tri-hybrids will be analyzed by GC-MS and electron microscopy.

This method for producing PHB in plastids is not restricted to the use of hybrid plants produced by crossing various transgenic lines. A preffered alternate implementation of the method would involve placing all three genes on a colinear DNA molecule for simultaneous introduction into the host plant. It is also envisioned that the general method for causing high levels of PHB production described herein are generally applicable method to all higher plants and that the minor modifications of the methods which may be required to introduce and cause expression of the genes, and transport of the proteins into the plastids in other species of higher plants will be evident to those skilled in the art.

Materials and Methods
  Construction of DNA Recombinants
  E.coli strain DH5α harboring plasmids were grown in LB broth supplemented with kanamycin (50 µg/ml) or ampicillin (50 µ/ml). Preparations of plasmid DNA was done by the alkaline lysis procedure as described by Sambrook, J., Fritsch, E. F. and Maniatis, T. Molecular cloning: a laboratory manual, Cold Spring Harbor Laboratory Press (1989) and if necessary a purification with the magic mini DNA affinity columns (Promega Corp., Wis.). Plasmid DNA was cleaved with restriction endonucleases according to the manufacturers recommendations (New England Biolabs, Mass; Promega Corp., Wis.; Boehringer Mannhein Biochemicals, IN; Stratagene, Calif.), separated by agarose gel electrophoresis and visualized by ethidium bromide staining as described by Sambrook, J., Fritsch, E. F. and Maniatis, T. Molecular cloning: a laboratory manual, Cold Spring Harbor Laboratory Press (1989). The DNA fragments were recovered from the agarose gel by a freeze throw method and phenol extractions. Briefly, the agarose fragment is sliced into very small pieces with a razor blade, the same volume of phenol (prepared as described in Sambrook, J., Fritsch, E. F. and Maniatis, T. Molecular cloning: a laboratory manual, Cold Spring Harbor Laboratory Press (1989)) is added and vigorously vortexed. The suspension is twice frozen and thrown and subsequently centrifuged. The fragment containing supernatant is furthermore purified by Phenol-chloroform extractions and ethanol precipitation. In some experiments, the recessed 3' termini of DNA fragments were converted into blunt ends with T4 DNA polymerase using the protocol described in Sambrook, J., Fritsch, E. F. and Maniatis, T. Molecular cloning: a laboratory manual, Cold Spring Harbor Laboratory Press (1989). Ligation of DNA fragments with cohesive or blunt ends was done at 14° C. for 16 h in buffer containing 50 mM Tris-HCl (pH 7.6), 5 mM $MgCl_2$, 5% (w/v) polyethylene glycol 8000, 0.5 mM ATP and 5 mM dithiothreitol as described by Sambrook, J., Fritsch, E. F. and Maniatis, T. Molecular cloning: a laboratory manual, Cold Spring Harbor Laboratory Press (1989). A fraction of the ligation reaction was transferred into E. coli by the rubidium chloride method as described by Hanahan, D., J. Mol. Biol. 166:557–580 (1983). The transformed bacteria were plated on agar plates containing LB broth and either 50 µg/ml kanamycin or 50 µg/ml ampicillin. Preparation of radiolabeled DNA probes and hybridization are described in a following section.

Oligonucleotides were synthesized by the biochemistry facility at Michigan State University.

Polymerase chain reaction (PCR) was performed using a Perkin-Elmer Cetus DNA thermal cycler (Perkin-Elmer, Conn.). The reaction mixture contained 200 pmoles of 2 oligonucleotides PCR primers (Table 1), 200 ng of plasmid (table 1), and 2.5 units of Vent polymerase in buffer conditions recommended by the supplier (New England Biolabs Inc, Mass.). The DNA thermal cycler program for the amplifications of the bacterial PHB enzymes was as follow: 4 min at 95° C., 30 cycles of the sequence 1.5 min at 97° C.—2 min at 65° C.—3 min at 72° C., and finally 7 min at 72° C. For the TPSS fragment: 4 min at 95° C., 30 cycles of the sequence 1.5 min at 95° C.—2 min at 60° C.—2 min at 72° C., and finally 7 min at 72° C. and for the CRB promoter: 4 min at 95° C., 30 cycles of the sequence 1.5 min at 95° C.—2 min at 58° C.—2 min at 72° C., and finally 7 min at 72° C. The PCR products was isolated by agarose gel electrophoresis and purified as described above.

Extraction and Restriction Endonuclease Cleavage of Genomic DNA

Wild type and transgenic plants were grown in soil for 2–3 weeks and approximately 5 g of leaf material was collected and frozen in liquid nitrogen. High molecular weight DNA was extracted from the frozen plant tissues as described by Rogers, S. C. and Bendich, A. J., Plant Molecular Biology Manual A6: 1–10 (1988). Restriction endonuclease cleavage with the enzyme HindIII on 1 µg of DNA was performed under the conditions recommended by the manufacturer (New England Biolabs Inc, Mass.).

Agarose Gel Electrophoresis and Hybridization Procedure

DNA analysis by agarose gel electrophoresis and transfer to nylon membranes (Hybond-N, Amersham, Il.) were done using established procedures described by Southern et al. (1975) and Sambrook, J., Fritsch, E. F. and Maniatis, T. Molecular cloning: a laboratory manual, Cold Spring Harbor Laboratory Press (1989). Specific cloned DNA fragments to be used as probes were excised from the vector with appropriate restriction endonucleases, the inserts were purified from the vector by agarose gel electrophoresis and electroelution. Fragments were labeled with $^{32}$P-deoxyribonucleotides by the random primer extension method using hexamers as described by Feinberg, A. P. and Volgelstein, B., Anal. Biochem. 132, 6–13 (1983). Nylon filters were hybridized with labeled probes and exposed on film as described by Poirier, Y. and Jolicoeur, P., J. Virol. 63, 2088–2098 (1989).

Construction of Fusion Proteins and Raising of Antibodies

For raising antibodies against the 3-ketothiolase, acetoacetyl- CoA reductase and PHB synthase of A. eutrophus fusionproteins with the maltose binding protein malc of E. coli were constructed by using the pIH821 vector (New England Biolabs Inc, Mass.). The MALE-Thiolase fusionprotein was constructed by purifying the 1.2 kbp XhoII-EcoRI fragment of the pUC-Thio plasmid (Somerville, C. R., Poirier, Y., and Dennis, D. E., patent application Ser. No. 7/732,243), filling in the ends by T4-DNA polymerase and cloning it in pIH821. The vector had been prepared by digestion with XbaI and filling in the end by T4-DNA polymerase. Clones carrying the insert in the desired orientation contain the gene fusion in a way that the reading frame is correct to obtain the MALE-Thiolase fusion. The plasmid was designated as pmalE-Thio.

To obtain the MALE-Reductase fusionprotein the pUC-Red plasmid (Somerville, C. R., Poirier, Y., and Dennis, D. E., patent application Ser. No. 07/732,243) was digested with DdeI and SacI. After purification of the 0.7 kbp fragment, the ends were filled in with T4-DNA polymerase. The blunt ended fragment was cloned in the XbaI digested and blunt ended pIH821 vector as described above. The clone containing the fragment in the exact orientation for expression of the MALE-Reductase expression was designated as pmalE-Red.

For the construction of the MALE-Synthase fusion protein the pUC-Syn was digested with NcoI and the ends were filled with T4-DNA polymerase. Subsequently, the plasmid was digested with HindIII and the 1.6 kbp fragment was cloned into the pIH821. The vector had been prepared by digesting with XbaI and filling in the end with T4 DNA Polymerase and subsequently digesting with HindIII. The clones were designated as pmalE-Syn.

The pmalE-Thio, -Red and - Syn plasmids were transformed into DH5α and the fusion proteins were expressed and purified as described by the manufacturer (New England Biolabs Inc, Mass.). The fusion proteins were injected into rabbits to raise polyclonal antibodies by using Freund's adjuvants as immunstimulants.

Assay for 3-Ketothiolase Activity

Frozen leaf samples (0.1 g) were homogenized in 200 µl of ice-cold thiolase buffer containing 100 mM Tris-HCl (pH 8.0), 40 mM $MgCl_2$ and 5 mM mercaptoethanol. The homogenate was clarified by centrifugation at 10000×g for 5 min and the supernatant transferred to a fresh tube. The protein content of the extract was measured by the Bradford assay using the Bio Rad protein assay kit (Bio Rad Laboratories, Calif.). Between 3 to 30 µg of plant protein extract was used per assay. Activity of the 3-ketothiolase enzyme in the different extracts was assayed according to the procedure of Senior, P. J. and Dawes, E. A., Biochem. J. 134: 225–238, 1973.

Assay for Acetoacetyl-CoA Reductase Activity

Frozen leaf samples (0.1 g) were homogenized in 200 µl of ice-cold reductase buffer containing 100 mM $KH_2PO_4$ (pH 5.5), 0.02 mM $MgCl_2$ and 4.0 mM β-mercaptoethanol. The homogenate was clarified by centrifugation at 10000×g for 5 min and the supernatant transferred to a fresh tube. The protein content of the extract was measured by the Bradford assay using the Bio Rad protein assay kit. Between 0.8 to 10 µg of plant protein extract was used per assay. Activity of the acetoacetyl-CoA reductase enzyme was assayed according to the procedure of Senior, P. J. and Dawes, E. A., Biochem. J. 134: 225–238, 1973.

Western Blot Analysis

For Western blot analysis, crude protein extracts prepared as described above for the enzyme activity assays were used. For the analysis of the expression of PHB synthase frozen leaf samples (0.1 g) were homogenized in 200 µl ice-cold buffer containing 100 mM Tris-HCl (pH 8.0), 5 mM EDTA and 4 mM β-mercaptoethanol. The homogenate was clarified by centrifugation at 10000×g for 5 min and the supernatant transferred to a fresh tube. In some experiments, the membrane and particulate fractions were partly solubilized in extraction buffer containing 1% SDS and again clarified by centrifugation. The protein content of these samples was measured by a modified Lowry method (Markwell, M. A. K., Haas, M., Bieber, L. L. and Tolbert, N. E., Anal. Biochemistry 87, 206–210 (1978).

Aliquots of the supernatants were separated by sodium dodecyl sulphate polyacrylamide gel electrophoresis (SDS PAGE) according to Laemmli, Nature 227: 680–685, 1970. The proteins were electrophoretically transferred to nitrocellulose filters. The Western blot analysis was performed as recommended in the ECL Western blotting protocol (Amersham International plc, Amersham UK). For blocking the filters TBS (20 mM Tris-HCL, pH 7.6, 137 mM NaCl) with 5% fat-free milk powder/0.12% Tween 20 was chosen. The first antibody was diluted 1:1000 in blocking solution before incubating the filters. The antibody reaction was detected by the ECL Western blotting detection system (Amersham International plc, Amersham UK).

Analysis of Polyhydroxybutyrate

For gas chromatographic analyses, 20–100 mg of leaf material was extracted 3–4 times with 50% ethanol and then with 100% methanol for 45 min—1 h at 55 ° C. Dry residues were extracted at 55° C. with 0.5 ml chloroform for at least 12 h and transesterified for 4– 6 h in 0.8M HCl in ethanol at 100° C. After extraction with 0.9M NaCl, the chloroform phase was analyzed on a Hewlett Packard 5890 series II gas chromatograph. Bacterial PHB (Sigma) was used as a standard. For visualization of PHB granules by epi-fluorescence microscopy, leaf samples were fixed in 2% glutaraldehyde in 10 mM phosphate buffer (pH 7.2) for 2 h. Tissues were rinsed in water and stained for 5 min in 1% Nile Blue A. Tissues were rinsed several times in water and soaked 1 min in 8% acetic acid followed by a final rinse of water. PHB granules were visualized by epiflorescence microscopy under an excitation wavelength of 546 or 565 nm (Ostle, A. G. & Holt J. G. Appl. Environ. Microbiol. 44, 238–241, 1982).

Transmission-Electron Microscopy.

Tissues samples were fixed in 0.8% glutaraldehyde/2% paraformaldehyde in 0.01M phosphate buffer (pH 7.2) for 2 h under a slight vacuum. After 4 washes with phosphate buffer, the samples were treated with 1% osmium tetroxide for 40 to 60 min. The samples were dehydrated in a graded ethanol series and embedded in Spurr's resin (Ted Pella Inc.). Sections of 80–90 nm were cut, placed on copper grids, and stained with 5% uranyl acetate for 30–45 min, following by staining with Reynolds lead citrate for 3–4 min. Sections were viewed in a JEOL100CX II transmission electron microscope operated at 80 kV.

Although the specific example of the invention described here involved the plant *Arabidopsis thaliana*, genes from *Alcaligenes eutrophus* and a transit peptide of pea, the invention is of general utility. The claims pertaining to production of poly-D-(-)-3-hydroxybutyrate and/or polyhydroxyalkanoate in the plastids of plants is not limited to *Arabidopsis thaliana*, or linked specifically to the use of genes from *Alcaligenes eutrophus* or the described transit peptide for plastid targeting. The claims described below describe a general method for the production of polyhydroxyalkanoate in the plastid of plants through the introduction of foreign DNA material into plant cells.

The improvements in the present invention are:

1-Transformation of plant cells with foreign DNA material encoding information leading to the production in the plastid of an enzyme possessing a 3-ketothiolase activity. The term "foreign DNA material" refers to DNA material which is not normally present in an organism, but which is introduced into a cell and resides either integrated into the chromosome, or resides in an extra-chromosomal form. An increase in 3-ketothiolase activity in the plastids of plant cells results from the introduction of foreign DNA material into plant cells.

2-Transformation of plant cells with foreign DNA material encoding information leading to the production in the plastids of an enzyme possessing an acetoacetyl-CoA reductase activity. An increase in acetoacetyl-CoA reductase activity in the plastids results from the introduction of foreign DNA material into plant cells.

3-Transformation of plant cells with foreign DNA material leading to the production of hydroxyacyl-CoA in the plastids which is foreign to the plant cell. Transformation of plant cells with foreign DNA material leading to the production of an increased level of hydroxyacyl-CoA in the plastids of plant cells.

4-Transformation of plant cells with foreign DNA material encoding information leading to the production in the plastids of an enzyme possessing the ability to polymerize hydroxyacyl-CoA of plant cells. An increase in an enzyme activity leading to the polymerization of hydroxyacyl-CoA in the plastids of plant cells results from the introduction of foreign DNA material into plant cells.

5-Production of a polyhydroxyalkanoate, including poly-D-(-)-3-hydroxybutyrate, in the plastids of plant cells through the introduction of foreign DNA material into plant cells.

6-Production of polyhydroxyalkanoate in the plastids of plant cells, is preferably at a level higher than 2 µg polyhydroxyalkanoate per gram of fresh plant material.

7-Production of polyhydroxyalkanoate in plastids is preferably at a level higher than 2 µg polyhydroxyalkanoate per gram of fresh plant material, in any plant cell for which it is possible to introduce foreign DNA material.

8-Production of polyhydroxyalkanoate in the plastids of hybrid plants is preferably at a level higher than 2 µg polyhydroxyalkanoate per gram of fresh plant material, resulting from cross-pollination between two parental plant lines having been transformed with foreign DNA material, but which by themselves do not produce polyhydroxyalkanoate in plastids, or produce polyhydroxyalkanoate at a level lower than produced in the hybrid plant.

9-Production of polyhydroxyalkanoate in the form of granules inside of the plastids of plant cells.

The seeds containing the genes of FIGS. 3 and 4 are maintained at Michigan State University, East Lansing, Mich.

| Deposit of Plasmids The following plasmids, discussed above, have been deposited with the American Type Culture Collection (12301 Parklawn Drive, Rockville, Maryland 20852, U.S.A.) on January 19, 1996: | |
|---|---|
| Plasmid | ATCC Designation No. |
| pBI-TPSS-Syn | 97417 |
| pBIB-KCN-Red | 97418 |
| pBIB-CCN-Thio | 97419 |
| pBI-TPSS-Red | 97420 |
| pBI-TPSS-Thio | 97421 |
| pBIB-HCN-Syn | 97422 |

It is intended that the foregoing description be only illustrative of the present invention and that the present invention be limited only by the hereinafter appended claims.

We claim:

1. A transgenic plant material having plastids, the plant material containing foreign DNA encoding a bacterial polypeptide which is selected from the group consisting of 3 ketothiolase, acetoacetyl-CoA reductase and polyhydroxyalkanoate (PHA) synthase and mixtures thereof leading to the production of a polyhydroxyalkanoate in the plastid in the plant material; wherein the bacterial polypeptide encoded by the foreign DNA is operably fused at its amino terminus to a transit peptide which effects targeting of the polypeptide into the plastid of the plant material.

2. The plant of claim 1 wherein the polyhydroxyalkanoate (PHA) is polyhydroxybutyrate (PHB).

3. The plant material of claim 2 wherein coding sequence of the DNA and RNA for the production of the enzymes leading to polyhydroxybutyrate (PHB) synthesis are as shown in SEQ ID NO:1, SEQ ID NO:2 and SEQ ID NO:3.

4. A transgenic plant material having plastids, the plant material containing foreign DNA encoding a bacterial polypeptide which exhibits 3-ketothiolase activity in the plastid in the plant material; wherein bacterial polypeptide encoded by the foreign DNA is operably fused at its amino terminus to a transit peptide which effects targeting of the polypeptide into the plastid of the plant material.

5. The plant material of claim 4 wherein the DNA which contains an open reading frame is shown in SEQ ID NO:1.

6. A transgenic plant material having plastids, the plant material containing foreign DNA encoding a bacterial polypeptide which exhibits acetoacetyl-CoA reductase activity in the plastid of the plant material; wherein the bacterial polypeptide encoded by the foreign DNA is operably fused at its amino terminus to a transit peptide which effects targeting of the polypeptide into the plastid of the plant material.

7. The transgenic plant material of claim 6 wherein the DNA which contains an open reading frame is shown in SEQ ID NO:2.

8. A transgenic plant material having plastids, the plant material containing foreign DNA encoding a bacterial polypeptide which exhibits PHA synthase activity in the plastid of the plant material; wherein the bacterial polypeptide encoded by the foreign DNA is operably fused at its amino terminus to a transit peptide which effects targeting of the polypeptide into the plastid of the plant material.

9. A transgenic plant material having plastids, the plant material containing foreign DNA encoding one or more bacterial enzymes leading to the synthesis of polyhydroxyalkanoate (PHA) from hydroxyacyl-CoA in the plastid of the plant material; wherein each of said enzymes encoded by the foreign DNA is operably fused at its amino terminus to a transit peptide which effects targeting of the enzyme into the plastid of the plant material.

10. The plant material of claim 9 wherein the DNA is in SEQ ID NO:3.

11. A transgenic plant material having plastids, the plant material containing foreign DNA encoding one or more bacterial enzymes which catalyze synthesis of hydroxyacyl-CoA in the plastid of the plant material; wherein each of the said enzymes encoded by foreign DNA is operably fused at its amino terminus to a transit peptide which effects targeting of the enzyme into the plastid of the plant material.

12. A transgenic plant having plastids, the plant containing foreign DNA encoding one or more bacterial enzymes leading to production of acetoacetyl-CoA, from products encoded by the foreign DNA, in the plastid of the plant; wherein each of said enzymes encoded by the foreign DNA is operably fused at its amino terminus to a transit peptide which effects targeting of the enzyme into the plastid of the plant material.

13. The plant material of claim 1 as an embryo, seed or propagule of the seed.

14. The plant material of claim 2 as an embryo, seed or propagule of the seed.

15. The plant material of claim 3 as an embryo, seed or propagule of the seed.

16. The plant material of claim 4 as am embryo, seed or propagule of the seed.

17. The plant material of claim 5 as an embryo, seed or propagule of the seed.

18. The plant material of claim 6 as an embryo, seed or propagule of the seed.

19. The plant material of claim 7 as an embryo, seed or propagule of the seed.

20. The plant material of claim 8 as an embryo, seed or propagule of the seed.

21. The plant material of claim 10 as an embryo, seed or propagule of the seed.

22. The plant material of claim 11 as an embryo, seed or propagule of the seed.

23. The plant cell of claim 12 as an embryo, seed or propagule of the seed.

24. A method for introducing foreign DNA encoding polypeptides leading to the synthesis of a polyhydroxyalkanoate (PHA) in a plastid in a plant which comprises mating by sexual fertilization two plants which do not produce PHA, each containing foreign DNA from a bacterium encoding one or more different enzymes in a pathway leading to polymerization of hydroxyacyl-CoA by PHA synthase to produce the plant which synthesizes the PHA in a plastid in the plant; wherein each of said enzymes encoded by the foreign DNA is operably fused at its amino terminus to a transit peptide which effects targeting of the enzyme into the plastid of the plant.

25. The method of claim 24 wherein the PHA is polyhydroxybutyrate (PHB).

26. A gene segment as contained in plasmid pBI-TPSS-Thio or pBIB-CCN-Thio, the gene segment encoding a modified 3-ketothiolase polypeptide for targeting to a plastid of a plant; wherein the 3-ketothiolase polypeptide is operably fused at its amino terminus to a transit peptide which effects targeting of the polypeptide into the plastid of the plant.

27. A plant containing the gene segment of claim 26.

28. The plant of claim 27 which is *Arabidopsis thaliana*.

29. A gene segment as contained in plasmid pBI-TPSS-Red from *Alcaligenes eutrophus*, the gene segment encoding a modified acetoacetyl-CoA reductase polypeptide for targeting to a plastid of a plant; wherein the acetoacetyl-CoA reductase polypeptide is operably fused at its amino terminus to a transit peptide which effects targeting of the polypeptide into the plastid of the plant.

30. A plant containing the gene segment of claim 29.

31. The plant of claim 30 which is *Arabidopsis thaliana*.

32. A gene segment as contained in plasmid pBI-TPSS-Syn or pBIB-HCN-Syn from *Alcaligenes eutrophus*, the gene segment encoding a modified polyhydroxybutyrate (PHB) synthase polypeptide for targeting to a plastid of a plant; wherein the polyhydroxybutyrate synthase polypeptide is operably fused at its amino terminus to a transit peptide which effects targeting of the polypeptide into the plastid of the plant.

33. A plant containing the gene segment of claim 32.

34. The plant of claim 24 which is *Arabidopsis thaliana*.

35. A transgenic plant material having plastids, the plant material containing foreign DNA encoding one or more bacterial enzymes leading to production of 3-hydroxybutyryl-CoA, from products encoded by the foreign DNA, in the plastid in the plant material; wherein the each of said enzymes incoded by foreign DNA is operably fused at its amino terminus to a transit peptide which effects targeting of the polypeptide into the plastid of the plant material.

36. A method for producing polyhydroxyalkanoate comprising:

a) mating by sexual fertilization two plants which do not produce PHA, each containing foreign DNA from a bacterium encoding one or more different enzymes in a pathway leading to polymerization of hydroxyacyl-CoA by PHA synthase to produce the plant which synthesizes the PHA in a plastid in the plant; wherein the each of said enzymes encoded by foreign DNA is operably fused at its amino terminus to a transit peptide which effects targeting of the polypeptide into the plastid of the plant.

b) recovering the polyhydroxyalkanoate.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 1431 Base Pairs
( B ) TYPE: Nucleic Acid
( C ) STRANDEDNESS: Double
( D ) TOPOLOGY: Linear ( i i ) MOLECULE TYPE:
( A ) DESCRIPTION: Genomic DNA ( i i i ) HYPOTHETICAL: No ( i v ) ANTI-SENSE: No ( v i ) ORIGINAL SOURCE:
( A ) ORGANISM: Alcaligenes eutrophus ( v i i ) IMMEDIATE SOURCE:
( A ) LIBRARY: Genomic ( x i ) SEQUENCE DESCRIPTION: SEQ ID NO: 1:

| ATG | GCT | TCT | ATG | ATA | TCC | TCT | GCT | GTG | ACA | ACA | GTC | AGC | CGT | GCC | TCT | AGG | 54 |
|---|---|---|---|---|---|---|---|---|---|---|---|---|---|---|---|---|---|
| Met | Ala | Ser | Met | Ile | Ser | Ser | Ala | Val | Thr | Thr | Val | Ser | Arg | Ala | Ser | Arg | |
| | | | | 5 | | | | 10 | | | | | 15 | | | | |

| GGG | CAA | TCC | GCC | GCA | GTC | GCT | ACT | TTC | GGC | CTC | AAA | TCC | ATG | ACT | GGA | TTC | 108 |
|---|---|---|---|---|---|---|---|---|---|---|---|---|---|---|---|---|---|
| Gly | Gln | Ser | Ala | Ala | Val | Ala | Thr | Phe | Gly | Leu | Lys | Ser | Met | Thr | Gly | Phe | |
| 20 | | | | | 25 | | | | 30 | | | | 35 | | | | |

| CCA | GTG | AAG | AAG | GTC | AAC | ACT | ATT | GAC | ATT | ACA | AAG | AGC | AAT | GGT | GGA | AGA | 162 |
|---|---|---|---|---|---|---|---|---|---|---|---|---|---|---|---|---|---|
| Pro | Val | Lys | Lys | Val | Asn | Thr | Ile | Asp | Ile | Thr | Lys | Ser | Asn | Gly | Gly | Arg | |
| | 40 | | | | | 45 | | | | 50 | | | | | | | |

| GTA | AAG | TGC | ATG | CAG | GTG | TGG | CCT | ATT | GGA | AAG | AAG | TTT | GAG | ACT | CTT | | 216 |
|---|---|---|---|---|---|---|---|---|---|---|---|---|---|---|---|---|---|
| Val | Lys | Cys | Met | Gln | Val | Trp | Pro | Ile | Gly | Lys | Lys | Phe | Glu | Thr | Leu | | |
| 55 | | | 60 | | | | | 65 | | | | | 70 | | | | |

| TCC | TAT | TTG | CCA | CCA | TTG | ACG | AGA | TCC | CGG | GTG | ACT | GAC | GTT | GTC | ATC | GTA | 270 |
|---|---|---|---|---|---|---|---|---|---|---|---|---|---|---|---|---|---|
| Ser | Tyr | Leu | Pro | Pro | Leu | Thr | Arg | Ser | Arg | Val | Thr | Asp | Val | Val | Ile | Val | |
| | 75 | | | | | 80 | | | | 85 | | | | | | 90 | |

| TCC | GCC | GCC | CGC | ACC | GCG | GTC | GGC | AAG | TTT | GGC | GGC | TCG | CTG | GCC | AAG | ATC | CCG | 324 |
|---|---|---|---|---|---|---|---|---|---|---|---|---|---|---|---|---|---|

-continued

| | | | | | | | | | | |
|---|---|---|---|---|---|---|---|---|---|---|
| Ser | Ala | Arg | Thr<br>95 | Ala | Val | Gly | Lys | Phe<br>100 | Gly | Gly | Ser | Leu | Ala<br>105 | Lys | Ile | Pro | |
| GCA<br>Ala | CCG<br>Pro<br>110 | GAA<br>Glu | CTG<br>Leu | GGT<br>Gly | GCC<br>Ala<br>115 | GTG<br>Val | ATC<br>Ile | AAG<br>Lys | GCC<br>Ala<br>120 | GCG<br>Ala | CTG<br>Leu | GAG<br>Glu | CGC<br>Arg<br>125 | GGC<br>Gly | GTC<br>Val | 378 |
| AAG<br>Lys | CCG<br>Pro | GAG<br>Glu<br>130 | CAG<br>Gln | GTG<br>Val | GAA<br>Glu | GTC<br>Val | CAG<br>Gln<br>135 | ATG<br>Met | ATC<br>Ile | ACC<br>Thr | GCC<br>Ala<br>140 | CTC<br>Leu | GCC<br>Ala | GGT<br>Gly | TCG<br>Ser | 432 |
| GGC<br>Gly | CAG<br>Gln | AAC<br>Asn<br>145 | CCC<br>Pro | GCA<br>Ala<br>150 | CGC<br>Arg | CAG<br>Gln | GCC<br>Ala | ATC<br>Ile<br>155 | AAG<br>Lys | GGC<br>Gly | CTC<br>Leu | GCG<br>Ala<br>160 | ATG<br>Met | GCG<br>Ala | GTG<br>Val | 486 |
| CCG<br>Pro | GCC<br>Ala<br>165 | ATG<br>Met | ACC<br>Thr | ATC<br>Ile | TGC<br>Cys<br>170 | GGC<br>Gly | TCG<br>Ser | CTG<br>Leu<br>175 | AAG<br>Lys | AAG<br>Lys | GTG<br>Val | ATG<br>Met<br>180 | CTG<br>Leu | | | 540 |
| GCC<br>Ala | GCC<br>Ala<br>185 | ATG<br>Met | GCG<br>Ala | ATC<br>Ile | GAC<br>Asp | GCC<br>Ala<br>190 | GCC<br>Ala | GTG<br>Val<br>195 | GCC<br>Ala | GGC<br>Gly | ATG<br>Met | CAG<br>Gln | | | | 594 |
| GAA<br>Glu<br>200 | AGC<br>Ser | GCC<br>Ala | CAC<br>His | ATC<br>Ile | CTG<br>Leu | CCG<br>Pro<br>205 | TCG<br>Ser | GAT<br>Asp | CGC<br>Arg<br>210 | GGC<br>Gly | TTC<br>Phe<br>215 | CGC<br>Arg | | | | 648 |
| ATG<br>Met | GGT<br>Gly | GAT<br>Asp | CTG<br>Leu | GTC<br>Val | GAC<br>Asp | TCG<br>Ser<br>225 | GTC<br>Val | CTG<br>Leu | GGC<br>Gly<br>230 | GAC<br>Asp | TGG<br>Trp | GTG<br>Val | | | | 702 |
| TAC<br>Tyr<br>235 | TAC<br>Tyr | ATG<br>Met<br>240 | GGC<br>Gly | ATC<br>Ile | ACC<br>Thr | GAG<br>Glu<br>245 | AAC<br>Asn | GTC<br>Val | AAG<br>Lys | GAA<br>Glu<br>250 | GGC<br>Gly | | | | | 756 |
| ATC<br>Ile | ACA<br>Thr | CTG<br>Leu | GAG<br>Glu | GAT<br>Asp | ATC<br>Ile | GAG<br>Glu<br>260 | GAA<br>Glu | TCG<br>Ser<br>265 | CTG<br>Leu | AAG<br>Lys | CTG<br>Leu<br>270 | | | | | 810 |
| GCC<br>Ala | GCG<br>Ala | CAG<br>Gln | AAG<br>Lys<br>275 | GGC<br>Gly | AAG<br>Lys | GAG<br>Glu<br>280 | ATC<br>Ile | GTG<br>Val<br>285 | GCC<br>Ala | CTG<br>Leu | | | | | | 864 |
| CAG<br>Gln | CGC<br>Arg<br>290 | CAG<br>Gln | CCG<br>Pro<br>295 | GGC<br>Gly | GAC<br>Asp<br>300 | AAG<br>Lys | TTC<br>Phe | CGC<br>Arg | CAG<br>Gln<br>305 | | | | | | | 918 |
| GCC<br>Ala | ACG<br>Thr | CTG<br>Leu | TCC<br>Ser | ATG<br>Met | AAG<br>Lys | CCC<br>Pro | TTC<br>Phe | CTC<br>Leu<br>315 | GAC<br>Asp<br>320 | | | | | | | 972 |
| ACC<br>Thr | GCG<br>Ala | AAC<br>Asn | TCG<br>Ser | CTG<br>Leu | AAC<br>Asn | GAC<br>Asp | GCC<br>Ala | GGC<br>Gly | GTG<br>Val | | | | | | | 1026 |
| GTG<br>Val | | | | | | | | | | | | | | | | |

-continued

| 325 | | | | 330 | | | | 335 | | | | 340 | | | | |
|---|---|---|---|---|---|---|---|---|---|---|---|---|---|---|---|---|
| ATG | TCG | GCG | GCC | AAG | GCC | AAG | GAA | CTG | GGC | ACC | CCG | CTG | GCC | ACG | ATC | AAG | 1080 |
| Met | Ser | Ala | Ala | Lys | Ala | Lys | Glu | Leu | Gly | Thr | Pro | Leu | Ala | Thr | Ile | Lys |
| | | 345 | | | | | 350 | | | | 355 | | | | | 360 |
| AGC | TAT | GCC | AAC | GCC | GGT | GTC | GAT | CCC | ATG | GGC | ATG | CCG | GGC | CCG | GTG | CCG | 1134 |
| Ser | Tyr | Ala | Asn | Ala | Gly | Val | Asp | Pro | Met | Gly | Met | Pro | Gly | Pro | Val | Pro |
| | | | | 365 | | | | | 370 | | | | | 375 | | |
| GCC | TCC | AAG | CGC | GCC | CTG | TCG | CGC | GAG | TGG | ACC | CAA | GAC | CTG | GAC | CAG | CTG | 1188 |
| Ala | Ser | Lys | Arg | Ala | Leu | Ser | Arg | Glu | Trp | Thr | Pro | Gln | Asp | Leu | Asp | Leu |
| | 380 | | | | | 385 | | | | | 390 | | | | | 395 |
| ATG | GAG | ATC | AAC | GAG | TTT | GCC | GCC | GCG | CTG | GCG | GTG | CAC | CAG | CAG | CAG | ATG | 1242 |
| Met | Glu | Ile | Asn | Glu | Phe | Ala | Ala | Ala | Leu | Ala | Val | His | Gln | Gln | Gln | Met |
| | | | 400 | | | | | 405 | | | | | 410 | | | |
| GGC | TGG | GAC | ACC | AAG | TCC | AAT | GTC | AAC | GGC | GGC | GCC | ATC | ATC | GGC | CAC | CCG | 1296 |
| Gly | Trp | Asp | Thr | Lys | Ser | Asn | Val | Asn | Gly | Gly | Ala | Ile | Ile | Gly | His | Pro |
| 415 | | | | | 420 | | | | | 425 | | | | | 430 | |
| CCG | ATC | GGC | GCG | TCG | GCG | TGC | CGT | ATC | CTG | GTG | ACG | CTG | CAC | CAC | AAG | CGC | 1350 |
| Pro | Ile | Gly | Ala | Ser | Ala | Cys | Arg | Ile | Leu | Val | Thr | Leu | His | His | Lys | Arg |
| | | | 435 | | | | | 440 | | | | | 445 | | | 450 |
| CGC | CGT | GAC | GCG | AAG | GCG | AAG | GCC | CTG | CTG | GGC | ATC | GGC | ATG | GGC | | |
| Arg | Arg | Asp | Ala | Lys | Ala | Lys | Ala | Leu | Leu | Gly | Ile | Gly | Met | Gly | | | 1404 |
| | | | | 455 | | | | | 460 | | | | | 465 | | |
| GTG | GCG | CTG | GCA | GTC | GAG | CGC | AAA | TAA | | | | | | | | | 1431 |
| Val | Ala | Leu | Ala | Val | Glu | Arg | Lys | *** |
| 470 | | | | | 475 |

( 2 ) INFORMATION FOR SEQ ID NO:2:

( i ) SEQUENCE CHARACTERISTICS:
        ( A ) LENGTH: 990 Base Pairs
        ( B ) TYPE: Nucleic Acid
        ( C ) STRANDEDNESS: Double
        ( D ) TOPOLOGY: Linear ( i i ) MOLECULE TYPE:
        ( A ) DESCRIPTION: Genomic DNA ( i i i ) HYPOTHETICAL: No ( i v ) ANTI-SENSE: No ( v i ) ORIGINAL SOURCE:
        ( A ) ORGANISM: Alcaligenes eutrophus ( v i i ) IMMEDIATE SOURCE:
    ( A ) LIBRARY: Genomic ( x i ) SEQUENCE DESCRIPTION: SEQ ID NO: 2:

| ATG<br>Met | GCT<br>Ala | TCT<br>Ser | ATG<br>Met | ATA<br>Ile<br>5 | TCC<br>Ser | TCT<br>Ser | TCT<br>Ser | GCT<br>Ala | GTG<br>Val<br>10 | ACA<br>Thr | GTC<br>Val | AGC<br>Ser | CGT<br>Arg<br>15 | GCC<br>Ala | TCT<br>Ser | AGG<br>Arg | 54 |
| GGG<br>Gly | CAA<br>Gln<br>20 | TCC<br>Ser | GCA<br>Ala | GCT<br>Ala<br>25 | GTG<br>Val | AAG<br>Lys | CCA<br>Pro | TTC<br>Phe | CTC<br>Leu<br>30 | AAA<br>Lys | TCC<br>Ser | ATG<br>Met | ACT<br>Thr<br>35 | GGA<br>Gly | TTC<br>Phe | 108 |
| CCA<br>Pro | GTG<br>Val | AAG<br>Lys<br>40 | GTC<br>Val | AAC<br>Asn | GTC<br>Val | ACT<br>Thr | ATT<br>Ile<br>45 | ACT<br>Thr | GAC<br>Asp | AGC<br>Ser | ACA<br>Thr | ATT<br>Ile<br>50 | AAT<br>Asn | GGT<br>Gly | GGA<br>Gly | AGA<br>Arg | 162 |
| GTA<br>Val<br>55 | TGC<br>Cys | ATG<br>Met | CAG<br>Gln | GTG<br>Val<br>60 | TGG<br>Trp | CCT<br>Pro | CCA<br>Pro | ATT<br>Ile | GGA<br>Gly<br>65 | AAG<br>Lys | AAG<br>Lys | TTT<br>Phe | GAG<br>Glu<br>70 | ATT<br>Ile | ACT<br>Thr | CTT<br>Leu | 216 |
| TCC<br>Ser | TAT<br>Tyr<br>75 | TTG<br>Leu | CCA<br>Pro | CCG<br>Pro | ACG<br>Thr | AGA<br>Arg<br>80 | GAT<br>Asp | GTG<br>Val | ACT<br>Thr | CAG<br>Gln<br>85 | CGG<br>Arg | CAG<br>Gln | ATT<br>Ile | GCG<br>Ala | TAT<br>Tyr<br>90 | | 270 |
| GTG<br>Val | ACC<br>Thr | GGC<br>Gly | ATG<br>Met<br>95 | GGT<br>Gly | GGA<br>Gly | ATC<br>Ile | GCC<br>Ala<br>100 | ACC<br>Thr | TGC<br>Cys | CGC<br>Arg<br>105 | CTG<br>Leu | GCC<br>Ala | AAG<br>Lys | | | | 324 |
| GAT<br>Asp | GGC<br>Gly<br>110 | TTT<br>Phe | CGT<br>Arg | GTG<br>Val | CAG<br>Gln | GGC<br>Gly<br>115 | TGC<br>Cys | TGC<br>Cys | TCG<br>Ser | CCC<br>Pro<br>120 | CGG<br>Arg | CGC<br>Arg | GAA<br>Glu<br>125 | AAG<br>Lys | | | 378 |
| TGG<br>Trp | CTG<br>Leu | CAG<br>Gln<br>130 | CAG<br>Gln | CTG<br>Leu | AAG<br>Lys | TCG<br>Ser<br>135 | GGT<br>Gly | GCC<br>Ala | ACC<br>Thr | AAG<br>Lys<br>140 | GCC<br>Ala | GCC<br>Ala | TCC<br>Ser | GAG<br>Glu | AAG<br>Lys<br>145 | | 432 |
| GCT<br>Ala | TGG<br>Trp | GAT<br>Asp | GTT<br>Val<br>150 | GAT<br>Asp | ATC<br>Ile | ATC<br>Ile | ACC<br>Thr<br>155 | TTC<br>Phe | GGT<br>Gly | GTG<br>Val | ACC<br>Thr | AAG<br>Lys<br>160 | GCC<br>Ala | TCC<br>Ser | AAT<br>Asn | | 486 |
| GGA<br>Gly | GAG<br>Glu<br>165 | GAT<br>Asp | GTT<br>Val | GAT<br>Asp | CTG<br>Leu | ATC<br>Ile<br>170 | AAC<br>Asn | ACC<br>Thr | CGG<br>Arg<br>175 | ACC<br>Thr | GAC<br>Asp | GTG<br>Val | TTC<br>Phe<br>180 | | | | 540 |
| CGC<br>Arg | AAG<br>Lys<br>185 | ATG<br>Met | ACC<br>Thr | CGC<br>Arg | GAT<br>Asp<br>190 | GCG<br>Ala | GAT<br>Asp | GAC<br>Asp | GAC<br>Asp<br>195 | AAC<br>Asn | CTG<br>Leu | ACC<br>Thr | TCG<br>Ser | GGC<br>Gly | | | 594 |
| CTG<br>Leu | TTC<br>Phe<br>200 | AAC<br>Asn | GTC<br>Val | CAG<br>Gln<br>205 | ACC<br>Thr | AAG<br>Lys | GCC<br>Ala | ATG<br>Met<br>210 | GAC<br>Asp | GCC<br>Ala | CGT<br>Arg | TGG<br>Trp<br>215 | GGC<br>Gly | | | | 648 |

-continued

```
CGC ATC GTC AAC ATC TCG TCG GTG AAC GGG AAG GGG CAG TTC GGC CAG ACC   702
Arg Ile Val Asn Ile Ser Ser Val Asn Gly Lys Gly Gln Phe Gly Gln Thr
        220                 225                 230

AAC TAC TCC GCC AAG GCC GCC GGC CAT CTG TTC ACC ATG GCA CTG GCG CAG   756
Asn Tyr Ser Ala Lys Ala Ala Gly His Leu Phe Thr Met Ala Leu Ala Gln
235                 240                 245                 250

GAA GTG GCG ACC AAG GGC GTG ACC AAC GTC TCT GGC TAT ATC GCC           810
Glu Val Ala Thr Lys Gly Val Thr Asn Val Ser Gly Tyr Ile Ala
        255                 260                 265                 270

ACC GAC ATG GTC AAG GCG ATC CGC CAG GAC CTC GAC AAG GTC GCG ACG       864
Thr Asp Met Val Lys Ala Ile Arg Gln Asp Leu Asp Lys Val Ala Thr
            275                 280                 285

ATC CCG GTC AAG CGC CTG GGC CTG GAA ATC GCC TCG ATC TGC GCC TGG       918
Ile Pro Val Lys Arg Leu Gly Leu Glu Ile Ala Ser Ile Cys Ala Trp
    290                 295                 300                 305

TTG TCG TCG GAG GAG TCC GGT TTC ACC GGC GAC TTC TCG CTC AAC GGC       972
Leu Ser Ser Glu Glu Ser Gly Phe Thr Gly Asp Phe Ser Leu Asn Gly
            310                 315                 320

GGC CTG CAT ATG GGC TGA                                                990
Gly Leu His Met Gly ***
325
```

( 2 ) INFORMATION FOR SEQ ID NO:3:

( i ) SEQUENCE CHARACTERISTICS:
        ( A ) LENGTH: 2019 Base Pairs
        ( B ) TYPE: Nucleic Acid
        ( C ) STRANDEDNESS: Double
        ( D ) TOPOLOGY: Linear ( i i ) MOLECULE TYPE:
        ( A ) DESCRIPTION: Genomic DNA ( i i i ) HYPOTHETICAL: No ( i v ) ANTI-SENSE: No ( v ) ORIGINAL SOURCE:
        ( A ) ORGANISM: Alcaligenes eutrophus ( v i i ) IMMEDIATE SOURCE:
        ( A ) LIBRARY: Genomic ( x i ) SEQUENCE DESCRIPTION: SEQ ID NO: 3:

```
ATG GCT TCT ATG ATA TCC TCT TCC GCT GTG ACA ACA GTC AGC CGT GCC TCT AGG   54
```

-continued

```
Met Ala Ser Met Ile Ser Ser Ala Val Thr Thr Val Ser Arg Ala Ser Arg
                                                              15                                                              108

GGG CAA TCC GCT GTG GCA TTC CCA GGC CTC ATG ACT GGA TTC
Gly Gln Ser Ala Val Ala Phe Pro Gly Leu Met Thr Gly Phe
     20                    25                    30             35                                                         162

CCA AAG GTC AAC AGC ACT ATT GAC ATT TCC ACA AAT GGT GGA AGA
Pro Lys Val Asn Ser Thr Ile Asp Ile Ser Thr Asn Gly Gly Arg
     40                    45                    50                                                                         216

GTA TGC ATG CAG GTG TGG CAG ATT CCA CCT GGA AAG AAG TTT GAG ACT CTT
Val Cys Met Gln Val Trp Gln Ile Pro Pro Gly Lys Lys Phe Glu Thr Leu
55                    60                    65                    70                                                       270

TCC TAT TTG CCA ACG TTG CCA AGA ACG TCC CAA GGC GCG GTG GCG GCG CCA
Ser Tyr Leu Pro Thr Leu Pro Arg Thr Ser Gln Gly Ala Val Ala Ala Pro
     75                    80                    85                    90                                                   324

GCA GCT TCC ACG CAG CCA CGG TTC CAA GTC AAG ACC ACT GGC
Ala Ala Ser Thr Gln Pro Arg Phe Gln Val Lys Thr Thr Gly
     95              100                   105                                                                              378

TTC GAT CCA ACA TGG CTG GAA TCC TGG TCA CAG CAG CTG GAA
Phe Asp Pro Thr Trp Leu Glu Ser Trp Ser Gln Gln Leu Glu
     110                   115                   120                   125                                                  432

AAC GGC CAC GCC GCC GCG GCG GGC TCC ATT GAT GGT TAC GCA GGC
Asn Gly His Ala Ala Ala Ala Gly Ser Ile Asp Gly Tyr Ala Gly
     130                   135                   140                                                                        486

AAG ATC GCT CAG CAG GCG ATG AAG ATG TAC CTC GAG GAC CTG
Lys Ile Ala Gln Gln Ala Met Lys Met Tyr Leu Glu Asp Leu
     145                   150                   155                   160                                                  540

TCA GCG CTG CGG TGG TGG GCA GAC AAG ACC GGT TAT GCC CCG TTC
Ser Ala Leu Arg Trp Trp Ala Asp Lys Thr Gly Tyr Ala Pro Phe
     165                   170                   175                   180                                                  594

CAC GAC GCT GGC CGG GCA GAC AAT CTC ACC CTG GAG CTG CGC
His Asp Ala Gly Arg Ala Asp Asn Leu Thr Leu Glu Leu Arg
     185                   190                   195                   200                                                  648

GCT GCC GCC GCG GCG CTG CTG TAC AAG ACC ACG GCC ATC GAT GCC
Ala Ala Ala Ala Ala Leu Leu Tyr Lys Thr Thr Ala Ile Asp Ala
     200                   205                   210                   215                                                  702

GTC GAG GCA GCG GCT GCG CAG TTC TTT GCC TCG GAG GCG CAA TGG CAG
Val Glu Ala Ala Ala Ala Gln Phe Phe Ala Ser Glu Ala Gln Trp Gln
     220                   225                   230                                                                        756

GAT GCG ATG TCG CTT AAT ACC CCC AAT GCC CAG GCA CGC CGC
Asp Ala Met Ser Leu Asn Thr Pro Asn Ala Gln Ala Arg Arg
```

-continued

| | 235 | | | 240 | | | 245 | | | 250 | | | |
|---|---|---|---|---|---|---|---|---|---|---|---|---|---|
| CTG Leu | ATC Ile 255 | GAG Glu | TCG Ser | GGC Gly | GAA Glu 260 | TCG Ser | CTG Leu | CGT Arg | GCC Ala | GGC Gly 265 | GTG Val | CGC Arg | ATG Met 270 | 810 |
| GAA Glu | CTG Leu | GAC Asp | CGC Arg 275 | GGC Gly | AAG Lys | ATC Ile | TCG Ser | CAG Gln 280 | ACC Thr | AGC Ser | GAG Glu | GCG Ala 285 | TTT Phe | 864 |
| GGC Gly | AAT Asn 290 | GTC Val | GCG Ala | GTG Val | GCC Ala | GGC Gly 295 | GTG Val | TTC Phe | GTC Val 300 | AAC Asn | GAG Glu | TAC Tyr 305 | TTC Phe | 918 |
| CAG Gln | CTG Leu | CAG Gln 310 | TAC Tyr | AAG Lys | ACC Thr 315 | CTG Leu | CCG Pro | GAC Asp | CAC His | GCG Ala 320 | CCG Pro | CTG Leu | | 972 |
| ATG Met 325 | TTG Leu | CCG Pro | ATC Ile 330 | AAG Lys | AAC Asn | CCG Pro | AAG Lys | TAC Tyr | ATC Ile 335 | CTG Leu | CAG Gln | CGC Arg | AGC Ser | 1026 |
| TCG Ser | GTG Val | CTG Leu 345 | GTG Val | CAT His | TAC Tyr | CAG Gln | GAC Asp 350 | GTG Val | TTT Phe | CTG Leu | GTG Val 355 | TCG Ser | TGG Trp 360 | 1080 |
| CCG Pro | GTG Val | CGC Arg | CAG Gln | CAT His | GGA Gly 365 | CAG Gln | GGC Gly | TAC Tyr | GAC Asp | AGC Ser 370 | TAC Tyr | CTG Leu | GAG Glu | 1134 |
| CCG Pro | ATC Ile | GAC Asp 380 | AAT Asn | CCG Pro | ACC Thr | AGC Ser | GGC Gly 385 | ATG Met | GAA Glu | CGC Arg | ACC Thr | TGG Trp 390 | AAG Lys 395 | 1188 |
| GCG Ala | ATC Ile | CGC Arg 400 | GTC Val | GCC Ala | GTT Val | ATT Ile | GGC Gly 405 | GCC Ala | GTC Val | GAC Asp | CGC Arg | CAG Gln | GCG Ala | 1242 |
| CTG Leu | GCG Ala 415 | GAC Asp | TTC Phe | GGC Gly | GGC Gly 420 | GAG Glu | CCG Pro | ATC Ile | CTC Leu | AGC Ser 425 | ACC Thr | CTG Leu | ACG Thr 430 | 1296 |
| CTG Leu | TTT Phe 435 | GAC Asp | GCC Ala | ACG Thr | GAC Asp | GCC Ala 440 | ATC Ile | CTG Leu | GTC Val | TTT Phe | GTC Val 445 | GGC Gly | CAT His 450 | 1350 |
| CAG Gln | TTG Leu | CGC Arg | GAG Glu 455 | CTG Leu | GGC Gly | GGC Gly | GGC Gly 460 | GGC Gly | GCG Ala | TGC Cys 465 | CCG Pro | CTG Leu | GTG Val | 1404 |
| CGC Arg | GGC Gly 470 | CTT Leu | GAG Glu | CTG Leu | GAG Glu | ACC Thr | AAT Asn 475 | GCC Ala | TTC Phe | TCG Ser | TTG Leu 480 | CGC Arg | AAC Asn | CCG Pro | GAC Asp | CTG Leu 485 | GTG Val | 1458 |

```
TGG AAC TAC GTG GTC GAC AAC TAC CTG AAG GGC AAC ACG CCG GTG TTC GAC      1512
Trp Asn Tyr Val Val Asp Asn Tyr Leu Lys Gly Asn Thr Pro Val Phe Asp
            490                     495             500

CTG TTC TGG AAC GAC GGC GCC ACC AAC CTG GGC CCG GGG CCG TAC TGC TGG      1566
Leu Phe Trp Asn Asp Gly Ala Thr Asn Leu Gly Pro Gly Pro Tyr Cys Trp
505                     510                 515                 520

TAC CTG CGC CAC ACC TAC CTG CAG AAC GAG GTA AAG GGC CCG CCG AAG CTG ACC  1620
Tyr Leu Arg His Thr Tyr Leu Gln Asn Glu Val Lys Gly Pro Pro Lys Leu Thr
        525                 530             535                     540

GTG TGC GGC GTG GTA CCG GAC CTG TAC ACC ATC AGC GCC CTG GCA CCG GTA TAC  1674
Val Cys Gly Val Val Pro Asp Leu Tyr Thr Ile Ser Ala Leu Ala Pro Val Tyr
545                     550                 555

GGC TCG CGC GAA GAT CAT ATC CTG TGG CCG GTG ACC GCC TCG ACC GCC          1728
Gly Ser Arg Glu Asp His Ile Leu Trp Pro Val Thr Ala Ser Thr Ala
    560                 565                 570                 575

CTG GGC CTG CGC TTC CCG GTG TCG GGC TAT CCG GGT GGT                      1782
Leu Gly Leu Arg Phe Pro Val Ser Gly Tyr Pro Gly Gly
580                     585                     590

GTC ATC AAC AAG CGC AAG AAC AGC TGG CAC ACT CAC ATC GCC CTG              1836
Val Ile Asn Lys Arg Lys Asn Ser Trp His Thr His Ile Ala Leu
595                 600                 605                 610

CCG TCG GAG CAA GCA CAG CTG GGC CAT CAC GGC AGC                          1890
Pro Ser Glu Gln Ala Gln Leu Gly His His Gly Ser
    615                 620                 625                 630

TGG GAC TGG ACC GCA GGG CGC GCC GGC AAA GCC CGA                          1944
Trp Asp Trp Thr Ala Gly Arg Ala Gly Lys Ala Arg
635                 640                 645

TAT AAT CGC TAT GCA GAA ATC GCC CCT CCG GGG                              1998
Tyr Asn Arg Tyr Ala Glu Ile Ala Pro Pro Gly
650             655                 660             665

TAC GTC AAG GCC AAG GCA TGA***                                           2019
Tyr Val Lys Ala Lys Ala ***
670
```